US010973762B2

(12) United States Patent
Kurihara et al.

(10) Patent No.: US 10,973,762 B2
(45) Date of Patent: Apr. 13, 2021

(54) ACTIVE-TARGETING-TYPE POLYMER DERIVATIVE, COMPOSITION CONTAINING SAID POLYMER DERIVATIVE, AND USES OF SAID POLYMER DERIVATIVE AND SAID COMPOSITION

(71) Applicant: Nippon Kayaku Kabushiki Kaisha, Tokyo (JP)

(72) Inventors: Dai Kurihara, Tokyo (JP); Tsuyoshi Fukuda, Tokyo (JP); Yuki Kawano, Tokyo (JP); Keiichirou Yamamoto, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 64 days.

(21) Appl. No.: 16/320,143

(22) PCT Filed: Jul. 25, 2017

(86) PCT No.: PCT/JP2017/026788
§ 371 (c)(1),
(2) Date: Jan. 24, 2019

(87) PCT Pub. No.: WO2018/025699
PCT Pub. Date: Feb. 8, 2018

(65) Prior Publication Data
US 2019/0262269 A1   Aug. 29, 2019

(30) Foreign Application Priority Data

Aug. 2, 2016 (JP) ................ 2016-152167

(51) Int. Cl.
| A61K 9/107 | (2006.01) |
| A61K 47/59 | (2017.01) |
| A61K 47/54 | (2017.01) |
| A61K 47/34 | (2017.01) |
| C08L 77/00 | (2006.01) |
| A61K 9/51 | (2006.01) |
| C08G 69/40 | (2006.01) |

(52) U.S. Cl.
CPC .............. *A61K 9/1075* (2013.01); *A61K 9/51* (2013.01); *A61K 47/34* (2013.01); *A61K 47/555* (2017.08); *A61K 47/595* (2017.08); *C08G 69/40* (2013.01); *C08L 77/00* (2013.01)

(58) Field of Classification Search
CPC .... A61K 47/34; A61K 47/555; A61K 47/595; A61K 9/1075; A61K 9/51; C08G 69/10; C08G 69/40; C08L 77/00
See application file for complete search history.

(56) References Cited

U.S. PATENT DOCUMENTS

| 5,449,513 A | 9/1995 | Yokoyama et al. |
| 5,510,103 A | 4/1996 | Yokoyama et al. |
| 2006/0067910 A1 | 3/2006 | Kitagawa et al. |
| 2006/0099265 A1 | 5/2006 | Shimizu et al. |
| 2007/0134332 A1 | 6/2007 | Turnell et al. |
| 2008/0113028 A1 | 5/2008 | Shimizu et al. |
| 2009/0156742 A1 | 6/2009 | Shimizu et al. |
| 2009/0239782 A1 | 9/2009 | Nakamura et al. |
| 2010/0221320 A1 | 9/2010 | Kato et al. |
| 2010/0234537 A1 | 9/2010 | Kitagawa et al. |
| 2010/0292414 A1 | 11/2010 | Kitagawa et al. |
| 2011/0201754 A1* | 8/2011 | Kitagawa ............. A61K 31/704 525/54.1 |
| 2013/0280306 A1 | 10/2013 | Sill et al. |
| 2013/0288991 A1 | 10/2013 | Sill et al. |
| 2013/0296531 A1 | 11/2013 | Sill et al. |
| 2014/0024703 A1 | 1/2014 | Shimizu et al. |
| 2014/0113879 A1 | 4/2014 | Carie et al. |
| 2014/0114051 A1 | 4/2014 | Semple |
| 2014/0127271 A1 | 5/2014 | Sill et al. |

(Continued)

FOREIGN PATENT DOCUMENTS

| CA | 2104045 C | 2/1997 |
| CN | 101568328 A | 10/2009 |

(Continued)

OTHER PUBLICATIONS

Wang et al.(Supporting Information for Adv. Nater. DOE 10>1002/adma.201104066 2011, IDS (Year: 2011).*
European communication dated Mar. 4, 2020 in corresponding European patent application No. 17836805.6.
Cao et al., "The Synergistic Effect of Hierarchical Assemblies of siRNA and Chemotherapeutic Drugs Co-delivered into Hepatic Cancer Cells", Biomaterials, vol. 32, pp. 2222-2232, 2010.
Wang et al., "Design of Multifunctional Micelle for Tumor-Targeted Intracellular Drug Release and Fluorescent Imaging", Advanced Materials, vol. 24, pp. 115-120, 2012.
Wang et al., "Supporting Information, Design of Multifunctional Micelle for Tumor-Targeted Intracellular Drug Release and Fluorescent Imaging", Advanced Materials, pp. 1-21, 2011.

(Continued)

*Primary Examiner* — Anna R Falkowitz
(74) *Attorney, Agent, or Firm* — Nields, Lemack & Frame, LLC

(57) ABSTRACT

Provided is a polymeric micelle type DDS preparation that may efficiently exhibit pharmacological activity effects by enhancing migration characteristics, penetrability, and retention characteristics toward a diseased target tissue such as a tumor tissue or an inflammation-affected tissue, and thereby enhancing the action of a pharmacologically active substance. Disclosed is a block copolymer (A) having a hydrophilic polymer segment linked to a hydrophobic polymer segment, the hydrophilic polymer segment containing a polyethylene glycol chain, and the hydrophobic polymer segment containing a polyamino acid chain having a hydrophobic substituent in a side chain, wherein the hydrophilic polymer segment has a target binding site bonded thereto, and the main chain polymer combining the polyethylene glycol chain and the polyamino acid chain has a molecular weight of not less than 2 kilodaltons and not more than 10 kilodaltons.

3 Claims, 7 Drawing Sheets

(56) References Cited

U.S. PATENT DOCUMENTS

| | | |
|---|---|---|
| 2014/0142167 A1 | 5/2014 | Shimizu et al. |
| 2015/0011715 A1 | 1/2015 | Nakamura et al. |
| 2015/0051347 A1 | 2/2015 | Kataoka et al. |
| 2015/0080454 A1 | 3/2015 | Kataoka et al. |
| 2015/0087788 A1 | 3/2015 | Docon et al. |
| 2015/0259479 A1 | 9/2015 | Shimizu et al. |
| 2015/0368401 A1 | 12/2015 | Sill et al. |
| 2016/0114058 A1 | 4/2016 | Kato et al. |
| 2016/0264732 A1 | 9/2016 | Sill et al. |
| 2016/0279164 A1 | 9/2016 | Nakamura et al. |
| 2017/0240703 A1 | 8/2017 | Sill et al. |
| 2017/0253699 A1 | 9/2017 | Sill et al. |

FOREIGN PATENT DOCUMENTS

| | | |
|---|---|---|
| CN | 101684178 A | 3/2010 |
| CN | 101831068 A | 9/2010 |
| CN | 101977631 A | 2/2011 |
| CN | 102552934 A | 7/2012 |
| CN | 103131005 A | 6/2013 |
| CN | 103374128 A | 10/2013 |
| CN | 104487481 A | 4/2015 |
| CN | 104856952 A | 8/2015 |
| CN | 105524271 A | 4/2016 |
| JP | 4538666 B2 | 9/2010 |
| TW | 200812572 A | 3/2008 |
| WO | 2004/039869 A1 | 5/2004 |
| WO | 2004/082718 A1 | 9/2004 |
| WO | 2006/033296 A1 | 3/2006 |
| WO | 2007/111211 A1 | 10/2007 |
| WO | 2008/041610 A1 | 4/2008 |
| WO | 2009/041570 A1 | 4/2009 |
| WO | 2010/013836 A1 | 2/2010 |
| WO | 2012/058552 A1 | 5/2012 |
| WO | 2013/060919 A1 | 5/2013 |
| WO | 2013/073697 A1 | 5/2013 |
| WO | 2013/162041 A1 | 10/2013 |
| WO | 2014/185504 A1 | 11/2014 |

OTHER PUBLICATIONS

International Search Report and Written Opinion dated Sep. 19, 2017 in corresponding PCT application No. PCT/JP2017/026788.

Cabral et al., "Systemic Targeting of Lymph Node Metastasis through the Blood Vascular System by Using Size-Controlled Nanocarriers", ACS Nano, (2015) vol. 9(5), p. 4957-4967.

Hamaguchi et al., "Phase I Study of NK012, a Novel SN-38—Incorporating Micellar Nanoparticle, in Adult Patients with Solid Tumors", Clinical Cancer Research, (2010) vol. 16, p. 5058-5066.

Matsumura, "Poly (amino acid) micelle nanocamers in preclinical and clinical studies", Advanced Drug Delivery Reviews, (2008) vol. 60, p. 899-914.

Prabhakar et al., "Challenges and Key Considerations of the Enhanced Permeability and Retention Effect for Nanomedicine Drug Delivery in Oncology", Cancer Research, (2013) vol. 73, p. 2412-2417.

Baba et al., "Treatment of neurological disorders by introducing mRNA in vivo using polyplex nanomicelles", Journal of Controlled Release, vol. 201, pp. 41-48, 2015.

Chinese communication, with English translation, dated Sep. 21, 2020 in corresponding Chinese patent application No. 201780046734.5.

Taiwanese communication, with English translation, dated Oct. 13, 2020 in corresponding Taiwanese patent application No. 106125716.

* cited by examiner

KIDNEY
(whole)

Tumor/Plasma ratio

(AUC$_{1-24}$ OF NON-POLYMER-BONDED 7-ETHYL-10-HYDROXYCAMPTOTHECIN)

ACTIVE-TARGETING-TYPE POLYMER DERIVATIVE, COMPOSITION CONTAINING SAID POLYMER DERIVATIVE, AND USES OF SAID POLYMER DERIVATIVE AND SAID COMPOSITION

TECHNICAL FIELD

The present invention relates to a polymer derivative having a target binding site, and a composition including the polymer derivative. More particularly, the invention relates to an active targeting type polymer derivative having migration characteristics, penetrability, and retention characteristics to and in a diseased target tissue and/or having excretability through the kidneys and the like, a composition including the polymer derivative, and pharmaceutical products using the polymer derivative and the composition.

RELATED ART

Development of drug delivery systems (DDS) that control the pharmacokinetics of a physiologically active substance, which is an active ingredient for a pharmaceutical product, and delivers the physiologically active substance to a specific site of action in vivo in a desired drug concentration-reaction time, is underway. Non Patent Literature 1 discloses a DDS preparation including a block copolymer in which a polyethylene glycol segment is linked to a hydrophobic polymer segment containing a polyamino acid chain, as a drug transport carrier. This block copolymer forms polymeric micelles having a particle size of 20 to 100 nm, each micelle having a polyethylene glycol outer shell and a hydrophobic inner core, and the polymeric micelles stably include various kinds of drugs in the inner core by means of chemical bonding or physical uptake.

This polymeric micelle type DDS preparation is characterized in that the DDS preparation has an EPR (a phenomenon in which particles having a particle size of 100 nm or less specifically collect in the blood vessels near a tumor site or an inflammation site, where permeability is high compared to normal blood vessels) effect; that excretion is suppressed when the DDS preparation is administered into the living body, and in vivo retention characteristics are enhanced; and that the DDS preparation passively migrates to and accumulates in tissues such as tumors. Based on these properties, a polymeric micelle type DDS preparation may keep a physiologically active substance in the living body for a long time and may thus increase the rate of utilization of the active ingredient. That is, a polymeric micelle type DDS preparation brings a more powerful physiological activity effect compared to the drug mounted therein.

Patent Literature 1 and Patent Literature 2 disclose polymeric micelle type DDS preparations, in which paclitaxel is physically incorporated. Patent Literature 3 describes a polymeric micelle type DDS preparation to which a camptothecin derivative is chemically bonded, and Patent Literature 4 describes a polymeric micelle type DDS preparation to which a resorcinol derivative is chemically bonded. Patent Literature 5 describes a polymeric micelle type DDS preparation to which a taxane derivative is chemically bonded, and Patent Literature 6 describes a polymeric micelle type DDS preparation to which a steroid derivative is chemically bonded. Various drugs may be applied to polymeric micelle type DDS preparations, and various block copolymers and polymeric micelle type DDS preparations are known.

Since conventional polymeric micelle type DDS preparations have enhanced retention characteristics in blood of the incorporated drug, the drug acts for a long time period not only on diseased tissues but also on normal tissues. For example, the block copolymer having a camptothecin derivative as an antitumor agent chemically bonded thereto as specified in Patent Literature 3, slowly releases the camptothecin derivative in vivo. As a result, there is a risk that the released camptothecin derivative may have action on tumor tissues as well as normal tissues such as bone marrow over a long time period. Conventional camptothecin derivative-bonded block copolymers exhibit strong antitumor effects and also inevitably exhibit bone marrow suppression such as neutropenia. This has caused dose limiting toxity (DLT) (Non Patent Literature 2). Therefore, there is a demand for the development of a camptothecin derivative exhibiting reduced bone marrow suppression while maintaining an antitumor effect. As such, conventional polymeric micelle type DDS preparations may exhibit powerful pharmacological activity effects; however, those DDS preparations may exhibit side effects in normal tissues.

Meanwhile, it is pointed out in Non Patent Literature 3 that the EPR effect varies depending on the cancer type and the animal type. Furthermore, it is contemplated that this difference may affect the effects of the components included in the polymeric micelle type DDS preparation. In Non Patent Literature 4, it is reported that there are animal models with which it is easy to show the EPR effect, and animal models with which it is difficult to show the EPR effect, by using polymeric micelle type DDS preparations having particle sizes of 30 nm and 70 nm, and that a polymeric micelle type DDS preparation having a particle size of 30 nm shows the effects of the DDS preparation in an animal model with low EPR effect.

Patent Literature 7 discloses a composition including a polymer component α having a target binding site and a polymer component β having a drug, specifically, a polymeric micelle type DDS preparation that uses transferrin as a target binding site and docetaxel as a drug. Together with powerful antitumor activity brought by the effect of targeting to a tumor tissue, a decrease in side effects caused by disintegration of micelles and subsequent excretion of polymer unit β out of the body induced by metabolism is described. However, since detailed side effect reducing effects are not described, the in vivo behavior of the composition is not traced, and the particle size is large, such as about 100 nm, in many Examples, it is considered that sufficient antitumor effects and side effect reduction may not be realized depending on the cancer type and the animal type.

From the above descriptions, there are demands for the development of a block copolymer that enhances the effect of a polymeric micelle type DDS preparation by having penetrability and retention characteristics for a diseased tissue in which the EPR effect is not easily exhibited, and that reduces side effects by suppressing the distribution of the polymeric micelle type DDS preparation in normal tissues; and a composition including the block copolymer.

PRIOR ART LITERATURE

Patent Literature

Patent Literature 1: WO 2004/082718 A
Patent Literature 2: WO 2006/033296 A
Patent Literature 3: WO 2004/039869 A
Patent Literature 4: WO 2008/041610 A Patent Literature 5: WO 2007/111211 A
Patent Literature 6: WO 2009/041570 A
Patent Literature 7: JP 4538666 B2

Non Patent Literature

Non Patent Literature 1: Advanced Drug Delivery Reviews, (2008) Vol. 60, p. 899-914
Non Patent Literature 2: Clinical Cancer Research, (2010) Vol. 16, p. 5058-5066
Non Patent Literature 3: Cancer Research, (2013) Vol. 73, p. 2412-2417
Non Patent Literature 4: ACS Nano, (2015) Vol. 9(5), p. 4957-4967

SUMMARY OF INVENTION

Technical Problem

An object of the present invention is to provide a block copolymer having enhanced effectiveness and/or safety compared to conventional polymeric micelle type DDS preparations including a physiologically active substance in the inner core by means of chemical bonding or physical uptake, and a pharmaceutical composition formed from the block copolymer. Particularly, it is an object of the invention to provide a polymeric micelle type DDS preparation that may efficiently exhibit pharmacological activity effects, by enhancing the migration characteristics, penetrability, and retention characteristics against a diseased target tissue such as a tumor tissue or an inflammation-affected tissue, and thereby enhancing the action of a pharmacologically active substance.

Solution to Problem

The inventors of the present invention conducted a thorough investigation in order to solve the problems described above, and as a result, the inventors found that a polymeric micelle type DDS preparation produced using a carrier polymer having a polymer main chain with a molecular weight of from 2 kilodaltons to 10 kilodaltons, exhibits pharmacokinetic characteristics that are completely different from those of conventional polymeric micelle type DDS preparations.

Furthermore, the inventors found that when a block copolymer in which a hydrophilic polymer segment containing a polyethylene glycol chain is linked to a hydrophobic polymer segment containing a polyamino acid chain having a hydrophobic substituent in a side chain, said block copolymer being a carrier polymer for producing a polymeric micelle type DDS preparation, is produced into a block copolymer having a target binding site, such as an antibody molecule or a receptor-binding peptide, bonded to the polyethylene glycol chain, the block copolymer forms polymeric micelle-like associates, and at the same time, the block copolymer has target site recognizability to thereby stay target site-specifically. The inventors also found that the block copolymer exhibits kinetics that may enhance effectiveness and/or safety. Thus, the inventors completed the present invention.

That is, the present invention relates to the following items [1] to [17].

[1] A block copolymer (A) including a hydrophilic polymer segment linked to a hydrophobic polymer segment, the hydrophilic polymer segment containing a polyethylene glycol chain, and the hydrophobic polymer segment containing a polyamino acid chain having a hydrophobic substituent in a side chain, wherein the hydrophilic polymer segment has a target binding site bonded thereto, and the main chain polymer combining the polyethylene glycol chain and the polyamino acid chain has a molecular weight of not less than 2 kilodaltons and not more than 10 kilodaltons.

A first feature of the present invention is that with regard to the block copolymer including a hydrophilic polymer segment linked to a hydrophobic polymer segment, which is used for producing a polymeric micelle type DDS preparation, the polymer main chain of the block copolymer is a carrier polymer having a molecular weight of not less than 2 kilodaltons and not more than 10 kilodaltons. In addition, a second feature of the invention is that the block copolymer is a block copolymer having a target binding site such as an antibody molecule or a receptor-binding peptide bonded to the hydrophilic polymer segment.

Due to the first feature, the present invention has migration characteristics and penetrability toward a target diseased tissue based on conventional polymeric micelle type DDS preparations, and also has pharmacokinetic characteristics that are different from those of conventional polymeric micelle type DDS preparations that have excretability through the kidneys. Furthermore, due to the second feature, the present invention has a targeting function for a target tissue and may stay in a target diseased tissue for a long time period.

[2] The block copolymer (A) according to the above-described item [1], wherein the polyamino acid chain is a polyaspartic acid chain, a polyglutamic acid chain, or a poly(aspartic acid-glutamic acid) chain, and has a hydrophobic substituent bonded to a side-chain carboxy group by an ester bond and/or an amide bond.

When a polyamino acid having a carboxylic acid side chain is used for the hydrophobic polymer segment, it is advantageous because the hydrophobic polymer segment may be easily provided with a variety of hydrophobic substituents with a controlled amount of bonding.

[3] The block copolymer (A) according to the above-described item [1] or [2], wherein the polyethylene glycol chain has a molecular weight of not less than 1 kilodalton and not more than 6 kilodaltons.

[4] The block copolymer (A) according to any one of the above-described items [1] to [3], wherein a mass content percentage of the hydrophobic substituent in the block copolymer excluding the target binding site is not less than 5% by mass and not more than 60% by mass.

[5] The block copolymer (A) according to any one of the above-described items [1] to [4], wherein the block copolymer (A) is represented by General Formula (1):

[Chemical Formula 1]

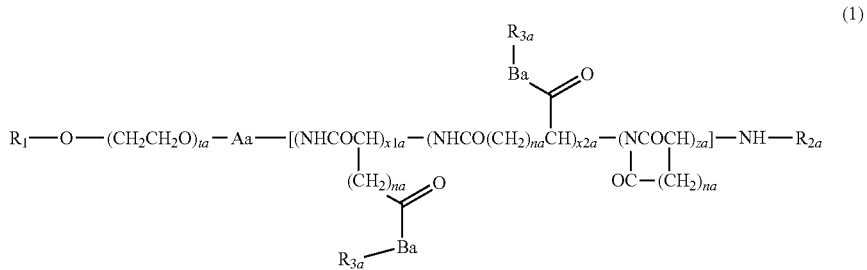

wherein $R_1$ represents a bonding residue of a target binding site; ta represents an integer from 20 to 140; Aa represents a (C1-C6) alkylene group which may have a substituent; $R_{2a}$ represents a substituent selected from the group consisting of a hydrogen atom, a (C1-C6) acyl group, and a (C1-C6) alkoxycarbonyl group; $R_{3a}$ includes one or more bonding residues of one or more hydrophobic substituents selected from the group consisting of a linear, branched or cyclic (C1-C30) alkoxy group which may have a substituent, a linear, branched or cyclic (C1-C30) alkylamino group which may have a substituent, a linear, branched or cyclic (C1-C30) dialkylamino group which may have a substituent, a (C1-C8) alkylaminocarbonyl-(C1-C8) alkylamino group which may have a substituent, a bonding residue of a physiologically active substance having a hydroxy group and/or an amino group, and a bonding residue of a fluorescent substance having a hydroxy group and/or an amino group, while the residual part is a hydroxy group; Ba represents a single bond or a divalent bonding group; na represents 1 or 2; x1a, x2a, and za each independently represent an integer from 0 to 20; x1a+x2a represents an integer from 1 to 20; (x1a+x2a+za) represents an integer from 3 to 20; and the various constituent units to which $R_{3a}$ is bonded, and a constituent unit formed by intramolecular cyclization of a side-chain carbonyl group constitute a structure with those constituent units being each independently randomly arranged.

[6] The block copolymer (A) according to any one of the above-described items [1] to [5], wherein the block copolymer (A) forms self-associating nanoparticles in an aqueous solution, and the nanoparticles have an average particle size of 30 nanometers or less.

The present invention has major features that the block copolymer (A) has self-associating properties based on being amphiphilic, forms nanoparticles having a particle size of 30 nanometers or less, has excellent penetrability to a diseased tissue as well as excretability through the kidneys and the like, and exhibits pharmacokinetic characteristics that are obviously different from the pharmacokinetic characteristics of conventionally known polymeric micelle type DDS preparations.

The present application also includes, as one of embodiments of the invention, a composition produced by combining the above-mentioned block copolymer (A) in which the main chain polymer having a target binding site has a molecular weight of from 2 kilodaltons to 10 kilodaltons, with a block copolymer (B) in which the main chain polymer not having a target binding site has a molecular weight of from 2 kilodaltons to 10 kilodaltons.

[7] A composition including a block copolymer (A) and a block copolymer (B), the block copolymer (A) being the block copolymer (A) according to any one of the above-described items [1] to [6], and the block copolymer (B) being a block copolymer (B) having a hydrophilic polymer segment containing a polyethylene glycol chain linked to a hydrophobic polymer segment containing a polyamino acid chain having a hydrophobic substituent in a side chain, wherein the main chain polymer combining a polyethylene glycol chain and a polyamino acid chain of the block copolymer (B) has a molecular weight of not less than 2 kilodaltons and not more than 10 kilodaltons, and a mass content percentage of the hydrophobic substituent of the block copolymer (B) is not less than 5% by mass and not more than 60% by mass.

When a block copolymer (A) having a target binding site and having an active targeting ability is combined with a block copolymer (B) that does not include a target binding site, these two kinds of copolymers form integrated associative aggregates based on interaction. Therefore, the affinity ability to a target disease may be regulated by regulating the content of the block copolymer (A) having active targeting action. Furthermore, the associative properties of the polymeric micelle-like associates may be regulated by providing the block copolymer (B) with various hydrophobic substituents.

[8] The composition according to the above-described item [7], wherein the polyamino acid chain of the block copolymer (B) is a polyaspartic acid chain, a polyglutamic acid chain, or a poly(aspartic acid-glutamic acid) chain, and the polyamino acid chain has the hydrophobic substituent bonded to a side-chain carboxy group by an ester bond and/or an amide bond.

[9] The composition according to item [7] or [8], wherein the polyethylene glycol chain of the block copolymer (B) has a molecular weight of not less than 1 kilodalton and not more than 6 kilodaltons.

[10] The composition according to any one of the above-described items [7] to [9], wherein the block copolymer (B) is represented by General Formula (2):

[Chemical Formula 2]

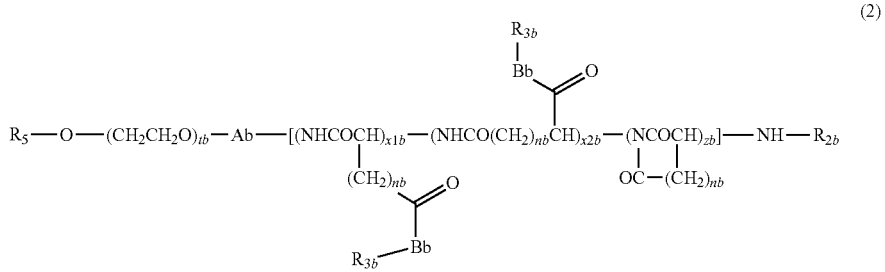

wherein $R_5$ represents a hydrogen atom or a (C1-C6) alkyl group which may have a substituent; tb represents an integer from 20 to 140; Ab represents a (C1-C6) alkylene group which may have a substituent; $R_{2b}$ represents a substituent selected from the group consisting of a hydrogen atom, a (C1-C6) acyl group, and a (C1-C6) alkoxycarbonyl group; $R_{3b}$ includes one or more bonding residues of one or more hydrophobic substituents selected from the group consisting of a linear, branched or cyclic (C1-C30) alkoxy group which may have a substituent, a linear, branched or cyclic (C1-C30) alkylamino group which may have a substituent, a linear, branched or cyclic (C1-C30) dialkylamino group which may have a substituent, a (C1-C8) alkylaminocarbonyl-(C1-C8) alkylamino group which may have a substituent, and a bonding residue of a fluorescent substance having a hydroxy group and/or an amino group, while the residual part is a hydroxy group; Bb represents a single bond or a divalent bonding group; nb represents 1 or 2; x1b, x2b, and zb each independently represent an integer from 0 to 20; x1b+x2b represents an integer from 1 to 20; (x1b+x2b+zb) represents an integer from 3 to 20; and the various constituent units to which $R_{3b}$ is bonded, and the constituent unit formed by intramolecular cyclization of a side-chain carbonyl group constitute a structure with those constituent units being each independently randomly arranged.

[11] The composition according to any one of the above-described items [7] to [10], wherein the composition including the block copolymer (A) and the block copolymer (B) forms nanoparticles in an aqueous solution, and the nanoparticles have an average particle size of 30 nanometers or less.

According to the present invention, the block copolymer (A) having an active targeting function and the block copolymer (B) that does not have an active targeting function associate as a result of interaction based on the fact that the two copolymers are both amphiphilic, and form integrated nanoparticles having a particle size of 30 nanometers or less. The nanoparticles have a major feature that the nanoparticles have excellent migration characteristics and penetrability toward a target tissue and also has excretability through the kidneys and the like, and the nanoparticles exhibit pharmacokinetic characteristics that are obviously different from those of conventionally known polymeric micelle type DDS preparations. Furthermore, the nanoparticles have a targeting function toward a target tissue due to the block copolymer (A) and are capable of staying in a target diseased tissue for a long time period.

The present application also includes, as one of embodiments of the invention, a composition produced by combining the above-mentioned block copolymer (A) in which the main chain polymer having a target binding site has a molecular weight of from 2 kilodaltons to 10 kilodaltons, with a block copolymer (C) having a polymeric prodrug element, in which the main chain polymer that does not have a target binding site has a molecular weight of from 2 kilodaltons to 10 kilodaltons, and a physiologically active substance is included by chemical bonding of a form that slowly cleaves the physiologically active substance.

[12] A composition including a block copolymer (A) and a block copolymer (C), the block copolymer (A) being the block copolymer (A) according to any one of the above-described items [1] to [6], and the block copolymer (C) being a block copolymer (C) having a hydrophilic polymer segment containing a polyethylene glycol chain linked to a hydrophobic polymer segment containing a polyamino acid chain with a physiologically active substance having a hydroxy group and/or an amino group bonded to a side-chain carboxy group, wherein the main chain polymer combining the polyethylene glycol chain and the polyamino acid chain of the block copolymer (C) has a molecular weight of not less than 2 kilodaltons and not more than 10 kilodaltons, and a mass content percentage of the physiologically active substance having a hydroxy group and/or an amino group of the block copolymer (C) is not less than 5' by mass and not more than 60% by mass.

When a block copolymer (A) having a target binding site and having an active targeting ability is combined with a block copolymer (C), which is a polymeric prodrug that does not include a target binding site, these two kinds of copolymers form integrated associative aggregates based on interaction. Therefore, the affinity ability to a target disease may be regulated by regulating the content of the block copolymer (A) having an active targeting action. Furthermore, by providing the block copolymer (C) with various physiologically active substances, a polymeric micelle type DDS preparation having an active targeting function to various diseases may be provided.

[13] The composition according to the above-described item [12], wherein the polyamino acid chain of the block copolymer (C) is a polyaspartic acid chain, a polyglutamic acid chain, or a poly(aspartic acid-glutamic acid) chain, and has a physiologically active substance having a hydroxy group and/or an amino group bonded to a side-chain carboxy group by an ester bond and/or an amide bond.

[14] The composition according to the above-described item [12] or [13], wherein the polyethylene glycol chain of the block copolymer (C) has a molecular weight of not less than 1 kilodalton and not more than 6 kilodaltons.

[15] The composition according to the above-described item [12] to [14], wherein the block copolymer (C) is represented by General Formula (3):

[Chemical Formula 3]

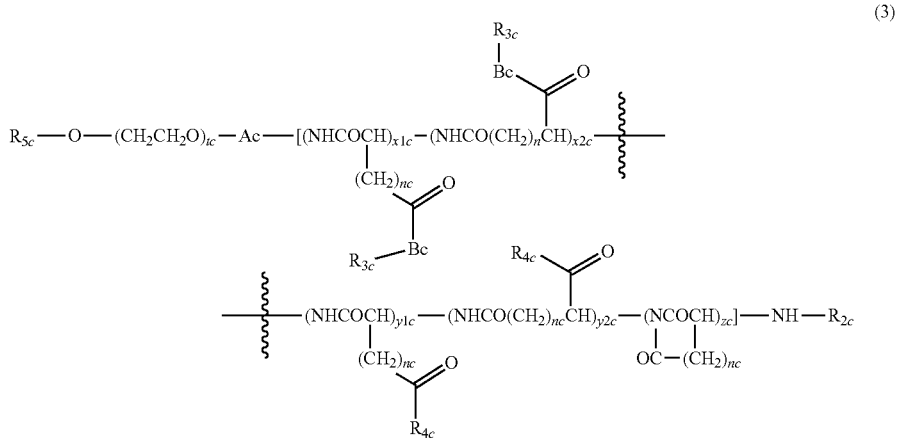

(3)

wherein $R_{5c}$ represents a hydrogen atom or a (C1-C6) alkyl group which may have a substituent; tc represents an integer from 20 to 140; Ac represents a (C1-C6) alkylene group which may have a substituent; $R_{2c}$ represents a substituent selected from the group consisting of a hydrogen atom, a (C1-C6) acyl group, and a (C1-C6) alkoxycarbonyl group; $R_{3c}$ represents a bonding residue of a physiologically active substance having a hydroxy group and/or an amino group; $R_4$, is a bonding residue of a hydrophobic substituent and represents one or more substituents selected from the group consisting of a linear, branched or cyclic (C1-C30) alkoxy group which may have a substituent, a linear, branched or cyclic (C1-C30) alkylamino group which may have a substituent, a linear, branched or cyclic (C1-C30) dialkylamino group which may have a substituent, a (C1-C8) alkylaminocarbonyl-(C1-C8) alkylamino group which may have a substituent, a bonding residue of a fluorescent substance having a hydroxy group and/or an amino group, and a hydroxy group; Bc represents a single bond or a divalent bonding group; nc represents 1 or 2; x1c, x2c, y1c, y2c, and zc each independently represent an integer from 0 to 20; (x1c+x2c) is an essential constituent and represents an integer from 1 to 20; (x1c+x2c+y1c+y2c+zc) represents an integer from 3 to 20; and the various constituent units to which $R_{3c}$ and $R_{4c}$ are bonded, and the constituent unit formed by intramolecular cyclization of a side-chain carbonyl group constitute a structure with those constituent units being each independently randomly arranged.

[16] The composition according to any one of the above-described items [12] to [15], wherein the composition including the block copolymer (A) and the block copolymer (C) forms nanoparticles in an aqueous solution, and the nanoparticles have an average particle size of 30 nanometers or less.

When a block copolymer (A) having a target binding site and having an active targeting ability is combined with a block copolymer (C), which is a polymeric prodrug that does not include a target binding site, these two kinds of copolymers form integrated associative aggregates based on interaction. Therefore, the affinity ability to a target disease may be regulated by regulating the content of the block copolymer (A) having active targeting action.

Furthermore, by providing the block copolymer (C) with various physiologically active substances, a polymeric micelle type DDS preparation that may be supplied to the treatment of various diseases may be provided.

Since the present block copolymer may be used for pharmaceutical products, the medicinal usage applications of the block copolymer are also included in the present invention.

[17] A medicine including the block copolymer according to any one of the above-described items [1] to [16].

That is, a medicine that uses the block copolymer (A) may be mentioned. A polymeric micelle type DDS preparation may be produced by physically incorporating a physiologically active substance into the block copolymer (A). Furthermore, a chemically bonded type polymeric micelle type DDS preparation may be produced by producing a prodrug type copolymer having a physiologically active substance bonded thereto as a hydrophobic substituent.

Furthermore, a medicine that uses a composition including a block copolymer (A) and a block copolymer (B) may be mentioned as the embodiment according to any one of the above-described items [7] to [11]. A polymeric micelle type DDS preparation may be produced by physically incorporating a physiologically active substance into the block copolymers (A) and (B). Furthermore, a chemically bonded type polymeric micelle type DDS preparation may be produced by producing a prodrug type copolymer having a physiologically active substance bonded as a hydrophobic substituent to the block copolymer (A).

Alternatively, a medicine that uses the composition including the block copolymer (A) and the block copolymer (C) as an embodiment according to any one of the above-described items [12] to [16] may be mentioned. A polymeric micelle type DDS preparation may be produced by physically incorporating a physiologically active substance into the block copolymers (A) and (C). Furthermore, a chemically bonded type polymeric micelle type DDS preparation may be produced by employing a prodrug type copolymer having a physiologically active substance bonded thereto as the hydrophobic substituent of the block copolymer (A).

Alternatively, a chemically bonded type polymeric micelle type DDS preparation may be produced by employing a hydrophobic substituent, which is not a physiologically active substance, as the hydrophobic substituent of the block copolymer (A), and employing the block copolymer (C) as a prodrug type copolymer.

Advantageous Effects of Invention

Nanoparticles formed from a composition including the block copolymer (A) of the present invention having a target binding site bonded thereto, after administered into the living body, exhibit enhanced migration, penetration, and retention to and in a target tissue, and/or enhanced excretability through the kidneys and the like. Therefore, a composition including the block copolymer (A) according to the present invention has high migration characteristics, penetrability, and retention characteristics toward a target tissue, compared to conventional polymeric micelle type DDS preparations, and accordingly, the composition may sensitize a physiologically active substance over a wide area of the target tissue and efficiently exhibit pharmacological activity effects.

Furthermore/alternatively, since the block copolymer and the composition have enhanced excretability through the kidneys and the like, the block copolymer and the composition exhibit suppressed retention in blood. Thus, the exhibition of disorders in normal tissues may be avoided by suppressing the sensitization of a physiologically active substance in normal tissue other than a target tissue.

Particularly, in the case of using an antitumor agent as a physiologically active substance, separation of the increase in the antitumor effect and/or the disorder in normal tissues, such as bone marrow suppression, may be achieved by enhancements of the migration characteristics, penetrability, and retention characteristics of a composition including the block copolymer (A) toward a tumor tissue, and/or enhancement of kidney excretability.

DESCRIPTION OF EMBODIMENTS

[Block Copolymer (A)]

Figure 1:
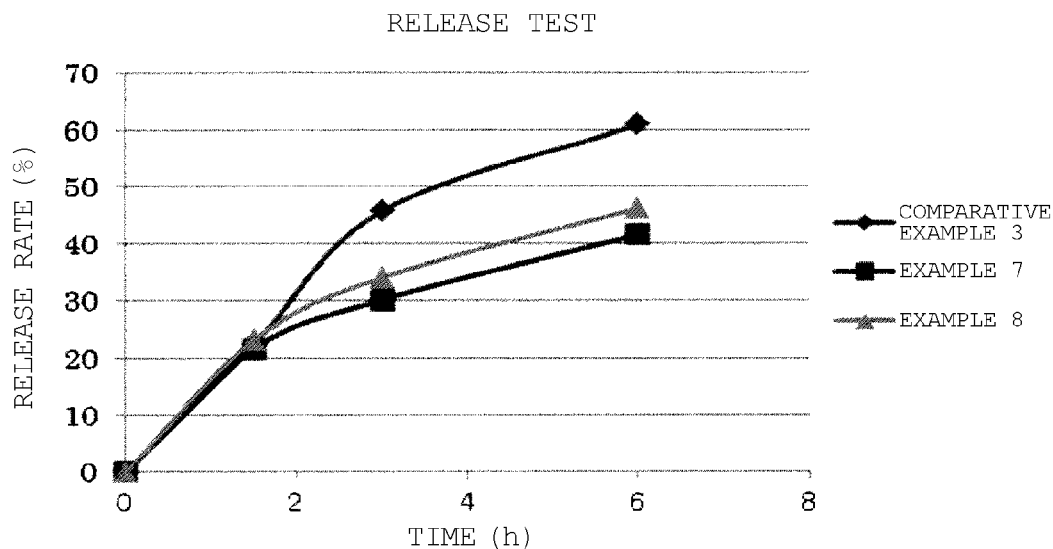
FIG. 1 shows drug release characteristics in a phosphate buffer solution in Examples 7 and 8 and Comparative Example 3.

The present invention relates to a block copolymer in which a hydrophilic polymer segment containing a polyethylene glycol chain is linked to a hydrophobic polymer segment containing a polyamino acid chain having a hydrophobic substituent in a side chain, and which serves as a constituent polymer for a polymeric micelle type DDS preparation. In this block copolymer, a target binding site is bonded to the hydrophilic polymer segment, and the main chain polymer combining the polyethylene glycol chain and the polyamino acid chain has a molecular weight of not less than 2 kilodaltons and not more than 10 kilodaltons. Preferably, the invention relates to a block copolymer (A) in which the mass content percentage of the hydrophobic substituent excluding the target binding site is not less than 5% by mass and not more than 50% by mass. The block copolymer (A) is an amphiphilic block copolymer having a target binding site showing affinity to a target diseased tissue or target cells, which may be a tumor tissue or an inflammatory disease site, and having a so-called active targeting function. The details of the block copolymer will be explained below.

The block copolymer (A) includes an AB block copolymer formed by connecting a hydrophilic polymer segment containing a polyethylene glycol chain with a hydrophobic polymer segment containing a polyamino acid chain having a hydrophobic substituent in a side chain, via an appropriate bonding group, as the main chain structure of the carrier polymer.

The hydrophilic polymer segment containing a polyethylene glycol chain in the block copolymer (A) is a segment having a repeating structure of an ethyleneoxy group: ($CH_2CH_2O$) unit. Preferably, the hydrophilic polymer segment is a segment structure containing a polyethylene glycol chain having a degree of polymerization of the ethyleneoxy group unit of 10 to 180 units, and more preferably a degree of polymerization of 20 to 140 units.

That is, the polyethylene glycol segment is preferably a segment part having a polyethylene glycol-equivalent molecular weight of 0.4 kilodaltons to 8 kilodaltons, more preferably a structural moiety having a molecular weight of 0.8 kilodaltons to 6 kilodaltons, and particularly preferably a structural moiety having a molecular weight of 1 kilodalton to 6 kilodaltons. A polyethylene glycol segment having a molecular weight of 1 kilodalton to 5 kilodaltons is especially preferable.

The mass content percentage of the polyethylene glycol segment in the block copolymer (A) excluding the target binding site is more preferably not less than 20% by mass and not more than 70% by mass, and especially preferably not less than 30% by mass and not more than 65% by mass.

Regarding the molecular weight of the polyethylene glycol segment used in the present invention, the molecular weight of the polyethylene glycol segment structural compound used at the time of producing the block copolymer of the invention, which is determined from the peak top molecular weight measured by a GPC method based on polyethylene glycol standards, is employed. Regarding the calculated value, a value rounded off to the nearest hundred is used.

One of the terminal groups of the polyethylene glycol segment is a linking group for bonding the polyamino acid chain that will be described below. The mode of linkage between the polyethylene glycol chain and the polyamino acid chain that will be described below is not particularly limited as long as a group that links two polymer chains by chemical bonding, and any linking group including functional groups capable of being respectively bonded to a polyethylene glycol terminal group and a terminal group of a polyamino acid derivative, may be used. Preferably, the linking group is a (C1-C6) alkylene group having a bondable functional group as a terminal group. The mode of linkage to a polyethylene glycol segment is preferably an ether bond formed by a terminal oxygen atom of a polyoxyethylene group: ($CH_2CH_2O$), and the mode of linkage to a hydrophobic polymer segment containing a polyamino acid chain is preferably an amide bond or an ester bond. That is, the linking group is a —($CH_2$)s-NH— group (wherein s is an integer from 1 to 6), or a —($CH_2$)s-CO— group (wherein s is an integer from 1 to 6). Examples of the —($CH_2$)s-CO— group (wherein s is an integer from 1 to 6) include a methylene carbonyl group, an ethylene carbonyl group, a trimethylene carbonyl group, a butylene carbonyl group, and a hexamethylene carbonyl group, and a trimethylene carbonyl group is particularly preferred.

Regarding the hydrophobic polymer segment containing a polyamino acid chain as the hydrophobic polymer segment of the block copolymer (A), any polymer segment that contains an amino acid having a hydrophobic substituent such as an alkyl group or an aralkyl group in a side chain and exhibits hydrophobicity compared to the hydrophilic polymer segment containing a polyethylene glycol chain, may be applied without any particular limitations.

The amino acids that constitute the polyamino acid segment are not particularly limited, and any of naturally occurring amino acids, synthetic amino acids, and side-chain modification products thereof may be used. Furthermore, any of the L-form, the D-form, and the racemates may be used. Examples thereof include glycine, alanine, β-alanine, leucine, phenylalanine, serine, threonine, tyrosine, aspartic acid, glutamic acid, lysine, arginine, histidine, ornithine, and cysteine. Furthermore, amino acids having modified side chains may also be used, and examples include an alkyl ester of aspartic acid or glutamic acid, an aralkyl ester of aspartic acid or glutamic acid, an alkylamide of aspartic acid or glutamic acid, an aralkylamide of aspartic acid or glutamic acid, and an alkyloxycarbonyl lysine such as Boc-lysine. The polyamino acid segment may be formed from any one kind of these amino acids, or a mixture of a plurality of kinds of amino acids may construct the segment.

It is preferable that the polyamino acid chain has a segment structure in which 2 to 30 units of amino acids are polymerized. A polymer of 3 to 20 units is more preferred, and a polymer of 5 to 20 units is especially preferred.

Regarding the polyamino acid chain in the hydrophobic polymer segment, it is preferable to use a polyamino acid chain containing aspartic acid and/or glutamic acid, which are amino acids having a carboxylic acid side chain, from the viewpoint that various hydrophobic substituents may be introduced into the amino acids in a well-controlled manner. More preferably, a polyaspartic acid chain constructed only from aspartic acid, a polyglutamic acid chain constructed only from glutamic acid, or a poly(aspartic acid-glutamic acid) chain formed from a random arrangement of aspartic acid and glutamic acid, is preferred. Further, an embodiment in which a hydrophobic substituent has been introduced into a side-chain carboxy group by an ester bond and/or an amide bond at an arbitrary proportion to the extent that shows desired hydrophobicity, is preferred. Such a polyamino acid chain having a side-chain carboxy group may be an α-amide bond type polymer, an amide bond type polymer having a side-chain carboxy group bonded thereto by an amide bond, a β- (or γ-) amide bond type polymer, or a mixture thereof. Furthermore, the polyamino acid chain may be a linear polyamino acid, or a branched type structure having side chains.

The hydrophobic substituent in the hydrophobic polymer segment is preferably one or more substituents selected from the group consisting of, for example, a (C1-C30) alkoxy group which may have a substituent, a (C1-C30) alkylamino group which may have a substituent, a di(C1-C30) alkylamino group which may have a substituent, and a (C1-C8) alkylaminocarbonyl-(C1-C8) alkylamino group which may have a substituent. It is preferable that these hydrophobic substituents are included in the block copolymer (A) excluding the target binding site at a percentage content of not less than 5% by mass and not more than 60% by mass. When the percentage content of the hydrophobic substituent is lower than 5% by mass, the hydrophobic polymer segment of the block copolymer (A) has weak hydrophobicity, and there is a risk that sufficient associative properties based on hydrophobic interaction may not be obtained. On the other hand, when the percentage content of the hydrophobic substituent is more than 60% by mass, the block copolymer (A) has sufficient associative properties; however, there is a risk that the block copolymer (A) may not provide satisfactory pharmacokinetic characteristics with regard to the penetrability to a diseased tissue, the distribution characteristics, and excretability out of the body. It is preferable that the percentage content of the hydrophobic substituent in the block copolymer (A) is not less than 5% by mass and not more than 50% by mass.

The (C1-C30) alkoxy group which may have a substituent as the hydrophobic substituent for the hydrophobic polymer segment may be a linear, branched or cyclic (C1-C30) alkoxy group which may have a substituent, that is, the side-chain carboxy group thereof is an ester type derivative. Such substituent may include a hydroxy group, a halogeno group, an amino group, an alkylamino group, a dialkylamino group, an alkoxy group, an aryl group, or the like. Examples of the (C1-C30) alkoxy group include a methoxy group, an ethoxy group, a propoxy group, an isopropoxy group, a butoxy group, a t-butoxy group, a cyclohexyloxy group, a benzyloxy group, a 4-phenylbutoxy group, an octyloxy group, a decyloxy group, a dodecyloxy group, a tetradecyloxy group, a hexadecyloxy group, an octadecyloxy group, an eicosyloxy group, a docosyloxy group, a tetracosyloxy group, a hexacosyloxy group, an octacosyloxy group, and a triacontyloxy group.

The (C1-C30) alkylamino group which may have a substituent may be a linear, branched or cyclic (C1-C30) alkylamino group which may have a substituent, that is, the side-chain carboxy group thereof is an alkylamide type derivative. Such substituent may include a hydroxy group, a halogeno group, an amino group, an alkylamino group, a dialkylamino group, an alkoxy group, an aryl group, or the like. Examples of the (C1-C30) alkylamino group include a methylamino group, an ethylamino group, a propylamino group, an isopropylamino group, a butylamino group, a t-butylamino group, a cyclohexylamino group, a benzylamino group, a 4-phenylbutylamino group, an octylamino group, a decylamino group, a dodecylamino group, a tetradecylamino group, a hexadecylamino group, an octadecylamino group, an eicosylamino group, a docosylamino group, a tetracosylamino group, a hexacosylamino group, an octacosylamino group, and a triacontylamino group.

The alkylamino group also includes an amino acid having a protected carboxy group, or a bonding residue of a fluorescent substance having an amino group. Such amino acid having a protected carboxy group includes glycine methyl ester, glycine benzyl ester, β-alanine methyl ester, β-alanine benzyl ester, alanine methyl ester, leucine methyl ester, or phenylalanine methyl ester may also be used.

Examples of the fluorescent substance having an amino group include 2-(2-aminoethoxy)-9-(diethylamino)-5H-benzo[a]phenoxazin-5-one, BODIPY (registered trademark) TR Cadaverine, BODIPY (registered trademark) FL Ethylenediamine, ALEXA FLUOR (registered trademark) 594 Cadaverine, TEXAS RED (registered trademark) Cadaverine, and ATTO 594 amine. Amide bonding residues of these are also included. By introducing a fluorescent substance, the fluorescent substance may be used as an indicator for checking the tissue distribution or excretability of the block copolymer (A).

The di(C1-C30) alkylamino group which may have a substituent may be a linear, branched or cyclic di(C1-C30) alkylamino group which may have a substituent, that is, the side-chain carboxy group thereof is a dialkylamide type derivative. Such substituent may include a hydroxy group, a halogeno group, an amino group, an alkylamino group, a dialkylamino group, an alkoxy group, an aryl group, or the like. Examples of the di(C1-C30) alkylamino group include a dimethylamino group, a diethylamino group, a dipropylamino group, a diisopropylamino group, a dibutylamino group, a pyrrolidino group, a piperidino group, a dibenzylamino group, a N-benzyl-N-methylamino group, a dioctylamino group, a dinonylamino group, a didecylamino group, a didodecylamino group, a ditetradecylamino group, a dihexadecylamino group, a dioctadecylamino group, and a dieicosylamino group.

The (C1-C8) alkylaminocarbonyl-(C1-C8) alkylamino group which may have a substituent is a urea type derivative substituted with a linear, branched or cyclic (C1-C8) alkyl group which may have a substituent. The alkyl groups may be the same as, or different from one another. Such substituent may include a hydroxy group, a halogeno group, an amino group, an alkylamino group, a dialkylamino group, an alkoxy group, an aryl group, or the like. In the case of having a substituent, a dialkylamino group is preferred. Examples of the (C1-C8) alkylaminocarbonyl-(C1-C8) alkylamino group which may have a substituent include a methylaminocarbonylmethylamino group, an ethylaminocarbonylethylamino group, an isopropylaminocarbonylisopropylamino group, a cyclohexylaminocarbonylcyclohexylamino group, an ethylaminocarbonyl(3-dimethylaminopropyl)amino group, and a (3-dimethylaminopropyl)aminocarbonylethylamino group.

Furthermore, a physiologically active substance having a hydroxy group and/or an amino group may also be used as the hydrophobic substituent. In a case in which the physiologically active substance is releasable, the block copolymer (A) may become a polymeric prodrug having an active targeting function.

The physiologically active substance that may be used as a hydrophobic substituent is not particularly limited; however, when the diseases to which a polymeric micelle type DDS preparation is applicable are considered, examples include malignant tumor diseases, inflammatory diseases, and infectious diseases. Thus, it is preferable to apply an active ingredient of a pharmaceutical product or a pharmaceutically active ingredient candidate compound, which are used for the treatment of these diseases, or to apply an active ingredient obtained by converting the aforementioned compound into a derivative or a prodrug. In the following description, examples of a physiologically active substance that are applicable to the invention will be listed; however, the examples are not limited to these.

Examples of a physiologically active substance that is used for malignant tumor diseases include camptothecin derivatives such as 7-ethyl-10-hydroxycamptothecin, irinotecan, nogitecan, and 9-aminocamptothecin; taxane derivatives such as paclitaxel, docetaxel, and cabazitaxel; resorcinol derivatives having HSP90 inhibitory activity, such as ganetespib and luminespib; anthracycline derivatives such as doxorubicin, epirubicin, amrubicin, daunorubicin, idarubicin, and pirarubicin; ramapycin derivatives such as sirolimus, everolimus, and temsirolimus; cytidine-based antimetabolites such as gemcitabine, cytosine arabinoside, enocitabine, cytarabine ocfosfate, ethynylcytidine, azacitidine, and decitabine; folic acid antimetabolites such as methotrexate, pemetrexed, levofolinate, and folinate; purine-based antimetabolites such as fludarabine, nelarabine, pentostatin, and cladribine; pyrimidine fluoride-based antimetabolites such as doxifluridine, capecitabine, tefugar, fluorouracil, and carmofur; platinum-containing compounds such as cisplatin, carboplatin, oxaliplatin, and nedaplatin; mitomycin derivatives such as mitomycin C; bleomycin derivatives such as bleomycin and libromycin; vinca alkaloid derivatives such as vincristine, vinblastine, vindesine, and vinorelbine; podophyllotoxin derivatives such as etoposide and teniposide; halichondrin derivatives such as eribulin; staurosporine derivatives such as rebeccamycin and UCN-01; thalidomide derivatives such as lenalidomide and pomalidomide; vitamin A derivatives such as tretinoin and tamibarotene; proteasome inhibitors such as bortezomib, carfilzomib, and ixazomib; combretastatin derivatives such as combretastatin A4; MEK inhibitors such as binimetinib, cobimetinib, and trametinib; CDK inhibitors such as dinaciclib, flavopiridol, and palbociclib; Raf kinase inhibitors such as dabrafenib, sorafenib, and vemurafenib; HDAC inhibitors such as vorinostat, belinostat, panabinostat, and romidepsin; actin polymerization inhibitors such as cytochalasin, latrunculin, and phalloidin; PARP inhibitors such as veliparib, rucaparib, and olaparib; tyrosine kinase inhibitors such as crizotinib, imatinib, gefitinib, erlotinib, apatinib, dasatinib, bosutinib, vandetanib, sunitinib, axitinib, pazopanib, lenvatinib, lapatinib, nintedanib, nilotinib, ceritinib, alectinib, ruxolitinib, crizotinib, and ibrutinib; nitrogen mustard-based alkylating agents such as bendamustine, cyclophosphamide, ifosfamide, bulusfan, melphalan; nitrosourea-based alkylating agents such as nimustine, ranimustine, and lomustine; alkylating agents such as dacarbazine, temozolomide, procarbazine, and thiotepa; aromatase inhibitors such as anastrozole, exemestane, letrozole, and fadrozole; anti-androgenic agents such as hydroxyflutamide, flutamide, bicalutamide, and enzaltamide; CYP17 (lyase) inhibitors such as abiraterone; anti-estrogenic agents such as tamoxifen and toremifene; and hormonal agents such as estramustine, progesterone, mitotane, and medroxyprogesterone.

Examples of a physiologically active substance that is used for inflammatory diseases include tacrolimus derivatives such as tacrolimus; steroid derivatives such as dexamethasone and prednisolone; ramapycin derivatives such as sirolimus, everolimus, and temsirolimus; immunosuppressants such as cyclosporine, fingolimod, azathioprine, mizoribine, myrcophenolate mofetil, and gusperimus; and NSAIDs such as diflunisal and tiaramide.

Examples of the physiologically active substance that is used for infectious diseases include antifungal agents, such as polyene-based antibiotic substances such as amphotericin B and nystatin, azole-based derivatives such as fluconazole and voriconazole, candin-based derivatives such as micafungin, and pyrimidine derivatives such as flucytosine; antiviral agents such as acyclovir, valacyclovir, and ganciclovir; and antiviral agents such as zanamivir, oseltamivir, and laninamivir and the like.

The ester derivatives and/or amide derivatives of aspartic acid and/or polyglutamic acid may be of the same kind, or a mixture of different kinds. Furthermore, it is acceptable that the form of free acid and salts thereof exist in a mixture.

One terminal group of the polyamino acid chain is a linking group to be bonded to the polyethylene glycol segment described above. The other terminal group is the N-terminal group or the C-terminal group of the polyamino acid chain, and this terminal group may be an unprotected free amino group, a free carboxylic acid, or a salt thereof, or may be an appropriate modification product of the N-terminal group or the C-terminal group.

Examples of the modification product of the N-terminal group include an acylamide type modification product, an alkoxycarbonylamide type modification product (urethane type modification product), and an alkylaminocarbonylamide type modification product (urea type modification product). Meanwhile, examples of the modification product of the C-terminal group include an ester type modification product, an amide type modification product, and a thioester type modification product.

The modifying group for the N-terminal group and the C-terminal group may be any arbitrary modifying group, and preferred examples include terminal modifying groups such as a linear, branched or cyclic (C1-C6) alkyl group which may have a substituent, a (C6-C18) aromatic group which may have a substituent, and a (C7-C20) aralkyl group which may have a substituent, all of which are to be bonded to the N-terminal group and the C-terminal group via an appropriate bonding group.

That is, the N-terminal group is preferably an appropriate acylamide type modification product or alkoxycarbonylamide type modification product (urethane type modification product), and is preferably a linear, branched or cyclic (C1-C6) alkyl group which may have a substituent, a (C6-C18) aromatic group which may have a substituent, or a (C7-C20) aralkyl group which may have a substituent as described above, all of them being linked via a carbonyl group or a carbonyloxy group.

Meanwhile, the C-terminal group is preferably an appropriate amide type substituent or ester type substituent, and is preferably a linear, branched or cyclic (C1-C8) alkyl group which may have a substituent, a (C6-C18) aromatic group which may have a substituent, or a (C7-C20) aralkyl group which may have a substituent, all of them being linked via an amide group or an ester group.

Examples of the linear, branched or cyclic (C1-C6) alkyl group which may have a substituent in connection with the terminal group include a methyl group, an ethyl group, an n-propyl group, an isopropyl group, an n-butyl group, a t-butyl group, and a cyclohexyl group.

Examples of the (C6-C18) aromatic group which may have a substituent in connection in the terminal group include a phenyl group, a pyridyl group, and a naphthyl group.

The (C7-C20) aralkyl group which may have a substituent in connection in the terminal group is a linear or branched alkyl group in which a hydrogen atom at any one site has been substituted by an aryl group. Examples thereof include a benzyl group, a 2-phenylethyl group, a 4-phenylbutyl group, and an 8-phenyloctyl group.

The terminal group of the polyamino acid chain is preferably a modification product involving the N-terminal group or the C-terminal group.

The target binding site that is bonded to the polyethylene glycol chain in the block copolymer (A) means a site having a biological recognition function, that is, a target-binding molecular species capable of selectively binding to a specific substance derived from a living organism, a virus, or the like and forming a biological coupled pair with the substance. Examples of a substance equivalent to the substance derived from a living organism or a virus include molecules existing in biological cells, bacteria, fungi, and viruses. Specific examples include tumor cells, neovascular cells, cells that constitute various organs, vascular endothelial cells, immunocompetent cells (for example, T-cells), and inflammatory cells (for example, white blood cells). Thus, the target binding site is a compound such as a protein, a peptide, or a sugar chain, which forms a coupled pair with a substance specific to these cells, or a compound configured to include at least a portion of the structure of the protein, peptide, or sugar chain while maintaining the specificity for forming a coupled pair.

Examples of the molecular species corresponding to the target binding site include a protein, a peptide, and a sugar chain, all of which form a coupled pair with a substance derived from a living organism or a virus. Examples of such a protein include an antibody that binds to a substance derived from a living organism or a virus, a fragment of the antibody, transferrin, and an epidermal growth factor (EGF). Examples of the antibody include antibodies that recognize antigens, including EGFR, Her2, CD20, VEGFR, CD20, and CD33, which are receptors highly expressed at the surface of objects of medication, represented by cancer cells, or antigens at the cell surface. The antibody may be a mononal antibody or a polyclonal antibody. The fragment of the antibody may be any fragment having a length that is capable of specifically recognizing an antibody, and examples include (Fab')2 and Fab. Examples of the peptide include insulin, LHRH, IGF, GE11, RGD peptide, and derivatives thereof. Examples of the sugar include sugars having glucose, mannose, galactose, and fucose residues. The compound having a target binding site may be a compound that may itself exhibit pharmacological activity, for example, an antibody medicine or a vaccine.

The mode of bonding between the polyethylene glycol segment and the target binding site is not particularly limited as long as a group that links the two by chemical bonding is used. The group may be a linking group including functional groups capable of bonding to a polyethylene glycol terminal group and to a bonding site of a chemical species as a target binding site, respectively. Preferably, the group is a (C1-C6) alkylene group having a bondable functional group as terminal groups. The mode of bonding to the polyethylene glycol segment is preferably an ether bond formed by a terminal oxygen atom of a polyoxyethylene group: $(CH_2CH_2O)$, and the α-terminal of the polyethylene glycol chain segment is preferably a hydroxy group, an amino group, a formyl group, a carboxy group, an aldehyde group, a mercapto group, or a maleimide group.

The molecular weight of the main chain polymer combining the polyethylene glycol chain and the polyamino acid chain of the block copolymer (A) is not less than 2 kilodaltons and not more than 10 kilodaltons. It is preferable that the molecular weight is not less than 2 kilodaltons and not more than 8 kilodaltons.

For this molecular weight, a calculated value obtained by summing the respective constituent molecular weights of the constituent moieties is employed. That is, a calculated value obtained by summing the (1) molecular weight of the polyethylene glycol chain and the (2) molecular weight of the main chain portion of the polyamino acid chain, is employed as the molecular weight. Meanwhile, since the target binding site for the block copolymer (A) is not included in the main chain polymer, the target binding site is not considered into the calculation of the molecular weight.

Meanwhile, the molecular weight of the main chain polymer combining the polyethylene glycol chain and the polyamino acid chain may be described with accuracy to the nearest kilodalton unit. In the following description, a preferred analysis method for the various constituent moieties will be described; however, any analysis method with sufficient accuracy for the measurement of the molecular weight of the polyamino acid derivative to the nearest kDa unit may be used without any particular limitations.

The (1) molecular weight of the polyethylene glycol chain is a measured value of the molecular weight of the polyethylene glycol compound that constructs the polyethylene glycol segment. The molecular weight that may be determined from the peak top molecular weight measured by a GPC method based on polyethylene glycol standards is employed. Regarding the calculated value, a value rounded off to the nearest hundred is used.

The (2) molecular weight of the main chain portion of the polyamino acid is a calculated value obtained by multiplying the molecular weight of a polymerization monomer unit of the polyamino acid chain included in the hydrophobic polymer segment by the average number of polymerizations. Regarding the number of polymerizations, a number of polymerizations calculated by a method of quantitatively determining the amount of side-chain carboxy groups of the polyamino acid by neutralization titration, or calculated from the integral values of $^1$H-NMR, may be used. It is preferable to use a neutralization titration method.

The block copolymer (A) of the invention shows self-associating properties in an aqueous solution, and the particle size (average particle size) is preferably 30 nm or less, and more preferably not less than 3 nm and not more than 30 nm.

The particle size (volume-based particle size) of the block copolymer (A) of the invention is measured from a 1 mg/mL aqueous solution of the block copolymer (A) of the invention by a dynamic light scattering method using laser light. For example, the particle size may be measured with a particle size/zeta potential measuring apparatus, Zetasizer Nano ZS, manufactured by Malvern Panalytical, Ltd. The volume-based particle size at this time is the particle size of the peak that exists at the largest proportion in a volume distribution analyzed by an NNLS method.

Since the block copolymer (A) of the invention is a block copolymer in which a hydrophilic polyethylene glycol segment is linked to a polyamino acid derivative segment showing hydrophobicity due to a physiologically active substance or another hydrophobic side chain, it is considered that the polyamino acid derivative segments of a plurality of block copolymer molecules will associate with one another in an aqueous solution based on hydrophobic interaction. As a result, it is speculated that the block copolymer forms micelle-like associates having a core-shell structure, in which the polyamino acid derivative segment forms the inner core (core part), and the hydrophilic polyethylene glycol segment covers the periphery of the inner core and forms an outer shell layer (shell part), and these micelle-like associates are observed as the nanoparticles described above.

The block copolymer (A) of the present invention is preferably a block copolymer represented by General Formula (1):

[Chemical Formula 4]

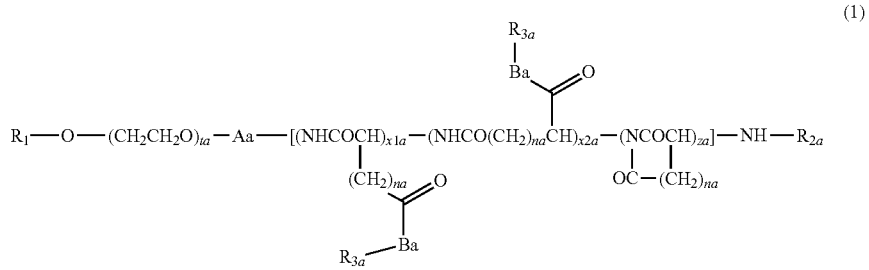

(1)

wherein $R_1$ represents a bonding residue of a target binding site; ta represents an integer from 20 to 140; Aa represents a (C1-C6) alkylene group which may have a substituent; $R_{2a}$ represents a substituent selected from the group consisting of a hydrogen atom, a (C1-C6) acyl group, and a (C1-C6) alkoxycarbonyl group; $R_{3a}$ includes one or more bonding residues of one or more hydrophobic substituents selected from the group consisting of a linear, branched or cyclic (C1-C30) alkoxy group which may have a substituent, a linear, branched or cyclic (C1-C30) alkylamino group which may have a substituent, a linear, branched or cyclic (C1-C30) dialkylamino group which may be substituted, a (C1-C8) alkylaminocarbonyl-(C1-C8) alkylamino group which may have a substituent, a bonding residue of a physiologically active substance having a hydroxy group and/or an amino group, and a bonding residue of a fluorescent substance having a hydroxy group and/or an amino group, while the remaining part is a hydroxy group; Ba represents a single bond or a divalent bonding group; na represents 1 or 2; x1a, x2a, and za each independently represent an integer from 0 to 20; x1a+x2a represents an integer from 1 to 20; (x1a+x2a+za) represents an integer from 3 to 20; and the various constituent units to which $R_{3a}$ is bonded, and the constituent unit formed by intramolecular cyclization of a side-chain carbonyl group constitute a structure with those constituent units being each independently randomly arranged.

The target binding site for R is formed by bonding to the terminal on the hydrophilic polyethylene glycol segment side via any arbitrary linking group. The compound having the target binding site has the same meaning as described above, and the compound may be a protein, a peptide, or a sugar chain, all of which form a coupled pair with a substance derived from a living organism or a virus. Examples of such a protein include an antibody that binds to a substance derived from a living organism or a virus, a fragment of the antibody, transferrin, and an epidermal growth factor (EGF). Examples of the antibody include antibodies that recognize antigens, including EGFR, Her2, CD20, VEGFR and CD33, which are receptors highly expressed at the surface of objects of medication, represented by cancer cells, or antigens at the cell surface. The antibody may be a monoclonal antibody or a polyclonal antibody. The fragment of the antibody may be any fragment having a length that is capable of specifically recognizing an antibody, and examples include (Fab')2 and Fab. Examples of the peptide include insulin, LHRH, IGF, GE11, RGD peptide, and derivatives thereof. Examples of the sugar include sugars having glucose, mannose, galactose, and fucose residues. The compound having a target binding site may be a compound that may itself exhibit pharmacological activity, for example, an antibody medicine or a vaccine.

For $R_1$, any arbitrary compound may be selected as appropriate according to the target tissue for the object disease of treatment or according to the purpose.

Regarding the block copolymer (A) represented by General Formula (1), a block copolymer having a linking group having a hydroxy group, an amino group, a formyl group, a carboxy group, an aldehyde group, a mercapto group, or a maleimide group at the α-terminal of a polyethylene glycol chain segment may be produced, and then $R_1$ may be bonded to the block copolymer by subjecting the block copolymer to a condensation or addition reaction with a compound having a target binding site.

ta in General Formula (1) represents the number of polymerizations of an ethyleneoxy group in the polyethylene glycol segment. This ta is an integer from 20 to 140. That is, the molecular weight of the polyethylene glycol segment is 0.8 kilodaltons to 6 kilodaltons.

When this ta is smaller than 20, there is a risk that the block copolymer (A) may not have sufficient water-solubility and may not exhibit desired disposition. Meanwhile, when this ta is larger than 140, since the content of the hydrophobic polymer segment containing a polyamino acid chain that bears hydrophobicity is relatively decreased, desired self-associating properties are not obtained, and there is a risk that the block copolymer may not exhibit the disposition associated with these self-associating properties. This ta is preferably an integer from 22 to 130, and more preferably an integer from 30 to 120. That is, the molecular weight of the polyethylene glycol segment is preferably 1 kilodalton to 5.7 kilodaltons, and more preferably 1.3 kilodaltons to 5.3 kilodaltons.

Examples of the (C1-C6) alkylene group which may have a substituent in connection with Aa include a methylene group, an ethylene group, an n-propylene group, and an n-butylene group. The substituent that may be carried by the (C1-C6) alkylene group may include a hydroxy group, a halogeno group, an amino group, an alkylamino group, a dialkylamino group, an alkoxy group, an aryl group, or the like.

This Aa is more preferably an ethylene group or an n-propylene group in particular.

The (C1-C6) acyl group which may have a substituent in connection with $R_{2a}$ may be a linear, branched or cyclic (C1-C6) acyl group which may have a substituent. Such substituent may include a hydroxy group, a halogeno group, an amino group, an alkylamino group, a dialkylamino group, an alkoxy group, an aryl group, or the like.

Examples of the (C1-C6) acyl group for $R_{2a}$ include a formyl group, an acetyl group, a trichloroacetyl group, a trifluoroacetyl group, a propionyl group, a pivaloyl group, a benzylcarbonyl group, and a phenethylcarbonyl group. A linear, branched or cyclic (C1-C4) acyl group which may have a substituent is more preferred, and an acetyl group, a trichloroacetyl group, and a trifluoroacetyl group are more preferred.

The (C1-C6) alkoxycarbonyl group which may have a substituent in connection with $R_{2a}$ may be a linear, branched or cyclic (C1-C6) alkoxycarbonyl group which may have a substituent. Such substituent may include a hydroxy group, a halogeno group, an amino group, an alkylamino group, a dialkylamino group, an alkoxy group, an aryl group, or the like. Examples of the (C1-C6) alkoxycarbonyl group for $R_2$ include a methoxycarbonyl group, an ethoxycarbonyl group, a t-butoxycarbonyl group, a benzyloxycarbonyl group, and a 9-fluorenylmethyloxycarbonyl group.

In General Formula (1), na represents 1 or 2. When na is 1, the amino acid that constitutes the polyamino acid chain is aspartic acid. Meanwhile, when na is 2, the amino acid that constitutes the polyamino acid chain is glutamic acid. Therefore, the polyamino acid chain in General Formula (1) is a polyaspartic acid chain, a polyglutamic acid chain, or a mixed chain of poly(aspartic acid-glutamic acid).

Ba in General Formula (1) is a bonding residue of the hydrophobic substituent related to $R_{3a}$, and is a bonding group between a side-chain carboxy group of an aspartic acid unit and/or a glutamic acid unit and one or more substituents selected from the group consisting of a linear, branched or cyclic (C1-C30) alkoxy group which may have a substituent, a linear, branched or cyclic (C1-C30) alkylamino group which may have a substituent, a linear, branched or cyclic (C1-C30) dialkylamino group which may have a substituent, a bonding residue of a physiologically active substance having a hydroxy group and/or an amino group, a bonding residue of a fluorescent substance, and a hydroxy group.

The boding group related to this Ba is a single bond or a divalent bonding group. The divalent bonding group is a bonding group that is bonded to a hydroxy group and/or an amino group of the hydrophobic substituent by an ester bond and/or an amide bond, and is bonded to a side-chain carboxy group of the aspartic acid chain and/or the glutamic acid chain by an ester bond, an amide bond, or a thioester bond. Examples include $[R_{3a}]$—CO—$(CH_2)_x$—O—[CO-polymer] (wherein x represents an integer from 1 to 8), $[R_{3a}]$—CO—$(CH_2)_x$—NH—[CO-polymer] (wherein x represents an integer from 1 to 8), and $[R_{3a}]$—CO—$(CH_2)_x$—S—[CO-polymer] (wherein x represents an integer from 1 to 8). x in Ba is preferably 1 to 6, and more preferably 1, 2, 3, or 5. The most preferred Ba is $[R_{3a}]$—CO—$(CH_2)_x$—NH—[CO-polymer] (wherein x=1, 2, 3, or 5).

Furthermore, an amino acid derivative may also be used as the divalent bonding group related to Ba. An embodiment of usage of the bonding group in the case of using an amino acid derivative as a bonding group is an embodiment in which the N-terminal amino group of the amino acid derivative is bonded to the side-chain carboxy group by an amide bond, and the C-terminal carboxy group is bonded to a hydroxy group and/or an amino group of the hydrophobic substituent by an ester bond or an amide bond.

In a case in which an amino acid derivative is used as the divalent bonding group related to Ba, any of a naturally occurring amino acid or a synthetic amino acid and a side-chain modification product thereof may be used. Furthermore, any of the L-form, the D-form, and the racemates may also be used. Examples include glycine, alanine, β-alanine, leucine, phenylalanine, serine, threonine, tyrosine, aspartic acid, glutamic acid, lysine, arginine, histidine, ornithine, and cysteine. Furthermore, examples of an amino acid having a modified side chain include an alkyl ester of aspartic acid or glutamic acid, an aralkyl ester of aspartic acid or glutamic acid, an alkylamide of aspartic acid or glutamic acid, an aralkylamide of aspartic acid or glutamic acid, and an alkyloxycarbonyl lysine such as Boc-lysine.

Furthermore, as the divalent bonding group, a glycolic acid derivative in which a hydroxy group and a carboxy group are disposed with a methylene group interposed therebetween may also be used. The embodiment of usage in the case of using a glycolic acid derivative as a divalent bonding group is an embodiment in which a hydroxy group of the glycolic acid derivative is bonded to the side-chain carboxy group by an ester bond, and a carboxy group is bonded to a hydroxy group and/or an amino group of the hydrophobic substituent by an ester bond or an amide bond.

Examples of the glycolic acid derivative include glycolic acid, lactic acid, malic acid, tartaric acid, and citric acid. In the case of using a polyvalent carboxylic acid, it is preferable that one of the carboxy groups is bonded to the hydrophobic substituent, and the other carboxy group is an ester derivative or an amide derivative.

The divalent bonding group may be a bonding group of a single kind, or a plurality of kinds of bonding groups may exist as a mixture.

This Ba may be a single bond. A single bond means an embodiment in which a side-chain carboxy group of the aspartic acid chain and/or the glutamic acid chain is directly bonded to a hydroxy group and/or an amino group of the hydrophobic substituent by an ester bond or an amide bond, particularly without involving a bonding group.

The bonding residue of the hydrophobic substituent for $R_{3a}$ is a product in which a side-chain carboxy group of the poly(aspartic acid and/or glutamic acid) chain is bonded to an ester type modifying group and/or an amide type modifying group. That is, the hydroxy group and/or amino group is a bondable functional group, and the bonding residue represents a residue obtained by excluding a hydrogen atom from the bondable functional group. The hydrophobic substituent may be used without any particular limitations.

$R_{3a}$ in General Formula (1) represents a substituent that includes one or more bonding residues of one or more hydrophobic substituents selected from the group consisting of a linear, branched or cyclic (C1-C30) alkoxy group which may have a substituent, a linear, branched or cyclic (C1-C30) alkylamino group which may have a substituent, a linear, branched or cyclic (C1-C30) dialkylamino group which may have a substituent, a (C1-C8) alkylaminocarbonyl-(C1-C8) alkylamino group which may have a substituent, a bonding residue of a physiologically active substance having a hydroxy group and/or an amino group, and a bonding residue of a fluorescent substance having a hydroxy group and/or an amino group, while the remaining part is a hydroxy group.

$R_{3a}$ is a hydrophobic substituent that is introduced for the purpose of controlling the hydrophobicity of the block copolymer (A). That is, the hydrophobicity of the poly (aspartic acid and/or glutamic acid) chain of the block copolymer (A) may be increased by introducing a hydrophobic group to $R_{3a}$. The extent of the hydrophobicity may be controlled by the degree of hydrophobicity and/or the ratio of introduction of the hydrophobic substituent to be introduced. Therefore, regarding this $R_{3a}$, it is not essential that the entirety is a hydrophobic substituent, and it is acceptable that the remaining part is a hydroxy group. This $R_{3a}$ may be a substituent of a single kind or a plurality of kinds of substituents.

The linear, branched or cyclic (C1-C30) alkoxy group which may have a substituent in connection with $R_{3a}$ is a group in which an ester type modifying group is bonded to a side-chain carboxy group of the poly(aspartic acid and/or glutamic acid) chain. Such substituent may include a hydroxy group, a halogeno group, an amino group, an alkylamino group, a dialkylamino group, an alkoxy group, an aryl group, or the like.

Examples of the (C1-C30) alkoxy group for $R_{3a}$ include a methoxy group, an ethoxy group, a 1-propyloxy group, an isopropyloxy group, an n-butoxy group, a t-butoxy group, a cyclohexyloxy group, a benzyloxy group, a 4-phenylbutyloxy group, an n-octyloxy group, a decyloxy group, a dodecyloxy group, a tetradecyloxy group, a hexadecyloxy group, an octadecyloxy group, an eicosyloxy group, a docosyloxy group, a tetracosyloxy group, a hexacosyloxy group, an octacosyloxy group, and a triacontyloxy group.

The linear, branched or cyclic (C1-C30) alkylamino group which may have a substituent in connection with $R_{3a}$ is a group in which an alkylamide type modifying group is bonded to a side-chain carboxy group of the poly(aspartic acid and/or glutamic acid) chain. Such substituent may include a hydroxy group, a halogeno group, an amino group, an alkylamino group, a dialkylamino group, an alkoxy group, an aryl group, or the like.

Examples of the (C1-C30) alkylamino group for $R_{3a}$ include a methylamino group, an ethylamino group, a propylamino group, an isopropylamino group, a butylamino group, a t-butylamino group, a cyclohexylamino group, a benzylamino group, a 4-phenylbutylamino group, an octylamino group, a decylamino group, a dodecylamino group, a tetradecylamino group, a hexadecylamino group, an octadecylamino group, an eicosylamino group, a docosylamino group, a tetracosylamino group, a hexacosylamino group, an octacosylamino group, and a triacontylamino group.

An amino acid having a protected carboxy group is also included in the (C1-C30) alkylamino group which may have a substituent. Regarding the amino acid having a protected carboxy group, for example, glycine methyl ester, glycine benzyl ester, β-alanine methyl ester, β-alanine benzyl ester, alanine methyl ester, leucine methyl ester, and phenylalanine methyl ester may be used.

The linear, branched or cyclic (C1-C30) dialkylamino group which may have a substituent in connection with $R_{3a}$ is a group in which a dialkylamide type modifying group is bonded to a side-chain carboxy group of the poly(aspartic acid and/or glutamic acid) chain. Such substituent may include a hydroxy group, a halogeno group, an amino group, an alkylamino group, a dialkylamino group, an alkoxy group, an aryl group, or the like.

Examples of the di(C1-C30) alkylamino group for $R_{3a}$ include a dimethylamino group, a diethylamino group, a dipropylamino group, a diisopropylamino group, a dibutylamino group, a pyrrolidino group, a piperidino group, a dibenzylamino group, an N-benzyl-N-methylamino group, a dioctylamino group, a dinonylamino group, a didecylamino group, a didodecylamino group, a ditetradecylamino group, a dihexadecylamino group, a dioctadecylamino group, and a dieicosylamino group.

The (C1-C8) alkylaminocarbonyl-(C1-C8) alkylamino group which may have a substituent in connection with $R_{3a}$ is a group in which a urea type modifying group is bonded to a side-chain carboxy group of the poly(aspartic acid and/or glutamic acid) chain. The alkyl groups may be groups of the same kind, or groups of different kinds.

Such substituent may include a hydroxy group, a halogeno group, an amino group, an alkylamino group, a dialkylamino group, an alkoxy group, an aryl group, or the like. In the case of having a substituent, a dialkylamino group is preferred.

Examples of the (C1-C8) alkylaminocarbonyl-(C1-C8) alkylamino group which may have a substituent include a methylaminocarbonylmethylamino group, an ethylaminocarbonylethylamino group, an isopropylaminocarbonylisopropylamino group, a cyclohexylaminocarbonylcyclohexylamino group, an ethylaminocarbonyl-(3-dimethylaminopropyl)amino group, and a (3-dimethylaminopropyl) aminocarbonylethylamino group.

The bonding residue of a physiologically active substance having a hydroxy group and/or an amino group for $R_{3a}$ is not particularly limited, and it is preferable to apply an active ingredient of a pharmaceutical product or a pharmaceutically active ingredient candidate compound, or to apply an active ingredient obtained by converting the active ingredient or the candidate compound to a derivative or a prodrug. When the diseases to which a polymeric micelle type DDS preparation is applicable are considered, malignant tumor diseases, inflammatory diseases, infectious diseases, and the like may be mentioned. It is preferable to apply an active ingredient of a pharmaceutical product or a pharmaceutically active ingredient candidate compound, which are used for the treatment of these diseases, or to apply an active ingredient obtained by converting the active ingredient or the candidate compound to a derivative or a prodrug. In the following description, examples of a physiologically active substance that are applicable to the present invention will be mentioned; however, the examples are not limited to these.

Examples of a physiologically active substance that is used for malignant tumor diseases include camptothecin derivatives such as 7-ethyl-10-hydroxycamptothecin, irinotecan, nogitecan, and 9-aminocamptothecin; taxane derivatives such as paclitaxel, docetaxel, and cabazitaxel; resorcinol derivatives having HSP90 inhibitory activity, such as ganetespib and luminespib; anthracycline derivatives such as doxorubicin, epirubicin, amrubicin, daunorubicin, idarubicin, and pirarubicin; ramapycin derivatives such as sirolimus, everolimus, and temsirolimus; cytidine-based antimetabolites such as gemcitabine, cytosine arabinoside, enocitabine, cytarabine ocfosfate, ethynylcytidine, azacitidine, and decitabine; folic acid antimetabolites such as methotrexate, pemetrexed, levofolinate, and folinate; purine-based antimetabolites such as fludarabine, nelarabine, pentostatin, and cladribine; pyrimidine fluoride-based antimetabolites such as doxifluridine, capecitabine, tefugar, fluorouracil, and carmofur; platinum-containing compounds such as cisplatin, carboplatin, oxaliplatin, and nedaplatin; mitomycin derivatives such as mitomycin C; bleomycin derivatives such as bleomycin and libromycin; vinca alkaloid derivatives such as vincristine, vinblastine, vindesine, and vinorelbine; podophyllotoxin derivatives such as etoposide and teniposide; halichondrin derivatives such as eribulin; staurosporine derivatives such as rebeccamycin and UCN-01; thalidomide derivatives such as lenalidomide and pomalidomide; vitamin A derivatives such as tretinoin and tamibarotene; proteasome inhibitors such as bortezomib, carfilzomib, and ixazomib; combretastatin derivatives such as combretastatin A4; MEK inhibitors such as binimetinib, cobimetinib, and trametinib; CDK inhibitors such as dinaciclib, flavopiridol, and palbociclib; Raf kinase inhibitors such as dabrafenib, sorafenib, and vemurafenib; HDAC inhibitors such as vorinostat, belinostat, panabinostat, and romidepsin; actin polymerization inhibitors such as cytochalasin, latrunculin, and phalloidin; PARP inhibitors such as veliparib, rucaparib, and olaparib; tyrosine kinase inhibitors such as crizotinib, imatinib, gefitinib, erlotinib, apatinib, dasatinib, bosutinib, vandetanib, sunitinib, axitinib, pazopanib, lenvatinib, lapatinib, nintedanib, nilotinib, ceritinib, alectinib, ruxolitinib, crizotinib, and ibrutinib; nitrogen mustard-based alkylating agents such as bendamustine, cyclophosphamide, ifosfamide, bulusfan, melphalan; nitrosourea-based alkylating agents such as nimustine, ranimustine, and lomustine; alkylating agents such as dacarbazine, temozolomide, procarbazine, and thiotepa; aromatase inhibitors such as anastrozole, exemestane, letrozole, and fadrozole; anti-androgenic agents such as hydroxyflutamide, flutamide, bicalutamide, and enzaltamide; CYP17 (lyase) inhibitors such as abiraterone; anti-estrogenic agents such as tamoxifen and toremifene; and hormonal agents such as estramustine, progesterone, mitotane, and medroxyprogesterone.

Examples of a physiologically active substance that is used for inflammatory diseases include tacrolimus derivatives such as tacrolimus; steroid derivatives such as dexamethasone and prednisolone; ramapycin derivatives such as sirolimus, everolimus, and temsirolimus; immunosuppressants such as cyclosporine, fingolimod, azathioprine, mizoribine, myrcophenolate mofetil, and gusperimus; and NSAIDs such as diflunisal and tiaramide.

Examples of the physiologically active substance that is used for infectious diseases include antifungal agents, such as polyene-based antibiotic substances such as amphotericin B and nystatin, azole-based derivatives such as fluconazole and voriconazole, candin-based derivatives such as micafungin, and pyrimidine derivatives such as flucytosine; and antiviral agents such as acyclovir, valacyclovir, and ganciclovir; and antiviral agents such as zanamivir, oseltamivir, and laninamivir.

$R_{3a}$ may also be a bonding residue of a fluorescent substance having a hydroxy group and/or an amino group. Therefore, in a case in which this $R_{3a}$ is a bonding residue of a fluorescent substance, $R_{3a}$ refers to a bonding residue of a fluorescent substance in which a hydrogen atom has been eliminated from the hydroxy group and/or amino group. It is because the purpose of applying a fluorescent substance to $R_{3a}$ is not particularly intended to affect the effects of the present invention, but is to use the invention as an indicator for checking tissue migration characteristics or excretability.

The fluorescent substance is preferably a fluorescent substance having an amino group, and examples thereof include 2-(2-aminoethoxy)-9-(diethylamino)-5H-benzo[a] phenoxazin-5-one, BODIPY (registered trademark) TR Cadaverine, BODIPY (registered trademark) FL Ethylenediamine, ALEXA FLUOR (registered trademark) 594 Cadaverine, TEXAS RED (registered trademark) Cadaverine, and ATTO 594 amine. Therefore, the bonding residue of a fluorescent substance of $R_{3a}$ includes these amide bonding residues.

$R_3$, in General Formula (1) may also be a hydroxy group. That is, the side-chain carboxylic acid of the poly(aspartic acid and/or glutamic acid) chain is a free carboxylic acid. In this case, the side-chain carboxylic acid may be in the form of a free acid, or may be in the form of any pharmaceutically acceptable arbitrary carboxylic acid salt. Examples of the carboxylic acid salt include a lithium salt, a sodium salt, a potassium salt, a magnesium salt, a calcium salt, and an ammonium salt, all of which are included in the present invention.

In General Formula (1), x1a, x2a, and za respectively represent the content of constituent units of an aspartic acid derivative unit and/or a glutamic acid derivative unit in the poly(aspartic acid and/or glutamic acid) chain of the block copolymer (A), and each represent an integer from 0 to 20. Furthermore, (x1a+x2a+za) represents the number of polymerizations of the poly(aspartic acid and/or glutamic acid) chain, and is an integer from 3 to 20. That is, this represents that the poly(aspartic acid and/or glutamic acid) chain is a polymer having an average number of polymerizations of 3 to 20. When the value of this (x1a+x2a+za) is smaller than 3, there is a risk that the block copolymer (A) thus obtainable may not have self-associating properties. On the other hand, when the number of polymerizations is larger than 20, there is a possibility that the molecular weight of the main chain of the block copolymer (A) thus obtainable may exceed 10 kilodaltons. Thus, there is a risk that desired pharmacokinetics may not be provided. That is, when the value of (x1a+x2a+za), which is the number of polymerizations of the poly(aspartic acid and/or glutamic acid) chain, is not in the range of 3 to 20, there is a risk that the desired pharmacokinetic characteristics may not be successful, and the enhancement action of the pharmacological action effect and the effect of reducing side effects may not be obtained. It is preferable that the number of polymerizations of the polyamino acid derivative is set as appropriate in consideration of the molecular weight of the block copolymer. This (x1a+x2a+za) is preferably an integer from 5 to 20.

The (x1a+x2a+za), which is the number of polymerizations of the polyamino acid derivative, may be determined by measurement by 1H-NMR, or by performing neutralization titration of the polyethylene glycol-poly(aspartic acid and/or glutamic acid) block copolymer before $R_{3a}$ is bonded thereto.

In General Formula (1), (x1a+x2a) represents the total number of aspartic acid units and/or glutamic acid units, to which the hydrophobic substituent related to $R_{3a}$ is bonded. A unit having the hydrophobic substituent bonded thereto is an essential configuration, and the (x1a+x2a) is an integer from 1 to 20. Preferably, this (x1a+x2a) is an integer from 2 to 20, and more preferably an integer from 3 to 15. The proportion of (x1a+x2a) with respect to (x1a+x2a+za), which is the number of polymerizations of the poly(aspartic acid and/or glutamic acid) chain, is 4% to 100%. The proportion is preferably 10% to 90%, and more preferably 20% to 80%.

The content number of the aspartic acid units and/or glutamic acid units having the hydrophobic substituent bonded thereto, which is related to (x1a+x2a), is calculated from the amount of bonding of the hydrophobic substituent and the number of polymerizations of the poly(aspartic acid and/or glutamic acid) chain. The amount of bonding of the hydrophobic substituent may be determined by a method of cleaving the hydrophobic substituent from the block copolymer having the hydrophobic substituent bonded thereto, and quantitatively analyzing the released hydrophobic substituent. A method of calculating the amount of bonding from the reaction ratio of the hydrophobic substituent at the time of producing the block copolymer having the hydrophobic substituent bonded thereto may also be used.

In regard to the block copolymer having a hydrophobic substituent bonded thereto, which is represented by General Formula (1) according to the invention, the poly(aspartic acid and/or glutamic acid) chain is a polymer segment in which aspartic acid units and/or glutamic acid units having $R_{3a}$ at the side-chain carboxy group, and aspartic acid units and/or glutamic acid units having a structure in which the side-chain carboxy group has been intramolecularly cyclized, exist as a mixture. One or more units exist for the respective constituent units, and the block copolymer has a segment structure in which the arrangement of the constituent units is not particularly controlled, and the constituent units are randomly arranged in an irregular arrangement.

Regarding the block copolymer having a hydrophobic substituent bonded thereto as represented by General Formula (1) excluding the target binding site, it is preferable that the mass content percentage of the hydrophobic substituent represented by $R_{3a}$ is not less than 5% by mass and not more than 60% by mass. In both of a case in which the content of the hydrophobic substituent is lower than 5% by mass, and a case in which the content of the hydrophobic substituent is larger than 60% by mass, the hydrophilicity-hydrophobicity balance of the block copolymer having a hydrophobic substituent bonded thereto is largely changed, and there is a risk that the block copolymer may not have appropriate self-associating properties, and desired pharmacokinetics may not be exhibited. The mass content percentage of the hydrophobic substituent is preferably not less than 5% by mass and not more than 50% by mass, and more preferably not less than 8% by mass and not more than 40% by mass.

The molecular weight of the main chain polymer combining the polyethylene glycol chain and the polyamino acid chain in the block copolymer represented by General Formula (1), from which the target binding site $R_1$, the hydrophobic substituent $R_{3a}$, and the bonding group Ba have been excluded, is not less than 2 kilodaltons and not more than 10 kilodaltons. Regarding this molecular weight, a calculated value obtained by summing the constituent molecular weights of the constituent moieties is employed as the molecular weight. That is, a calculated value of summing (1) the molecular weight of the polyethylene glycol chain and (2) the molecular weight of the main chain portion of the polyamino acid chain, is employed as the molecular weight.

The molecular weight of the main chain polymer combining a polyethylene glycol chain and a polyamino acid chain may described with accuracy to the nearest kilodalton unit. In the following description, a preferred analysis method for the various constituent moieties will be described; however, any analysis method with sufficiently accurate for the measurement of the molecular weight of the polyamino acid derivative to the nearest kDa unit may be used without any particular limitations.

The (1) molecular weight of the polyethylene glycol chain is a measured value of the molecular weight of the polyethylene glycol compound that constructs the polyethylene glycol segment. The molecular weight that may be determined from the peak top molecular weight measured by a GPC method based on polyethylene glycol standards is employed. Regarding the calculated value, a value rounded off to the nearest hundred is used.

The (2) molecular weight of the main chain portion of the polyamino acid is a calculated value obtained by multiplying the molecular weight of a polymerization monomer unit of the polyamino acid chain included in the hydrophobic polymer segment by the average number of polymerizations. Regarding the number of polymerizations, a number of polymerizations obtained by a method of quantitatively determining the amount of side-chain carboxy groups in the polyamino acid by neutralization titration, or calculated from the integral values of 1H-NMR, may be used. It is preferable to use a neutralization titration method.

In regard to the block copolymer (A) represented by General Formula (1) of the invention, the molecular weight of the main chain polymer combining the polyethylene glycol chain and the polyamino acid chain in the block copolymer excluding the target binding site $R_1$, the hydrophobic substituent $R_{3a}$, and the bonding group Ba, is not less than 2 kilodaltons and not more than 10 kilodaltons. When the molecular weight is smaller than 2 kilodaltons, the block copolymer represented by General Formula (1) may not have sufficient nanoparticle-forming ability, and sufficient migration characteristics, penetrability, and retention characteristics toward a target tissue are not obtained. Therefore, when a physiologically active substance is incorporated, the block copolymer may not efficiently exhibit the pharmacological action effect. Meanwhile, when the molecular weight is larger than 10 kilodaltons, the block copolymer has enhanced in vivo retention characteristics as the kidney excretability is suppressed. Therefore, sensitization of the physiologically active substance in a normal tissue other than a diseased target tissue may occur, and therefore, there is a concern about the expression of disorders in the normal tissue. For example, in the case of using a physiologically active substance having cytotoxicity, prolongation of blood toxicity associated with bone marrow disorder may be considered. Therefore, it is necessary to control the molecular weight to a value of 10 kilodaltons or less. The molecular weight of the block copolymer is preferably not less than 2 kilodaltons and not more than 8 kilodaltons, and more preferably not less than 2 kilodaltons and not more than 7 kilodaltons.

The block copolymer (A) represented by General Formula (1) of the invention exhibits self-associating properties in an aqueous solution, and the particle size (average particle size) is preferably 30 nm or less, and more preferably not less than 3 nm and not more than 30 nm.

The particle size (volume-based particle size) of the block copolymer (A) represented by General Formula (1) of the present invention is measured from a 1 mg/mL aqueous solution of the block copolymer (A) represented by General Formula (1) of the present invention by a dynamic light scattering method using laser light. For example, the particle size may be measured with a particle size/zeta potential measuring apparatus, Zetasizer Nano ZS, manufactured by Malvern Panalytical, Ltd. The volume-based particle size at this time is the particle size of the peak that exists at the largest proportion in a volume distribution analyzed by an NNLS method.

[Block Copolymer (B)]

Next, a block copolymer (B) including a hydrophilic polymer segment linked to a hydrophobic polymer segment, the hydrophilic polymer segment containing a polyethylene glycol chain, and the hydrophobic polymer segment containing a polyamino acid chain having a hydrophobic substituent in a side chain, wherein the molecular weight of the main chain polymer combining the polyethylene glycol chain and the polyamino acid chain is not less than 2 kilodaltons and not more than 10 kilodaltons, and the mass content percentage of the hydrophobic substituent is not less than 5% by mass and not more than 50% by mass, will be explained.

The block copolymer (B) is the same as the block copolymer (A) from the viewpoint that an AB block copolymer formed by linking a hydrophilic polymer segment portion containing a polyethylene glycol chain to a hydrophobic polymer segment containing a polyamino acid chain having a hydrophobic substituent in a side chain via an appropriate bonding group is employed as the main chain structure of the carrier polymer. Meanwhile, the block copolymer (B) is different from the block copolymer (A) from the viewpoint that the block copolymer (B) does not have a target binding site at one of the terminal sites of the polyethylene glycol chain which is the hydrophilic polymer segment, and that the block copolymer (B) does not include a physiologically active substance having a hydroxy group and/or an amino group as a hydrophobic substituent in the hydrophobic polymer segment. Thus, the block copolymer (B) will be explained below mainly based on the differences.

The terminal group that is not on the polyamino acid chain-bonded side of the polyethylene glycol chain in the block copolymer (B) is not particularly limited, and examples include a hydrogen atom, a linear, branched or cyclic (C1-C6) alkyl group which may have a substituent, a (C2-C6) alkynyl group which may have a substituent, and a (C7-C20) aralkyl group which may have a substituent. Examples of the substituent that may be carried by the alkyl group, alkynyl group, and aralkyl group include a hydroxy group, an amino group, a formyl group, and a carboxy group.

In regard to the terminal group that is not on the polyamino acid chain-bonded side of the polyethylene glycol chain in the block copolymer (B), examples of a linear alkyl group which may have a substituent include a methyl group, an ethyl group, an n-propyl group, an n-butyl group, an n-pentyl group, and an n-hexyl group. Examples of a branched alkyl group which may have a substituent include an isopropyl group, an isobutyl group, a t-butyl group, an isopentyl group, a 2-methylbutyl group, a neopentyl group, a 1-ethylpropyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, and a 2-ethylbutyl group. Examples of a cyclic alkyl group which may have a substituent include a cyclopropyl group, a cyclobutyl group, a cyclopentyl group, and a cyclohexyl group.

In regard to the terminal group that is not on the polyamino acid chain-bonded side of the polyethylene glycol chain in the block copolymer (B), examples of the substituent that may be carried by the linear alkyl group include a thiol group, a hydroxy group, a halogeno group, a nitro group, a cyano group, an alkylthio group, a carbocyclic or heterocyclic aryl group, an arylthio group, an alkylsulfinyl group, an arylsulfinyl group, an alkylsulfonyl group, a sulfamoyl group, an alkoxy group, an aryloxy group, an acyloxy group, an alkoxycarbonyloxy group, a carbamoyloxy group, a substituted or unsubstituted amino group, an acylamino group, an alkoxycarbonylamino group, a ureido group, a sulfonylamino group, a sulfamoylamino group, a formyl group, an acyl group, a carboxy group, an alkoxycarbonyl group, a carbamoyl group, and a silyl group.

In regard to the terminal group that is not on the polyamino acid chain-bonded side of the polyethylene glycol chain in the block copolymer (B), examples of the (C2-C6) alkynyl group which may have a substituent include a 2-propynyl, a 3-butynyl group, a 4-heptynyl group, and a 5-hexynyl group.

In regard to the terminal group that is not on the polyamino acid chain-bonded side of the polyethylene glycol chain in the block copolymer (B), the (C7-C20) aralkyl group which may have a substituent is a linear or branched alkyl group in which a hydrogen at any one site has been substituted by an aryl group, including a benzyl group, a 2-phenylethyl group, a 4-phenylbutyl group, a 3-phenylbutyl group, a 5-phenylpentyl group, a 6-phenylhexyl group, and an 8-phenyloctyl group, preferably a benzyl group, a 4-phenylbutyl group, and an 8-phenyloctyl group.

The hydrophobic substituent in the hydrophobic polymer segment of the block copolymer (B) is preferably one or more substituents selected from the group consisting of a (C1-C30) alkoxy group which may have a substituent, a (C1-C30) alkylamino group which may have a substituent, a di(C1-C30) alkylamino group which may have a substituent, and a (C1-C8) alkylaminocarbonyl-(C1-C8) alkylamino group which may have a substituent. The percentage content of these hydrophobic substituents in the block copolymer (B) is preferably not less than 5% by mass and not more than 60% by mass. In a case in which the percentage content of the hydrophobic substituent is less than 5% by mass, the hydrophobicity of the hydrophobic polymer segment in the block copolymer (B) is weak, and there is a risk that sufficient associating properties based on hydrophobic interaction may not be obtained. Meanwhile, in a case in which the percentage content of the hydrophobic substituent is more than 60% by mass, the block copolymer has sufficient associating properties; however, there is a risk that satisfactory pharmacokinetic characteristics may not be provided with regard to the penetrability and distribution characteristics to and in a diseased tissue or excretability out of the body. The percentage content of the hydrophobic substituent in the block copolymer (B) is more preferably not less than 5% by mass and not more than 50% by mass.

The (C1-C30) alkoxy group which may have a substituent, the (C1-C30) alkylamino group which may have a substituent, the di(C1-C30) alkylamino group which may have a substituent, or the (C1-C8) alkylaminocarbonyl-(C1-C8) alkylamino group which may have a substituent, all of which may be mentioned as the hydrophobic substituent, have the same meanings as those mentioned for the block copolymer (A). Meanwhile, the block copolymer (B) is in the form that does not include a physiologically active substance as the hydrophobic substituent.

In regard to the block copolymer (B), the molecular weight of the main chain polymer combining the polyethylene glycol chain and the polyamino acid chain is not less than 2 kilodaltons and not more than 10 kilodaltons. It is preferable that the molecular weight is not less than 2 kilodaltons and not more than 8 kilodaltons.

For this molecular weight, a calculated value obtained by summing the various constituent molecular weights of the constituent moieties of the block copolymer is employed as the molecular weight. That is, a calculated value obtained by combining the (1) molecular weight of the polyethylene glycol chain and the (2) molecular weight of the main chain portion of the polyamino acid chain is employed as the relevant molecular weight. Meanwhile, since the hydrophobic substituent in the block copolymer (B) is not included in the main chain polymer, the hydrophobic substituent is not considered for the calculation of the molecular weight.

Meanwhile, the molecular weight of the main chain polymer combining the polyethylene glycol chain and the polyamino acid chain may be described with accuracy to the nearest kilodalton unit. In the following description, a preferred analysis method for the various constituent moieties will be described; however, any analysis method with sufficiently accurate for the measurement of the molecular weight of the polyamino acid derivative to the nearest kDa unit may be used without any particular limitations.

The (1) molecular weight of the polyethylene glycol chain is a measured value of the molecular weight of the polyethylene glycol compound that constructs the polyethylene glycol segment. The molecular weight that may be determined from the peak top molecular weight measured by a GPC method based on polyethylene glycol standards is employed. Regarding the calculated value, a value rounded off to the nearest hundred is used.

The (2) molecular weight of the main chain portion of the polyamino acid is a calculated value obtained by multiplying the molecular weight of the polymerization monomer unit of the polyamino acid chain included in the hydrophobic polymer segment by the average number of polymerizations. Regarding this number of polymerizations, a number of polymerizations calculated by a method of quantitatively determining the amount of side-chain carboxy groups of the polyamino acid by neutralization titration, or calculated from the integral values of 1H-NMR, may be used. It is preferable to use a neutralization titration method.

The block copolymer (B) of the invention exhibits self-associating properties in an aqueous solution.

The particle size (average particle size) of the nanoparticles of the invention is preferably 30 nm or less. The particle size is more preferably not less than 3 nm and not more than 30 nm, and particularly preferably not less than 3 nm and less than 20 nm.

The particle size (average particle size) of the nanoparticles according to the invention is measured by, for example, an induced diffraction grating method. An induced diffraction grating method is a method of: (1) irradiating a 2 to 5 mg/mL aqueous solution of the block copolymer (B) of the invention with laser light, thereby forming diffraction gratings by dielectrophoresis; (2) stopping an external force that causes dielectrophoresis, measuring the annihilation rate of the diffraction gratings caused by diffusion, and (3) applying the annihilation rate to the Stokes-Einstein relational equation to be obtain the particle size. For example, the particle size may be measured with a single nanoparticle size measuring apparatus, IG-1000, manufactured by Shimadzu Corp.

Since the block copolymer (B) of the invention is a block copolymer in which a hydrophilic polyethylene glycol segment is linked to a polyamino acid derivative segment exhibiting hydrophobicity by means of a hydrophobic side chain, it is considered that the polyamino acid derivative segments of a plurality of block copolymers will associate with one another in an aqueous solution based on hydrophobic interaction. As a result, it is speculated that the block copolymer molecules form micelle-like associates having a core-shell structure in which the polyamino acid derivative segment forms the inner core (core part), and the hydrophilic polyethylene glycol segment covers the periphery of the inner core and forms an outer shell layer (shell part), and these micelle-like associates are observed as nanoparticles described above.

A block copolymer (B) including a hydrophilic polymer segment linked to a hydrophobic polymer segment, the hydrophilic polymer segment containing a polyethylene glycol chain and the hydrophobic polymer segment containing a polyamino acid chain having a hydrophobic substituent in a side chain, wherein the molecular weight of the main chain polymer combining the polyethylene glycol chain and the polyamino acid chain is not less than 2 kilodaltons and not more than 10 kilodaltons, and the mass content percentage of the hydrophobic substituent is not less than 5% by mass and not more than 50% by mass, is preferably a block copolymer represented by General Formula (2):

[Chemical Formula 5]

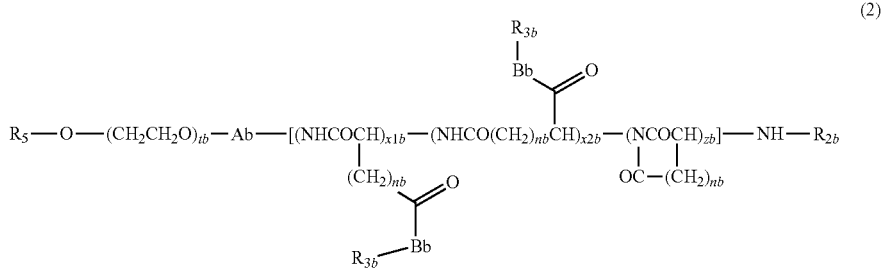

wherein $R_5$ represents a hydrogen atom or a (C1-C6) alkyl group which may have a substituent; tb represents an integer from 20 to 140; Ab represents a (C1-C6) alkylene group which may have a substituent; $R_{2b}$ represents a substituent selected from the group consisting of a hydrogen atom, a (C1-C6) acyl group, and a (C1-C6) alkoxycarbonyl group; $R_{3b}$ includes one or more bonding residues of one or more hydrophobic substituents selected from the group consisting of a linear, branched or cyclic (C1-C30) alkoxy group which may have a substituent, a linear, branched or cyclic (C1-C30) alkylamino group which may have a substituent, a linear, branched or cyclic (C1-C30) dialkylamino group which may have a substituent, a (C1-C8) alkylaminocarbonyl-(C1-C8) alkylamino group which may have a substituent, and a bonding residue of a fluorescent substance having a hydroxy group and/or an amino group, while the remaining part is a hydroxy group; Bb represents a single bond or a divalent bonding group; nb represents 1 or 2; x1b, x2b, and zb each independently represent an integer from 0 to 20; x1b+x2b represents an integer from 1 to 20; (x1b+x2b+zb) represents an integer from 3 to 20; and the various constituent units to which $R_{3b}$ is bonded, and the constituent unit formed by intramolecular cyclization of a side-chain carbonyl group constitute a structure with those constituent units being each independently randomly arranged.

The (C1-C6) alkyl group which may have a substituent in connection with $R_5$ may be a linear, branched or cyclic (C1-C6) alkyl group which may have a substituent. Examples include a methyl group, an ethyl group, an n-propyl group, an isopropyl group, an n-butyl group, an s-butyl group, a t-butyl group, an n-pentyl group, a cyclopentyl group, an n-hexyl group, and a cyclohexyl group.

Examples of the substituent that may be carried include a halogeno group, a nitro group, a cyano group, a hydroxy group, a mercapto group, a carbocyclic or heterocyclic aryl group, an alkylthio group, an arylthio group, an alkylsulfinyl group, an arylsulfinyl group, an alkylsulfonyl group, an arylsulfonyl group, a sulfamoyl group, an alkoxy group, an aryloxy group, an acyloxy group, an alkoxycarbonyloxy group, a carbamoyloxy group, a substituted or unsubstituted amino group, an acylamino group, an alkoxycarbonylamino group, a ureido group, a sulfonylamino group, a sulfamoylamino group, a formyl group, an acyl group, a carboxy group, an alkoxycarbonyl group, a carbamoyl group, and a silyl group. The position of substitution on the aromatic ring may be the ortho-position, the meta-position, or the para-position.

Examples of $R_1$ include a methyl group, an ethyl group, an n-propyl group, an isopropyl group, an n-butyl group, an s-butyl group, a t-butyl group, a benzyl group, a 2,2-dimethoxyethyl group, a 2,2-diethoxyethyl group, and a 2-formylethyl group. Particularly, a methyl group, an ethyl group, an n-propyl group, an isopropyl group, an n-butyl group, an s-butyl group, a t-butyl group, and the like are more preferred.

tb, Ab, $R_{2b}$, nb, Bb, x1b, x2b, and zb of General Formula (2) are the same as ta, Aa, $R_{2a}$, na, Ba, x1a, x2a, and za of General Formula (1) described above, respectively. $R_{3b}$ of General Formula (2) is the same as a group obtained by excluding the bonding residue of a physiologically active substance having a hydroxy group and/or an amino group from $R_{3a}$ in General Formula (1).

In regard to the block copolymer (B) having a hydrophobic substituent bonded thereto as represented by General Formula (2) according to the invention, the poly(aspartic acid and/or glutamic acid) chain is a polymer segment in which an aspartic acid unit and/or a glutamic acid unit including $R_{3b}$ at a side-chain carboxy group, and an aspartic acid unit and/or a glutamic acid unit having a structure in which a side-chain carboxy group has been intramolecularly cyclized, exist as a mixture. Each of the constituent units exists in one or more units, the arrangement of the constituent units is not particularly controlled, and the polymer segment has a randomly arranged segment structure in which the constituent units are irregularly arranged.

It is preferable that the block copolymer having a hydrophobic substituent bonded thereto as represented by General Formula (2) has a mass content percentage of the hydrophobic substituent represented by $R_{3b}$ of not less than 5% by mass and not more than 60% by mass. Both in a case in which the content of the hydrophobic substituent is less than 5% by mass, and a case in which the content of the hydrophobic substituent is larger than 60% by mass, the hydrophilicity-hydrophobicity balance of the block copolymer having the hydrophobic substituent bonded thereto is largely changed, and there is a risk that the block copolymer may not have appropriate self-associating properties and may not exhibit desired pharmacokinetics. The mass content percentage of the hydrophobic substituent is preferably not less than 5% by mass and not more than 50% by mass, and more preferably not less than 8% by mass and not more than 40% by mass.

The molecular weight of the main chain polymer combining the polyethylene glycol chain and the polyamino acid chain in the block copolymer (B) represented by General Formula (2) is not less than 2 kilodaltons and not more than 10 kilodaltons. Regarding this molecular weight, a calculated value obtained by summing the various constituent molecular weights of the constituent moieties without including the hydrophobic substituent $R_{3b}$ and the bonding group Bb, is employed as the molecular weight. That is, a calculated value obtained by summing the (1) molecular weight of the polyethylene glycol chain and the (2) molecular weight of the polyamino acid chain main chain portion is employed as the molecular weight.

The molecular weight of the main chain polymer combining the polyethylene glycol chain and the polyamino acid chain is may be described with accuracy to the nearest kilodalton unit. In the following description, a preferable analysis method for the various constituent moieties will be described; however, any analysis method with sufficiently accurate for the measurement of the molecular weight of the polyamino acid derivative to the nearest kDa unit may be used without any particular limitations.

The (1) molecular weight of the polyethylene glycol chain is a measured value of the molecular weight of the polyethylene glycol compound that constructs the polyethylene glycol segment. The molecular weight that may be determined from the peak top molecular weight measured by a GPC method based on polyethylene glycol standards is employed. Regarding the calculated value, a value rounded off to the nearest hundred is used.

The (2) molecular weight of the main chain portion of the polyamino acid is a calculated value obtained by multiplying the molecular weight of the polymerization monomer unit of the polyamino acid chain included in the hydrophobic polymer segment by the average number of polymerizations. Regarding the number of polymerizations, a number of polymerizations obtained by a method of quantitatively determining the amount of side-chain carboxy groups in the polyamino acid by neutralization titration, or calculated from the integral values of $^1$H-NMR, may be used. It is preferable to use a neutralization titration method.

The molecular weight of the main chain polymer combining the polyethylene glycol chain and the polyamino acid chain in the block copolymer represented by General Formula (2) of the invention is not less than 2 kilodaltons and not more than 10 kilodaltons. In a case in which the molecular weight is smaller than 2 kilodaltons, a polymeric micelle type DDS preparation including the block copolymer (B) represented by General Formula (2) does not have sufficient nanoparticle-forming ability and may not exhibit sufficient migration characteristics, penetrability, and retention characteristics toward a target tissue. As a result, in a case in which a physiologically active substance is incorporated, the physiologically active substance may not efficiently exhibit pharmacological action effects. Meanwhile, in a case in which the molecular weight is larger than 10 kilodaltons, kidney excretability is suppressed, and accordingly, in vivo retention characteristics are enhanced. Therefore, since sensitization of a physiologically active substance may occur in a normal tissue other than a diseased target tissue, there is a risk of exhibition of disorders in the normal tissue. For example, in the case of using a cytotoxic physiologically active substance, prolongation of blood toxicity associated with bone marrow disorder may be considered. Therefore, it is necessary to control the molecular weight to a value of 10 kilodaltons or less. The molecular weight of the block copolymer is preferably not lese than 2 kilodaltons and not more than 8 kilodaltons, and more preferably not less than 2 kilodaltons and not more than 7 kilodaltons.

The block copolymer (B) represented by General Formula (2) of the invention exhibits self-associating properties in an aqueous solution.

The particle size (average particle size) of the nanoparticles of the invention is preferably 30 nm or less, more preferably not less than 3 nm and not more than 30 nm, and particularly preferably not less than 3 nm and less than 20 nm.

The particle size (average particle size) of the nanoparticles according to the invention is measured by, for example, an induced diffraction grating method. An induced diffraction grating method is a method of: (1) irradiating a 2 to 5 mg/mL aqueous solution of the block copolymer (B) represented by General Formula (2) of the invention with laser light, thereby forming diffraction gratings by dielectrophoresis; (2) stopping an external force that causes dielectrophoresis, measuring the annihilation rate of the diffraction gratings caused by diffusion, and (3) applying the annihilation rate to the Stokes-Einstein relational equation to obtain the particle size. For example, the particle size may be measured with a single nanoparticle size measuring apparatus, IG-1000, manufactured by Shimadzu Corp.

[Block Copolymer (C)]

Next, a block copolymer (C) including a hydrophilic polymer segment connected a hydrophobic polymer segment, the hydrophilic polymer segment containing a polyethylene glycol chain, and the hydrophobic polymer segment containing a polyamino acid chain having a physiologically active substance having a hydroxy group and/or an amino group bonded to a side-chain carboxy group, wherein the molecular weight of the main chain polymer combining the polyethylene glycol chain and the polyamino acid chain is not less than 2 kilodaltons and not more than 10 kilodaltons, and the mass content percentage of the physiologically active substance having a hydroxy group and/or an amino group is nor less than 5% by mass and not more than 50% by mass, will be explained.

The block copolymer (C) is the same as the block copolymer (B) from the viewpoint that an AB block copolymer formed by linking the hydrophilic polymer segment portion containing the polyethylene glycol chain to the hydrophobic polymer segment containing a polyamino acid chain having a hydrophobic substituent in a side chain via an appropriate bonding group, is used as the main chain structure of the carrier polymer. Meanwhile, the block copolymer (C) is different from the block copolymer (B) from the viewpoint that an embodiment in which the hydrophobic polymer segment is a polyamino acid chain having a side-chain carboxy group, and a physiologically active substance having a hydroxy group and/or an amino group is bonded to the side-chain carboxy group by an ester bond and/or an amide bond is an essential configuration. That is, the block copolymer (C) functions as a polymeric prodrug that dissociates and releases the bonded physiologically active substance after being administered into the living body. The block copolymer (C) will be explained below mainly based on the difference.

The hydrophobic polymer segment of the block copolymer (C) is a polyamino acid chain having a side chain carboxy group and is in the form in which a physiologically active substance having a hydroxy group and/or an amino group is bonded to the side-chain carboxy group by an ester bond and/or an amide bond.

The polyamino acid chain in the hydrophobic polymer segment is preferably a polyamino acid chain containing aspartic acid and/or glutamic acid which is an amino acid having a carboxylic acid side chain that may have a physiologically active substance introduced thereinto in a controlled manner. More preferably, the polyamino acid chain is preferably a polyaspartic acid chain constructed from aspartic acid only, a polyglutamic acid chain constructed from glutamic acid only, or a poly(aspartic acid-glutamic acid)

chain in which aspartic acid and glutamic acid exist in a random mixture. These polyamino acid chains having side-chain carboxy groups may be α-amide bonded type polymers, an α-amide bond type polymer, an amide bond type polymer having a side-chain carboxy group bonded thereto by an amide bond, a β- (or γ-) amide bond type polymer, or a mixture thereof. Furthermore, the polyamino acid chains may be linear polyamino acids, or branched type structures having side chains.

The physiologically active substance having a hydroxy group and/or an amino group, which is included in the block copolymer (C), is not particularly limited, and it is preferable to apply an active ingredient of a pharmaceutical product or a pharmaceutically active ingredient candidate compound, or to apply an active compound obtained by converting the aforementioned compound into a derivative or a prodrug. When the diseases to which a polymeric micelle type DDS preparation is applicable are considered, malignant tumor diseases, inflammatory diseases, infectious diseases, and the like may be mentioned. It is preferable to apply an active ingredient of a pharmaceutical product or a pharmaceutically active ingredient candidate compound, which are used for the treatment of these diseases, or to apply an active ingredient obtained by converting the aforementioned compound into a derivative or a prodrug. In the following description, examples of a physiologically active substance that are applicable to the invention will be listed; however, the examples are not limited to these.

Examples of the physiologically active substance that is used for malignant tumor diseases include camptothecin derivatives such as 7-ethyl-10-hydroxycamptothecin, irinotecan, nogitecan, and 9-aminocamptothecin; taxane derivatives such as paclitaxel, docetaxel, and cabazitaxel; resorcinol derivatives having HSP90 inhibitory activity, such as ganetespib and luminespib; anthracycline derivatives such as doxorubicin, epirubicin, amrubicin, daunorubicin, idarubicin, and pirarubicin; ramapycin derivatives such as sirolimus, everolimus, and temsirolimus; cytidine-based antimetabolites such as gemcitabine, cytosine arabinoside, enocitabine, cytarabine ocfosfate, ethynylcytidine, azacitidine, and decitabine; folic acid antimetabolites such as methotrexate, pemetrexed, levofolinate, and folinate; purine-based antimetabolites such as fludarabine, nelarabine, pentostatin, and cladribine; pyrimidine fluoride-based antimetabolites such as doxifluridine, capecitabine, tefugar, fluorouracil, and carmofur; platinum-containing compounds such as cisplatin, carboplatin, oxaliplatin, and nedaplatin; mitomycin derivatives such as mitomycin C; bleomycin derivatives such as bleomycin and libromycin; vinca alkaloid derivatives such as vincristine, vinblastine, vindesine, and vinorelbine; podophyllotoxin derivatives such as etoposide and teniposide; halichondrin derivatives such as eribulin; staurosporine derivatives such as rebeccamycin and UCN-01; thalidomide derivatives such as lenalidomide and pomalidomide; vitamin A derivatives such as tretinoin and tamibarotene; proteasome inhibitors such as bortezomib, carfilzomib, and ixazomib; combretastatin derivatives such as combretastatin A4; MEK inhibitors such as binimetinib, cobimetinib, and trametinib; CDK inhibitors such as dinaciclib, flavopiridol, and palbociclib; Raf kinase inhibitors such as dabrafenib, sorafenib, and vemurafenib; HDAC inhibitors such as vorinostat, belinostat, panabinostat, and romidepsin; actin polymerization inhibitors such as cytochalasin, latrunculin, and phalloidin; PARP inhibitors such as veliparib, rucaparib, and olaparib; tyrosine kinase inhibitors such as crizotinib, imatinib, gefitinib, erlotinib, apatinib, dasatinib, bosutinib, vandetanib, sunitinib, axitinib, pazopanib, lenvatinib, lapatinib, nintedanib, nilotinib, ceritinib, alectinib, ruxolitinib, crizotinib, and ibrutinib; nitrogen mustard-based alkylating agents such as bendamustine, cyclophosphamide, ifosfamide, bulusfan, melphalan; nitrosourea-based alkylating agents such as nimustine, ranimustine, and lomustine; alkylating agents such as dacarbazine, temozolomide, procarbazine, and thiotepa; aromatase inhibitors such as anastrozole, exemestane, letrozole, and fadrozole; anti-androgenic agents such as hydroxyflutamide, flutamide, bicalutamide, and enzalutamide; CYP17 (lyase) inhibitors such as abiraterone; anti-estrogenic agents such as tamoxifen and toremifene; and hormonal agents such as estramustine, progesterone, mitotane, and medroxyprogesterone.

Examples of a physiologically active substance that is used for inflammatory diseases include tacrolimus derivatives such as tacrolimus; steroid derivatives such as dexamethasone and prednisolone; ramapycin derivatives such as sirolimus, everolimus, and temsirolimus; immunosuppressants such as cyclosporine, fingolimod, azathioprine, mizoribine, myrcophenolate mofetil, and gusperimus; and NSAIDs such as diflunisal and tiaramide.

Examples of the physiologically active substance that is used for infectious diseases include antifungal agents, such as polyene-based antibiotic substances such as amphotericin B and nystatin, azole-based derivatives such as fluconazole and voriconazole, candin-based derivatives such as micafungin, and pyrimidine derivatives such as flucytosine; and antiviral agents such as acyclovir, valacyclovir, and ganciclovir; and antiviral agents such as zanamivir, oseltamivir, and laninamivir.

It is preferable that the percentage content of the physiologically active substance having a hydroxy group and/or an amino group in the block copolymer (C) is not less than 5% by mass and not more than 60% by mass. In a case in which the percentage content of the physiologically active substance is lower than 5% by mass, the hydrophobicity of the hydrophobic polymer segment of the block copolymer (C) is weak, and there is a risk that sufficient associating properties based on hydrophobic interaction may not be obtained. Furthermore, the block copolymer as a DDS carrier for obtaining a desired amount of administration of the physiologically active substance should be administered in a large amount, which is not preferable. On the other hand, in a case in which the percentage content of the hydrophobic substituent is more than 60% by mass, the block copolymer has sufficient associating properties; however, there is a risk that satisfactory pharmacokinetic characteristics may not be provided with regard to the penetrability and distribution characteristics to and in a diseased tissue and excretability out of the body. The percentage content of the hydrophobic substituent in the block copolymer (C) is preferably not less than 5% by mass and not more than 50% by mass.

The block copolymer (C) may have any arbitrary hydrophobic substituent introduced into a side-chain carboxy group for the purpose of regulating the associate-forming properties. It is preferable that the hydrophobic substituent is one or more substituents selected from the group consisting of, for example, a (C1-C30) alkoxy group which may have a substituent, a (C1-C30) alkylamino group which may have a substituent, a di(C1-C30) alkylamino group which may have a substituent, and a (C1-C8) alkylaminocarbonyl-(C1-C8) alkylamino group which may have a substituent.

The (C1-C30) alkoxy group which may have a substituent, the (C1-C30) alkylamino group which may have a substituent, the di(C1-C30) alkylamino group which may have a substituent, and the (C1-C8) alkylaminocarbonyl- (C1-C8) alkylamino group which may have a substituent, all of which may be mentioned as hydrophobic substituents, have the same meanings as those for the block copolymers (A) and (B). The block copolymer (B) is in the form that does not include a physiologically active substance as the hydrophobic substituent.

In regard to the block copolymer (C), the molecular weight of the main chain polymer combining the polyethylene glycol chain and the polyamino acid chain is not less than 2 kilodaltons and not more than 10 kilodaltons. It is preferable that the molecular weight is not less than 2 kilodaltons and not more than 8 kilodaltons.

For this molecular weight, a calculated value obtained by summing the respective constituent molecular weights of the constituent moieties is employed. That is, a calculated value obtained by summing the (1) molecular weight of the polyethylene glycol chain and the (2) molecular weight of the main chain portion of the polyamino acid chain is employed as the molecular weight. Meanwhile, since the physiologically active substance for the block copolymer (C) is not included in the main chain polymer, the physiologically active substance is not considered into the calculation of the molecular weight.

Meanwhile the molecular weight of the main chain polymer combining the polyethylene glycol chain and the polyamino acid chain is may be described with accuracy to the nearest kilodalton unit. In the following description, a preferable analysis method for the various constituent moieties will be described; however, any analysis method with sufficient accuracy for the measurement of the molecular weight of the polyamino acid derivative to the nearest kDa unit may be used without any particular limitations.

The (1) molecular weight of the polyethylene glycol chain is a measured value of the molecular weight of the polyethylene glycol compound that constructs the polyethylene glycol segment. The molecular weight that may be determined from the peak top molecular weight measured by a GPC method based on polyethylene glycol standards is employed. Regarding the calculated value, a value rounded off to the nearest hundred is used.

The (2) molecular weight of the main chain portion of the polyamino acid is a calculated value obtained by multiplying the molecular weight of the polymerization monomer unit of the polyamino acid chain included in the hydrophobic polymer segment by the average number of polymerizations. Regarding the number of polymerizations, a number of polymerizations calculated by a method of quantitatively determining the amount of side-chain carboxy groups of the polyamino acid by neutralization titration, or calculated from the integral values of $^{1}$H-NMR, may be used. It is preferable to use a neutralization titration method.

The block copolymer (C) of the invention exhibits self-associating properties in an aqueous solution.

The particle size (average particle size of the nanoparticles of the invention is preferably 30 nm or less, more preferably not less than 3 nm and not more than 30 nm, and particularly preferably not less than 3 nm and less than 20 nm.

The particle size (average particle size) of the nanoparticles according to the invention is measured by, for example, an induced diffraction grating method. An induced diffraction grating method is a method of: (1) irradiating a 2 to 5 mg/mL aqueous solution of the block copolymer (C) of the invention with laser light, thereby forming diffraction gratings by dielectrophoresis; (2) stopping an external force that causes dielectrophoresis, measuring the annihilation rate of the diffraction gratings caused by diffusion, and (3) applying the annihilation rate to the Stokes-Einstein relational equation to obtain the particle size. For example, the particle size may be measured with a single nanoparticle size measuring apparatus, IG-1000, manufactured by Shimadzu Corp.

Since the block copolymer (C) of the invention is a block copolymer having a hydrophilic polyethylene glycol segment linked to a polyamino acid derivative segment exhibiting hydrophobicity by means of a physiologically active substance or another hydrophobic side chain, it is considered that the polyamino acid derivative segments of a plurality of the block copolymers will associate with one another in an aqueous solution based on hydrophobic interaction. As a result, it is speculated that the block copolymer (C) forms micelle-like associates having a core-shell structure in which the polyamino acid derivative segment forms the inner core (core part), and the hydrophilic polyethylene glycol segment covers the periphery of the inner core and forms an outer shell layer (shell part), and these micelle-like associates are observed as the nanoparticles described above.

The block copolymer (C) is preferably a block copolymer represented by General Formula (3):

[Chemical Formula 6]

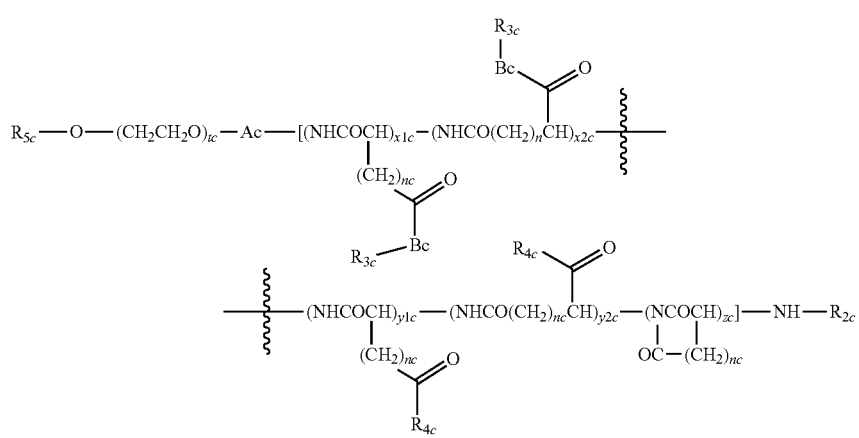

(3)

wherein $R_{5c}$ represents a hydrogen atom or a (C1-C6) alkyl group which may have a substituent; tc represents an integer from 20 to 140; Ac represents a (C1-C6) alkylene group which may have a substituent; $R_2$ represents a substituent selected from the group consisting of a hydrogen atom, a (C1-C6) acyl group, and a (C1-C6) alkoxycarbonyl group; $R_{3c}$ represents a bonding residue of a physiologically active substance having a hydroxy group and/or an amino group; $R_{4c}$ is a bonding residue of a hydrophobic substituent and represents one or more substituents selected from the group consisting of a linear, branched or cyclic (C1-C30) alkoxy group which may have a substituent, a linear, branched or cyclic (C1-C30) alkylamino group which may have a substituent, a linear, branched or cyclic (C1-C30) dialkylamino group which may have a substituent, a (C1-C8) alkylaminocarbonyl-(C1-C8) alkylamino group which may have a substituent, a bonding residue of a fluorescent substance having a hydroxy group and/or an amino group, and a hydroxy group; Bc represents a single bond or a divalent bonding group; nc represents 1 or 2; x1c, x2c, y1c, y2c, and zc each independently represent an integer from 0 to 20; (x1c+x2c) is an essential constituent and represents an integer from 1 to 20; (x1c+x2c+y1c+y2c+zc) represents an integer from 3 to 20; and the various constituent units to which $R_{3c}$ and $R_{4c}$ are bonded, and the constituent unit formed by intramolecular cyclization of a side-chain carbonyl group constitute a structure with those constituent units being each independently randomly arranged.

$R_{5c}$, tc, Ac, $R_{2c}$, nc, and Bc of General Formula (3) are the same as $R_5$, tb, Ab, $R_{2b}$, nb, and Bb of General Formula (2) described above, respectively. $R_{3c}$ of General Formula (3) is the same as the bonding residue of the physiologically active substance having a hydroxy group and/or an amino group mentioned as $R_{3a}$ of General Formula (1). $R_{4c}$ of General Formula (3) has the same meaning as the bonding residue of the hydrophobic substituent mentioned as $R_{3b}$ of General Formula (2)

In General Formula (3), x1c, x2c, y1c, y2c, and zc each represent the content of a constituent unit of an aspartic acid derivative unit and/or a glutamic acid derivative unit in the poly(aspartic acid and/or glutamic acid) chain of the block copolymer, and each represent an integer from 0 to 20. Furthermore, (x1c+x2c+y1c+y2c+zc) represents the number of polymerizations of the poly(aspartic acid and/or glutamic acid) chain and is an integer from 3 to 20. That is, the poly(aspartic acid and/or glutamic acid)) chain represents a polymer having an average number of polymerizations of 3 to 20. When this (x1c+x2c+y1c+y2c+zc) is smaller than 3, there is a risk that the block copolymer (C) may not have self-associating properties. On the other hand, when the number of polymerizations is larger than 20, there is a possibility that the molecular weight of the main chain polymer of the block copolymer thus obtainable may exceed 10 kilodaltons, and there is a risk that desired pharmacokinetic characteristics may not be provided. That is, when (x1c+x2c+y1c+y2c+zc), which is the number of polymerizations of the poly(aspartic acid and/or glutamic acid) chain, is out of the range of 3 to 20, there is a risk that an enhancement action of the pharmacologically action effect of the physiologically active substance and a side effect reducing effect may not be obtained. It is preferable that the number of polymerizations of the polyamino acid derivative is set as appropriate in consideration of the molecular weight of the block copolymer having a physiologically active substance bonded thereto. This (x1c+x2c+y1c+y2c+zc) is preferably an integer from 5 to 20.

The number of polymerizations of the polyamino acid derivative, (x1c+x2c+y1c+y2c+zc), may be determined by performing an analysis by $^1$H-NMR or by subjecting the polyethylene glycol-poly(aspartic acid and/or glutamic acid) block copolymer before having $R_{3c}$ and $R_{4r}$ bonded thereto, to neutralization titration.

In regard to General Formula (3), (x1c+x2c) represents the total number of aspartic acid units and/or glutamic acid units bonded to a physiologically active substance related to $R_{3c}$. The unit having a physiologically active substance bonded thereto is an essential configuration, and this (x1c+x2c) is an integer from 1 to 20. Preferably, this (x1c+x2c) is an integer from 2 to 20, and more preferably an integer from 3 to 15. The proportion of (x1c+x2c) with respect to (x1c+x2c+y1c+y2c+zc), which is the number of polymerizations of the poly(aspartic acid and/or glutamic acid) derivative) chain, is 4% to 100%. The proportion is preferably 10% to 90%, and more preferably 20% to 80%.

The content number of the aspartic acid unit and/or glutamic acid unit having a physiologically active substance bonded thereto, which is related to (x1c+x2c), is calculated from the amount of bonding of the physiologically active substance and the number of polymerizations of the poly (aspartic acid and/or glutamic acid) chain. The amount of bonding of the physiologically active substance may be determined by a method of cleaving the physiologically active substance from the block copolymer having the physiologically active substance and quantitatively analyzing the released physiologically active substance. A method of calculating the amount of bonding from the reaction ratio of the physiologically active substance at the time of producing the block copolymer having the physiologically active substance bonded thereto may also be used.

In regard to General Formula (3), (y1c+y2c) represents the total number of aspartic acid units and/or glutamic acid units, both having $R_{4c}$ bonded thereto. Furthermore, zc represents the total number of aspartic acid units and/or glutamic acid units, both having a structure in which a side-chain carboxy group has been intramolecularly cyclized. These are arbitrarily configured, and (y1c+y2c) and zc are each an integer from 0 to 18. Preferably, (y1c+y2c) and zc are each an integer from 1 to 15. The proportion of (y1c+y2c+zc) with respect to (x1c+x2c+y1c+y2c+zc), which is the number of polymerizations of the poly(aspartic acid and/or glutamic acid) derivative segment is 0% to 96%, and preferably 4% to 90%.

The content number of aspartic acid units and/or glutamic acid units having $R_{4c}$ bonded thereto, which is related to (y1c+y2c), is calculated from the amount of bonding of the substituents related to $R_{4c}$ and the number of polymerizations of the poly(aspartic acid and/or glutamic acid) segment. The amount of bonding of the substituent related to $R_{4c}$ may be determined by a method of cleaving the substituent related to $R_4$, from the block copolymer and quantitatively analyzing the released physiologically active substance. A method of calculating the reaction ratio of the substituent related to $R_4$, at the time of producing the block copolymer may also be used.

The amount of bonding may also be calculated from the integral values of 1H-NMR.

In regard to the block copolymer (C) having a physiologically active substance bonded thereto, as represented by General Formula (3) according to the invention, the poly (aspartic acid and/or glutamic acid) chain is a polymer segment in which an aspartic acid unit and/or a glutamic acid unit, both including $R_{2c}$ at a side-chain carboxy group, an aspartic acid unit and/or a glutamic acid unit, both including $R_{4c}$, and an aspartic acid unit and/or a glutamic acid unit, both having a structure with an intramolecularly cyclized side-chain carboxy group, exist as a mixture. Each of the constituent units exists in one or more units, the arrangement of the constituent units is not particularly controlled, and the polymer segment has a randomly arranged segment structure in which the constituent units are irregularly arranged.

It is preferable that the block copolymer (C) having a physiologically active substance bonded thereto, as represented by General Formula (3), has a mass content percentage of the physiologically active substance represented by $R_{3c}$ of not less than 5% by mass and not more than 60% by mass. Both in a case in which the content of the physiologically active substance is less than 5% by mass, and a case in which the content of the physiologically active substance is larger than 60% by mass, the hydrophilicity-hydrophobicity balance of the block copolymer having the physiologically active substance bonded thereto is significantly changed, and there is a risk that the block copolymer may not have appropriate self-associating properties and may not exhibit desired pharmacokinetics. The mass content percentage of the physiologically active substance is preferably not less than 5' by mass and not more than 50% by mass, and more preferably not less than 8% by mass and not more than 40% by mass.

The molecular weight of the main chain polymer combining the polyethylene glycol chain and the polyamino acid chain in the block copolymer having a physiologically active substance bonded thereto, as represented by General Formula (3), is not less than 2 kilodaltons and not more than 10 kilodaltons. Regarding this molecular weight, a calculated value obtained by summing the various constituent molecular weights of the constituent moieties excluding the bonding residue of the physiologically active substance, $R_{3c}$, and the bonding residue of an arbitrary hydrophobic substituent, $R_{4c}$, is employed as the molecular weight. That is, a calculated value obtained by summing the (1) molecular weight of the polyethylene glycol chain and the (2) molecular weight of the polyamino acid chain main chain portion is employed as the molecular weight.

The molecular weight of the block copolymer may be described with accuracy to the nearest kilodalton unit. In the following description, a preferable analysis method for the various constituent moieties will be described; however, any analysis method with sufficiently accurate for the measurement of the molecular weight of the polyamino acid derivative to the nearest kDa unit may be used without any particular limitations.

The (1) molecular weight of the polyethylene glycol chain is a measured value of the molecular weight of the polyethylene glycol compound that constructs the polyethylene glycol segment. The molecular weight that may be determined by the peak top molecular weight measured by a GPC method based on polyethylene glycol standards is employed. Regarding the calculated value, a value rounded off to the nearest hundred is used.

The (2) molecular weight of the main chain portion of the polyamino acid is a calculated value obtained by multiplying the molecular weight of the polymerization monomer unit of the polyamino acid chain included in the hydrophobic polymer segment by the average number of polymerizations. Regarding the number of polymerizations, a number of polymerizations obtained by a method of quantitatively determining the amount of side-chain carboxy groups of the polyamino acid by neutralization titration, or calculated from the integral values of the 1H-NMR, may be used. It is preferable to use a neutralization titration method.

The molecular weight of the main chain polymer combining the polyethylene glycol chain and the polyamino acid chain in the block copolymer having a physiologically active substance bonded thereto, as represented by General Formula (3), is not less than 2 kilodaltons and not more than 10 kilodaltons. When the molecular weight is smaller than 2 kilodaltons, a polymeric micelle type DDS preparation including the block copolymer (C) represented by General Formula (3) may not have a sufficient nanoparticle-forming ability and may not have sufficient migration characteristics, penetrability, and retention characteristics toward a target tissue. As a result, such DDS preparation may not efficiently exhibit a pharmacological action effect. Meanwhile, when the molecular weight is larger than 10 kilodaltons, kidney excretability is suppressed, and accordingly, the in vivo retention characteristics are enhanced. Therefore, since sensitization of a physiologically active substance may occur in a normal tissue other than a diseased target tissue, there is a risk of exhibition of disorders in the normal tissue. For example, in the case of using a cytotoxic physiologically active substance, prolongation of blood toxicity associated with bone marrow disorder may be considered. Therefore, it is necessary to control the molecular weight to a value of 10 kilodaltons or less. The molecular weight of the block copolymer is preferably not less than 2 kilodaltons and not more than 8 kilodaltons, and more preferably not less than 2 kilodaltons and not more than 7 kilodaltons.

The block copolymer (C) represented by General Formula (3) of the invention exhibits self-associating properties in an aqueous solution.

The particle size (average particle size) of the nanoparticles of the invention is preferably 30 nm or less, more preferably not less than 3 nm and not more than 30 nm, and particularly preferably not less than 3 nm and less than 20 nm.

The particle size (average particle size) of the nanoparticles according to the invention is measured by, for example, an induced diffraction grating method. An induced diffraction grating method is a method of: (1) irradiating a 2 to 5 mg/mL aqueous solution of the block copolymer (C) represented by General Formula (3) of the invention with laser light, thereby forming diffraction gratings by dielectrophoresis; (2) stopping an external force that causes dielectrophoresis, measuring the annihilation rate of the diffraction gratings caused by diffusion, and (3) applying the annihilation rate to the Stokes-Einstein relational equation to obtain the particle size. For example, the particle size may be measured with a single nanoparticle size measuring apparatus, IG-1000, manufactured by Shimadzu Corp.

[Composition Including Block Copolymer (A) and Block Copolymer (B), and Composition Including Block Copolymer (A) and Block Copolymer (C)]

The present invention relates to a technology of using a pharmacologically active substance as a carrier in a polymeric micelle type DDS preparation, and more particularly, the invention relates to a polymeric micelle type DDS preparation having a biometrics function and having an active targeting function. Therefore, a DDS preparation including the block copolymer (A) provided with a target binding site is a first embodiment of the invention. Furthermore, a composition including the block copolymer (A) having a target binding site and the block copolymer (B) that does not have a target binding site is a second embodiment of the invention. Furthermore, separately, a composition including the block copolymer (A) having a target binding site and the block copolymer (C) as a polymeric prodrug that does not have a target binding site is a third embodiment of the invention. These are amphiphilic block copolymers, and hydrophobic polymer segments of the block copolymers have associating properties based on hydrophobic interaction and form nanoparticles in an aqueous solution. That is, even if there are block copolymers having different chemical structures as a mixture of the block copolymer (A), the block copolymer (B), and/or the block copolymer (C), an interaction between hydrophobic polymer segments occurs, and the block copolymers form nanoparticle-like associates in which these hydrophobic polymer segments exist as a mixture. As a result, a physiologically active substance is incorporated into the inner core (core) part of the nanoparticle-like associates by chemical bonding or physical adsorption action, the outer shell (shell) part is provided with a target binding site, and thus resultant may be utilized as a polymeric micelle type DDS preparation having an active targeting function.

In regard to the composition including the copolymers (A) and (B), which is the second embodiment of the invention, even if the block copolymer does not include a physiologically active substance bonded to the copolymers, the composition may be used as a physically adsorbed type micelle DDS preparation retaining a physiologically active substance by physical adsorption action.

In the case of a composition including the copolymers (A) and (C), which is the third embodiment of the invention, since the block copolymer (C) is a polymer prodrug, the composition may be used as a chemically bonded type micelle DDS preparation.

In the composition of the invention, the block copolymer (A) and the block copolymer (B), the block copolymer (A) and the block copolymer (C), and the block copolymer (A) and (a mixed formulation of the block copolymer (B) and the block copolymer (C)) may exist at any arbitrary appropriate ratios. It is preferable that one or more molecules of the block copolymer (A) that is in charge of an active targeting function are included in the nanoparticle associates formed by the block copolymers according to the present invention. In regard to the block copolymers according to the invention, the molar contents by considering the block copolymer as polymer molecules may be calculated, and the composition of the invention may be expressed in the molar ratio of the block copolymer (A) and the block copolymer (B) and/or block copolymer (C).

A suitable molar ratio of mixing the block copolymer (A) and the block copolymer (B) and/or block copolymer (C) ((A):(B) and/or (C)) is 1:0.1 to 30. The molar ratio is more preferably 1:0.5 to 20, and it is particularly preferable to produce the composition at 1:1 to 10. In the composition of the invention, any block copolymer that is none of the block copolymer (A), the block copolymer (B), and the block copolymer (C) may exist at any arbitrary appropriate ratio. Examples thereof include block copolymers that have been unreacted or that are inevitably existing side-products or decomposition products, occurring during the production of the block copolymers (A), (B), and (C). These block copolymers may exist to the extent that does not affect the physical properties of the composition of the invention. The existence ratio in terms of a molar ratio (total molar amount of block copolymer (A)+block copolymer (B)+block copolymer (C):total molar amount of other block copolymers) is 1:0 to 2, and preferably 1:0 to 0.5, and more preferably 1:0 to 0.25.

The composition of the invention may include, for example, embodiments of the following four combinations.

(Composition 1) Block copolymer (A) and block copolymer (B)
(Composition 2) Block copolymer (A) and block copolymer (C)
(Composition 3) Block copolymer (A), block copolymer (B), and a physiologically active substance
(Composition 4) Block copolymer (A), block copolymer (B), and block copolymer (C)

These compositions become associative compositions due to interactions between the block copolymers. For example, the following three types of production methods may be mentioned.

(1) A method of mixing the block copolymers in an aqueous solution and causing the block copolymers to self-assemble into a micelle form.

(2) A method of dissolving the block copolymers in an organic solvent and then dialyzing the solution.

(3) A method of dissolving the block copolymers in an organic solvent, mixing the solution to become uniform, distilling off the solution under reduced pressure to obtain a film of the polymers, adding water to the film, mixing the film and water, and causing the polymers to self-assemble into a micelle form.

The composition of the invention may also be produced by producing the following three kinds of compositions and then reacting the compositions with a compound having a target binding site. That is, (Precursor composition 1) Block copolymer (A) precursor and block copolymer (B) or block copolymer (C)
(Precursor composition 2) Block copolymer (A) precursor, block copolymer (B), and a physiologically active substance
(Precursor composition 3) Block copolymer (A) precursor, block copolymer (B), and block copolymer (C)

Production of solutions of the above-mentioned precursor compositions (1) to (3) is carried out, and for example, the following two types of production methods may be mentioned.

(1) Any one of the precursor compositions (1) to (3) is dissolved in an organic solvent, the solution is mixed to become uniform, the solution is distilled off under reduced pressure, and a film of polymers is obtained. Water is added to this, the film and water are mixed, and the polymers are caused to self-assemble into a micelle form. A method of subsequently bonding a compound having a target binding site to a block copolymer (A) precursor (block copolymer (A) before reacting with the compound having a target binding site), and producing a composition according to the present invention.

(2) Any one of the precursor compositions (1) to (3) is mixed in an aqueous solution, and the polymers are caused to self-assemble into a micelle form. A method of subsequently bonding a compound having a target binding site to a block copolymer (A) precursor (block copolymer (A) before reacting with the compound having a target binding site), and producing a composition according to the present invention.

Examples of the organic solvent used for producing the above-described compositions include methanol, acetone, acetonitrile, and dimethylformamide.

An aqueous solution for producing the above-described composition may be formed by, for example, adding a water-miscible organic solvent such as ethanol or dimethyl sulfoxide, and a known buffering agent to purified water.

A composition including the block copolymer (A) and the block copolymer (B) of the invention, and a composition including the block copolymer (A) and the block copolymer (C) exhibit self-associating properties in an aqueous solution.

The particle size (average particle size) of the nanoparticles of the compositions according to the invention is preferably 30 nm or less, more preferably not less than 3 nm and not more than 30 nm, and particularly preferably not less than 3 nm and less than 20 nm.

The particle size (average particle size) of the nanoparticles according to the present invention is measured by, for example, an induced diffraction grating method. An induced diffraction grating method is a method of: (1) irradiating a 2 to 5 mg/mL aqueous solution of a composition including the block copolymer (A) and the block copolymer (B) of the invention or a composition including the block copolymer (A) and the block copolymer (C) of the invention with laser light, thereby forming diffraction gratings by dielectrophoresis; (2) stopping an external force that causes dielectrophoresis, measuring the annihilation rate of the diffraction gratings caused by diffusion, and (3) applying the annihilation rate to the Stokes-Einstein relational equation to obtain the particle size. For example, the particle size may be measured with a single nanoparticle size measuring apparatus, IG-1000, manufactured by Shimadzu Corp.

Since the composition including the block copolymer (A) and the block copolymer (B) of the invention, and the composition including the block copolymer (A) and the block copolymer (C) are compositions including a block copolymer having a hydrophilic polyethylene glycol segment linked to a polyamino acid derivative segment that exhibits hydrophobicity by means of a physiologically active substance or another hydrophobic side chain, it is considered that the polyamino acid derivative segments of a plurality of block copolymers will associate with one another in an aqueous solution based on hydrophobic interaction. As a result, it is speculated that the composition forms micelle-like associates having a core-shell structure in which the polyamino acid derivative segment forms an inner core (core part), and the hydrophilic polyethylene glycol segment covers the periphery of the inner core and forms an outer shell layer (shell part), and these micelle-like associates are observed as the nanoparticles described above.

Next, methods for producing the block copolymers (A), (B), and (C) according to the present invention will be explained.

First, methods for producing the block copolymer (B) and the block copolymer (C) will be explained. In this regard, a method of synthesizing a block copolymer having a polyethylene glycol chain, which is a hydrophilic polymer segment, linked to a polyamino acid chain containing aspartic acid and/or glutamic acid, which constitutes the main chain of a hydrophobic polymer segment, and producing a compound by incorporating a physiologically active substance and/or a hydrophobic substituent into the block copolymer by a condensation reaction, may be mentioned. Furthermore, a method of linking a hydrophilic polymer segment containing a polyethylene glycol chain to a polyamino acid chain having a physiologically active substance and/or a hydrophobic substituent bonded thereto, and constructing a block copolymer, may be mentioned. A method of synthesizing in advance the above-described block copolymer having a polyethylene glycol segment linked to a polyamino acid segment, and incorporating a physiologically active substance or a hydrophobic substituent into this block copolymer by a condensation reaction, is preferred.

Examples of the method for producing a block copolymer having a polyethylene glycol chain linked to a polyamino acid chain include a method of polymerizing a compound containing a polyethylene glycol segment with amino acid-N-carboxyanhydrides in sequence and thereby constructing a polyamino acid chain; and a method of bonding a polyethylene glycol segment and a polyamino acid derivative. Since the amino acid-N-carboxyanhydrides have high reactivity and the number of polymerizations of the polyamino acid is easily controllable, it is preferable to use the former method.

One embodiment for the production method of obtaining a block copolymer according to the present invention by synthesizing in advance a block copolymer having a polyethylene glycol chain linked to a polyamino acid derivative, and bonding a physiologically active substance having a hydroxy group and/or an amino group, or a hydrophobic substituent to the block copolymer, will be described.

First, a polyethylene glycol derivative having an amino group at one terminal (for example, methoxy polyethylene glycol-1-propylamine) is sequentially reacted with amino acid-N-carboxyanhydrides in which a side-chain functional group of the amino acid is appropriately protected, and the skeleton of a block copolymer having a polyethylene glycol segment linked to a polyamino acid segment is constructed in sequence by polymerization. In this case, aspartic acid and/or glutamic acid may be incorporated into the polyamino acid segment by appropriately incorporating aspartic acid-N-carboxyanhydride and/or glutamic acid-N-carboxyanhydride, both having a protected side-chain carboxy group, as the amino acid-N-carboxyanhydride. Subsequently, an appropriate deprotection reaction is carried out, and thus the block copolymer containing aspartic acid and/or glutamic acid, in which the side-chain carboxy group has been deprotected, may be synthesized. Regarding the deprotection reaction, in a case in which the side-chain carboxy group is a benzyl ester, a deprotection reaction may be carried out by hydrolysis under alkaline conditions or by a hydrogenolysis reaction.

It is desirable that this polyethylene glycol-polyamino acid block copolymer is reacted with a physiologically active substance having an amino group and/or a hydroxy group, or with a hydrophobic substituent, under condensation reaction conditions in an appropriate reaction solvent.

In the condensation reaction between the polyethylene glycol-polyamino acid block copolymer and a physiologically active substance or a hydrophobic substituent, regarding the solvent that may be used, any solvent in which both the compounds are dissolved may be used without any particular limitations. For example, water-soluble organic solvents such as N,N-dimethylformamide (DMF), N-methylpyrrolidone (NMP), and 1,3-dimethyl-2-imidazolidinone (DMI) may be mentioned. These solvents may be used singly or may be used as mixed solvents thereof. Furthermore, mixed solvents of the above-described solvents with other organic solvents may also be used.

Furthermore, regarding the condensing agent to be used, any conventional dehydration condensing agent that causes an esterification reaction based on a dehydration condensation reaction between a carboxylic acid and a hydroxy group, and/or an amidation reaction based on a dehydration condensation reaction between a carboxylic acid and an amino group, may be used without any particular problem. Such condensing agent includes carbodiimide-based condensing agents such as dicyclohexylcarbodiimide (DCC), diisopropylcarbodiimide (DIPCI), and 1-ethyl-3-(3-dimethylaminopropyl)carbodiimide hydrochloride (WSC); triazine-based condensing agents such as 4-(4,6-dimethoxy-1,3,5-triazin-2-yl)-4-methylmorpholium chloride n-hydrate (DMT-MM); 1-ethoxycarbonyl-2-ethoxy-1,2-dihydroquinoline (EEDQ), and di-tert-butyl dicarbonate ($Boc_2O$) may be used. At the time of the condensation reaction, reaction aids such as 4-dimethylaminopyridine (DMAP), 1-hydroxybenzotriazole (HOBt), and N-hydroxysuccinimide (HOSu) may also be used. When a carbodiimide-based condensing agent is used, a (C1-C8) alkylaminocarbonyl-(C1-C8) alkylamino group which may have a substituent may be introduced simultaneously with a physiologically active substance or a hydrophobic substituent.

Regarding the reaction temperature, the condensation reaction may be carried out usually at a temperature of 0° C. to 180° C., and preferably 5° C. to 100° C.

A hydrophobic substituent such as the (C1-C30) alkoxy group, the (C1-C30) alkylamino group, or the di(C1-C30) alkylamino group is introduced into the polyamino acid chain for the purpose of adjusting the self-associating properties of the block copolymer of the invention. Regarding the method, a method of activating carboxy groups of the polyethylene glycol-polyamino acid copolymer by adding a condensing agent, and then reacting the polyethylene glycol-polyamino acid copolymer with a compound corresponding to the hydrophobic substituent that is wished to be introduced, at a desired equivalent; or a method of activating a compound corresponding to a hydrophobic substituent and then reacting the compound with the polyamino acid segment of the copolymer, may be mentioned.

In this case, the physiologically active substance may be introduced after the hydrophobic substituent is introduced, or the reverse is also acceptable. It is also acceptable that the physiologically active substance and the hydrophobic substituent are simultaneously introduced. The hydrophobic substituent may be a substituent of a single kind or a plurality of kinds of substituents.

The block copolymer of the invention may be produced by introducing a physiologically active substance and an arbitrary hydrophobic substituent into a polyethylene glycol-polyamino acid block copolymer, and then optionally performing conventional separation operations or purification operations.

Next, a method for producing the block copolymer (A) will be explained below.

The block copolymer (A) is produced from a block copolymer having a polyethylene glycol segment and a polyamino acid segment containing aspartic acid and/or glutamic acid. Regarding the construction method, it is possible to use any method among a method of linking a polyethylene glycol segment to a polyamino acid segment containing aspartic acid and/or glutamic acid, and a method of sequentially polymerizing aspartic acid and/or glutamic acid with a polyethylene glycol segment several times.

Regarding the latter method, there may be mentioned a method of sequentially reacting, for example, a commercially available polyethylene glycol modified with N-(tert-butoxycarbonyl)aminoethyl group at one terminal and aminoethyl group at another terminal, with an amino acid-N-carboxyanhydride in which a side-chain functional group of an amino acid is appropriately protected, and constructing the skeleton of a block copolymer having a polyethylene glycol segment linked to a polyamino acid segment, successively by polymerization, by applying the method described in JPH05-955 A or the like. In this case, aspartic acid and/or glutamic acid may be incorporated into the polyamino acid segment by incorporating aspartic acid-N-carboxyanhydride and/or glutamic acid-N-carboxyanhydride, both having an appropriately protected side-chain carboxy group, as the amino acid-N-carboxyanhydride. Thereafter, the block copolymer is subjected to an appropriate deprotection reaction, and thus the block copolymer containing aspartic acid and/or glutamic acid, in which the side-chain carboxy group has been deprotected, may be synthesized. Regarding the deprotection reaction, in a case in which the side-chain carboxy group is a 3-benzyl ester, a deprotection reaction may be carried out by performing hydrolysis under alkaline conditions, or a hydrogenolysis reaction. Then, this polyethylene glycol-polyamino acid block copolymer may be reacted with a physiologically active substance having an amino group and/or a hydroxy group, or with a hydrophobic substituent, in an appropriate reaction solvent under condensation reaction conditions, as in the case of the block copolymers (B) and (C) represented by General Formula (2) and General Formula (3).

Next, the protective group of the terminal amino group of the polyethylene glycol structural moiety of the block copolymer, for example, a tert-butoxycarbonyl group, is deprotected in order to introduce a target binding site, and the amino group is bonded to GMBS (N-(4-maleimidobutyryloxy)succinimide) by an amide bond. A disulfide bond that exists in a compound such as a protein, a peptide, or a sugar chain is reduced as necessary, and the reduction product is bonded to the maleimide group thus obtained, via a sulfhydryl group. Thereby, the block copolymer (A) represented by General Formula (1) may be produced.

The method for producing this block copolymer (A) represented by General Formula (1) is not limited to the above-described methods. A protective group (for example, a tert-butoxycarbonyl group) of a terminal amino group of the polyethylene glycol structural moiety of the block copolymer is eliminated, subsequently a (thio)carboxylic acid derivative having a protected terminal thiol group is bonded to the block copolymer by an amide bond, and subsequently the protective group of the terminal thiol group is eliminated. Meanwhile, the block copolymer (A) may also be produced by a method of bonding an amino group of lysine or the like existing in a compound such as a protein, a peptide, or a sugar chain to a carboxylic acid derivative having a terminal maleimide group by an amide bond, and subjecting the maleimide group of the compound thus obtained and the above-described thiol compound (obtained by eliminating the protective group of a terminal thiol group) to an addition reaction.

In addition to that, the block copolymer (A) may be produced using a method of reacting an amino group of lysine existing in a compound such as a protein, a peptide, or a sugar chain with a terminal of the polyethylene glycol structural moiety having an α-haloamide group; a method of introducing an azide group or an acetylene group into a terminal of a compound such as a protein, a peptide, or a sugar chain and a terminal of the polyethylene glycol structural moiety, and using a Click reaction; or the like. After a target binding site and polyethylene glycol are bonded, if necessary, unreacted active reactive groups are deactivated (for example, a maleimide group as an active reactive group is reacted with cysteine), or binding stability with a target compound is attempted by actively ring-opening a cyclic imide group in order to avoid the Retro-Michael reaction by which a target compound is released, and the block copolymer (A) may be produced via purification processes.

The block copolymer (A), a composition including the block copolymer (A) and the block copolymer (B), and a composition including the block copolymer (A) and the block copolymer (C), all including a physiologically active substance, of the invention, slowly release the included physiologically active substance after being administered into the living body. The released physiologically active substance may exhibit pharmacological effects. Therefore, the block copolymer (A), a composition including the block copolymer (A) and the block copolymer (B), and a composition including the block copolymer (A) and the block copolymer (C), all including a physiologically active substance, may be used as pharmaceutical products containing the physiologically active substance as an active ingredient.

In a case in which the block copolymer (A), a composition including the block copolymer (A) and the block copolymer (B), and a composition including the block copolymer (A) and the block copolymer (C), all including a physiologically active substance, of the invention, is used as a pharmaceutical product, the pharmaceutical product may be used by any of oral and parenteral administration routes. It is preferable that the pharmaceutical products are prescribed via an administration route based on parenteral injection. Administration by injection is carried out by intravenous administration, intraarterial administration, subcutaneous administration, intramuscular administration, intratumoral administration, or the like.

In regard to the formulation of the block copolymer (A), a composition including the block copolymer (A) and the block copolymer (B), and the composition including the block copolymer (A) and the block copolymer (C), all including a physiologically active substance, of the present invention, pharmacologically acceptable carriers that are conventionally used, for example, an excipient, an extending agent, a filler, a binding agent, a wetting agent, a disintegrant, a lubricating agent, a surfactant, a dispersant, a buffering agent, a preservative, a dissolution aid, an antiseptic agent, a flavoring agent, a soothing agent, a stabilizer, a solvent, a solvating agent, a suspending agent, a colorant, a fragrance, and an isotonizing agent may be used.

In the case of an injectable preparation, a solvent is usually used. Examples of the solvent include water, physiological saline, a 5% glucose or mannitol solution, a water-soluble organic solvent such as, for example, glycerol, ethanol, dimethyl sulfoxide, N-methylpyrrolidone, polyethylene glycol, or Cremophor, mixed liquids thereof, and a mixed liquid of water and the water-soluble organic solvent. It is preferable to produce an administrable pharmaceutical preparation using these additives for formulation, and to use the pharmaceutical preparation.

The dosage amount of administration of the block copolymer (A), a composition including the block copolymer (A) and the block copolymer (B), or a composition including the block copolymer (A) and the block copolymer (C), all including a physiologically active substance, of the invention may certainly vary depending on the type of the physiologically active substance to be bonded, and the gender, age, physiological condition, and pathologic condition of the patient, and the like. However, it is preferable that the block copolymer or the composition is parenterally administered usually in an amount of 0.01 to 500 mg/m$^2$, and preferably 0.1 to 250 mg/m$^2$, in terms of the active ingredient, per day for an adult.

EXAMPLES

Hereinafter, the present invention will be explained in more detail by way of Examples. However, the invention is not intended to be limited to these Examples.

The measurement of the volume-based particle sizes of the block copolymers (A) according to Examples 1-1, 1-2, and 2 was carried out using a particle size/zeta potential analyzer, Zetasizer Nano ZS, manufactured by Malvern Panalytical, Ltd. (measurement temperature: 25° C., analysis model: General purpose (normal resolution), material RI: 1.59).

Regarding a sample for measuring the volume-based particle size, ultrapure water was added to a physiologically active substance-bonded block copolymer so as to obtain a block copolymer concentration of 1 mg/mL, the block copolymer was dissolved therein under ice cooling by ultrasonication, and a solution obtained by filtering the solution through a 0.45-µm membrane filter was used.

The measurement of the average particle size of the compositions including block copolymers of Examples 3 to 10 and Comparative Examples 1 to 6 was carried out using a single nanoparticle size analyzer, IG-1000, manufactured by Shimadzu Corp. (measurement temperature: 25° C., light intensity at t=0: 100 to 200).

Regarding a sample for measuring the average particle size, a solution produced to have a concentration of 2 mg/mL or 5 mg/mL in terms of the composition weight and filtered through a 0.45-µm membrane filter, was used.

Synthesis Example 1

Synthesis of polyethylene glycol-polyglutamic acid block copolymer (polyethylene glycol molecular weight: 10 kilodaltons, number of polymerizations of polyglutamic acid: 21.0)

A polyethylene glycol having one terminal methoxy group and another terminal 3-aminopropyl group (SUNBRIGHT M141573, manufactured by NOF CORPORATION, average molecular weight: 10 kilodaltons, 9.0 g) was dissolved in DMSO (180 mL), and then γ-benzyl L-glutamic acid-N-carboxyanhydride (5.7 g) was added thereto. The mixture was stirred for 21.0 hours at 30° C. The reaction liquid was added dropwise for 0.5 hour into a mixed liquid of diisopropyl ether (2,880 mL) and ethanol (720 mL), and the mixture was stirred for one hour at room temperature. Subsequently, the supernatant was removed, and a mixed solution of diisopropyl ether (1,440 mL) and ethanol (360 mL) was added to the residue. The mixture was stirred for one hour, and then a precipitate was collected by filtration and dried under reduced pressure. Thus, a polymerization product (12.4 g) was obtained.

The polymerization product (12.0 g) thus obtained was dissolved in DMF (198 mL), acetic anhydride (2.4 mL) was added thereto, and the mixture was stirred for 23.5 hours at 20° C. The reaction liquid was added dropwise for 0.5 hour into a mixed liquid of diisopropyl ether (1,600 mL) and ethyl acetate (400 mL), and the mixture was stirred for one hour at room temperature. Subsequently, the supernatant was removed, a mixed solution of diisopropyl ether (800 mL) and ethanol (200 mL) was added to the residue, and the mixture was stirred for one hour. Subsequently, a precipitate was collected by filtration and dried under reduced pressure, and thereby an acetylated polymer (10.7 g) was obtained.

The acetylated polymer (10.7 g) thus obtained was dissolved in DMF (230 mL), and 10% palladium-carbon (2.2 g) was added thereto. Subsequently, the reaction atmosphere was purged with hydrogen, and hydrogenolysis was performed for 43.5 hours at 30° C. and 1 atmosphere. The 10% palladium-carbon catalyst was separated by filtration (240 mL of ethyl acetate was used for washing down), subsequently the filtrate was added dropwise for 1.5 hours into a mixed liquid of heptanes (1,965 mL) and ethyl acetate (715 mL), and the mixture was stirred for 2.5 nights at room temperature. Subsequently, the supernatant was removed, a mixed liquid of heptanes (833 mL) and ethyl acetate (417 mL) was added to the residue, and the mixture was stirred for 0.5 hour. Subsequently, a precipitate was collected by filtration and dried under reduced pressure. This precipitate (9.0 g) was dissolved in 5% saline (900 mL), and the pH of the solution was adjusted to about 11 using a 1 N aqueous solution of sodium hydroxide. Subsequently, the solution was purified using partition/adsorption resin column chromatography (HP20) and then using ion exchange resin column chromatography (Dowex 50). The eluted solution was concentrated under reduced pressure and then freeze-dried, and thereby a polyethylene glycol-polyglutamic acid block copolymer (Synthesis Example 1 7.4 g) was obtained.

The number of polymerizations of glutamic acid in Synthesis Example 1 was calculated to be 21.0 by a titration method using 0.1 N potassium hydroxide.

Synthesis Example 2

Synthesis of polyethylene glycol-polyglutamic acid block copolymer (polyethylene glycol molecular weight: 2 kilodaltons, number of polymerizations of polyglutamic acid: 7.9)

A polyethylene glycol having one terminal methoxy group and another terminal 3-aminopropyl group (SUNBRIGHT M89506, manufactured by NOF Corp., average molecular weight: 2 kilodaltons, 14 g) was dissolved in DMSO (280 mL), subsequently γ-benzyl L-glutamic acid-N-carboxyanhydride (16.8 g) was added thereto, and the mixture was stirred for 22.5 hours at 30° C. The reaction liquid was added dropwise for 2.0 hours into a mixed liquid of diisopropyl ether (5,040 mL) and ethanol (560 mL), and the mixture was stirred for 4.0 hours at room temperature. Subsequently, the supernatant was removed, a mixed solution of diisopropyl ether (1,800 mL) and ethanol (200 mL) was added to the residue, and the mixture was stirred. A precipitate was collected by filtration and dried under reduced pressure. Thus, a polymerization product (31.9 g) was obtained.

The polymerization product (30.0 g) thus obtained was dissolved in DMF (336 mL), acetic anhydride (6.0 mL) was added thereto, and the mixture was stirred for 18 hours at 20° C. The reaction liquid was added dropwise for 2.5 hours into a mixed liquid of diisopropyl ether (3,024 mL) and ethyl acetate (336 mL), and the mixture was stirred for 6.0 hours at room temperature. Subsequently, the supernatant was removed, a mixed solution of diisopropyl ether (1,800 mL) and ethanol (200 mL) was added to the residue, and the mixture was stirred for 1.5 hours. Subsequently, a precipitate was collected by filtration and dried under reduced pressure, and thereby, an acetylated polymer (23.7 g) was obtained.

The acetylated polymer (22.0 g) thus obtained was dissolved in DMF (515 mL), and 10% palladium-carbon (4.4 g) was added thereto. Subsequently, the reaction atmosphere was purged with hydrogen, and hydrogenolysis was performed for 65 hours at 30° C. and 1 atmosphere. The 10% palladium-carbon catalyst was separated by filtration (200 mL of ethyl acetate was used for washing down), subsequently the filtrate was added dropwise for 1.5 hours into a mixed liquid of heptanes (3,000 mL) and ethyl acetate (1,200 mL), and the mixture was stirred for 5.0 nights at room temperature. Subsequently, the supernatant was removed, a mixed liquid of heptane (1,333 mL) and ethyl acetate (667 mL) was added to the residue, and the mixture was stirred for 0.5 hour. Subsequently, a precipitate was collected by filtration and dried under reduced pressure. This precipitate (15.0 g) was dissolved in 5% saline (1,500 mL), and the pH of the solution was adjusted to about 11 with a 2.2 N aqueous solution of sodium hydroxide. Subsequently, the solution was purified using partition/adsorption resin column chromatography (HP-20) and then using ion exchange resin column chromatography (Dowex 50). The solution thus eluted was concentrated under reduced pressure and then freeze-dried, and thereby a polyethylene glycol-polyglutamic acid block copolymer (Synthesis Example 2: 12.3 g) was obtained.

The number of polymerizations of glutamic acid in Synthesis Example 2 was calculated to be 7.9 by a titration method using 0.1 N potassium hydroxide.

[Synthesis Example 3] (Comparative Example of Block Copolymer (B))

Synthesis of 4-phenyl-1-butanol-bonded and 2-(2-aminoethoxy)-9-(diethylamino)-5H-benzo[a]phenoxazin-5-one-bonded product of polyethylene glycol (10 kilodaltons)-polyglutamic acid (21.0 polymerizations) block copolymer The product of Synthesis Example 1 (500 mg), 2-(2-aminoethoxy)-9-(diethylamino)-5H-benzo[a]phenoxazin-5-one (manufactured by Tokyo Chemical Industry Co., Ltd., 14.9 mg), and 4-dimethylaminopyridine (DMAP, 101 mg) were dissolved in DMF (6.6 mL), and diisopropylcarbodiimide (DIPCI, 12 μL) was added thereto. The mixture was stirred for 5 hours at 25° C. Subsequently, 4-phenyl-1-butanol (85.0 μL) and diisopropylcarbodiimide (DIPCI, 253 μL) were added thereto, and the mixture was stirred for 16 hours. Subsequently, diisopropylcarbodiimide (DIPCI, 127 μL) was further added thereto, and the mixture was stirred for one hour. The reaction liquid was added dropwise for 20 minutes into a mixed liquid of diisopropyl ether (96 mL), ethanol (12 mL), and ethyl acetate (12 mL), and the mixture was stirred for one hour at room temperature. Subsequently, a precipitate was collected by filtration and dried under reduced pressure, and thus a crude product was obtained. The crude product thus obtained was dissolved in acetonitrile/water (50/50 (v/v), 20 mL), and then an ion exchange resin (Dowex 50) was added thereto. The mixture was stirred for 2.5 hours at room temperature. The ion exchange resin was separated by filtration, and then acetonitrile was distilled off under reduced pressure. The residue was freeze-dried, and thereby the titled 4-phenyl-1-butanol-bonded block copolymer (Synthesis Example 3: 514 mg) was obtained.

The product of Synthesis Example 3 was subjected to a hydrolysis treatment using a 1 N aqueous solution of sodium hydroxide, and the amount of 4-phenyl-1-butanol thus released was quantitatively determined by high performance liquid chromatography (HPLC). Thus, the content of 4-phenyl-1-butanol was determined. As a result, the content of 4-phenyl-1-butanol in Synthesis Example 3 was 10.2% by mass.

The amount of bonding of 2-(2-aminoethoxy)-9-(diethylamino)-5H-benzo[a]phenoxazin-5-one in Synthesis Example 3 was 1.0 molecule, as determined from the consumption rate of 2-(2-aminoethoxy)-9-(diethylamino)-5H-benzo[a]phenoxazin-5-one in the reaction solution measured by high performance liquid chromatography (HPLC). Therefore, the total molecular weight of 2-(2-aminoethoxy)-9-(diethylamino)-5H-benzo[a]phenoxazin-5-one in Synthesis Example 3 was calculated to be 377≈0.4 kDa.

From these values, the total molecular weight of Synthesis Example 3 was calculated to be 15,700≈16 kDa.

The molecular weight of the main chain polymer combining a polyethylene glycol chain and a polyamino acid chain in Synthesis Example 3 was 12,753≈12 kDa, from the sum of the molecular weight of the polyethylene glycol chain (10,000), the molecular weight of the glutamic acid 21.0 polymerizations (129.11×21.0=2,711), and the molecular weight of the acetyl group at the polyamino acid terminal (42).

Furthermore, the content of 2-(2-aminoethoxy)-9-(diethylamino)-5H-benzo[a]phenoxazin-5-one in Synthesis Example 3 was 2.4% by mass, the content of 4-phenyl-1-butanol was 10.2% by mass, and the content of the polyethylene glycol segment was 64% by mass.

[Synthesis Example 4] (Block Copolymer (B))

Synthesis of 4-phenyl-1-butanol-bonded and 2-(2-aminoethoxy)-9-(diethylamino)-5H-benzo[a]phenoxazin-5-one-bonded product of polyethylene glycol (2 kilodaltons)-polyglutamic acid (7.9 polymerizations) block copolymer The product of Synthesis Example 2 (1,000 mg), 2-(2-aminoethoxy)-9-(diethylamino)-5H-benzo[a]phenoxazin-5-one (manufactured by Tokyo Chemical Industry Co., Ltd., 46.9 mg), and 4-dimethylaminopyridine (DMAP, 315 mg) were dissolved in DMF (21 mL), and diisopropylcarbodiimide (DIPCI, 38 µL) was added thereto. The mixture was stirred for 5 hours at 25° C. Subsequently, 4-phenyl-1-butanol (266 µL) and diisopropylcarbodiimide (DIPCI, 794 µL) were added thereto, and the mixture was stirred for 15 hours. Subsequently, diisopropylcarbodiimide (DIPCI, 397 µL) was further added thereto, and the mixture was stirred for 5.5 hours. The reaction liquid was transferred into a dialysis membrane having a MWCO of 1.0 kDa, and dialysis was performed using water as the external liquid. The internal liquid was freeze-dried, and thereby a product was obtained. The product thus obtained was dissolved in acetonitrile/water (50/50 (v/v), 50 mL), and then the solution was transferred into a dialysis membrane having a MWCO of 1.0 kDa. Dialysis was performed using acetonitrile/water (50/50 (v/v)) as the external liquid. Subsequently, dialysis was performed using acetonitrile as the external liquid. After completion of the dialysis, water was added to the internal liquid so that the internal liquid would become acetonitrile/water (50/50 (v/v)), and an ion exchange resin (Dowex 50) was added to the internal liquid. The mixture was stirred for 0.5 hours at room temperature. The ion exchange resin was separated by filtration, and then acetonitrile was distilled off under reduced pressure. The residue was freeze-dried, and thereby the titled 4-phenyl-1-butanol-bonded block copolymer (Synthesis Example 4: 1,012 mg) was obtained.

The product of Synthesis Example 4 was subjected to a hydrolysis treatment using a 1 N aqueous solution of sodium hydroxide, and the amount of 4-phenyl-1-butanol thus released was quantitatively determined by high performance liquid chromatography (HPLC). Thus, the content of 4-phenyl-1-butanol was determined. As a result, the content of 4-phenyl-1-butanol in Synthesis Example 4 was 15.9% by mass.

The amount of bonding of 2-(2-aminoethoxy)-9-(diethylamino)-5H-benzo[a]phenoxazin-5-one in Synthesis Example 4 was 0.37 molecules, as determined from the consumption rate of 2-(2-aminoethoxy)-9-(diethylamino)-5H-benzo[a]phenoxazin-5-one in the reaction solution measured by high performance liquid chromatography (HPLC). Therefore, the total molecular weight of 2-(2-aminoethoxy)-9-(diethylamino)-5H-benzo[a]phenoxazin-5-one in Synthesis Example 4 was calculated to be 138≈0.1 kDa.

From these values, the total molecular weight of Synthesis Example 4 was calculated to be 4,169≈4 kDa.

The molecular weight of the main chain polymer combining the polyethylene glycol chain and the polyamino acid chain in Synthesis Example 4 was 3,062≈3 kDa, from the sum of the molecular weight of the polyethylene glycol chain (2,000), the molecular weight of the glutamic acid 7.9 polymerizations (129.11×7.9=1,020), and the molecular weight of the acetyl group at the polyamino acid terminal (42).

Furthermore, the content of 2-(2-aminoethoxy)-9-(diethylamino)-5H-benzo[a]phenoxazin-5-one in Synthesis Example 4 was 3.3% by mass, the content of 4-phenyl-1-butanol was 15.9% by mass, and the content of the polyethylene glycol segment was 48% by mass.

[Synthesis Example 5] (Comparative Example of Block Copolymer (C))

Synthesis of 7-ethyl-10-hydroxycamptothecin (EHC)-bonded and 2-(2-aminoethoxy)-9-(diethylamino)-5H-benzo[a]phenoxazin-5-one-bonded product of polyethylene glycol (12 kilodaltons)-polyglutamic acid (22.0 polymerizations) block copolymer A polyethylene glycol (12 kilodaltons)-polyglutamic acid (22.0 polymerizations) block copolymer (4,100 mg) synthesized by a method similar to the methods of Synthesis Example 1 and Synthesis Example 2 was dissolved in DMF (65 mL), and then 2-(2-aminoethoxy)-9-(diethylamino)-5H-benzo[a]phenoxazin-5-one (manufactured by Fuji Molecular Planning Co., Ltd., 120 mg) was added thereto. Lastly, 4-(4,6-dimethoxy-1,3,5-triazin-2-yl)-4-methylmorpholinium chloride (DMT-MM, 114 mg) was added thereto, and the mixture was stirred for 21 hours at 25° C. The reaction liquid was added dropwise for 1.5 hours into a mixed liquid of diisopropyl ether (720 mL) and ethanol (180 mL), and the mixture was stirred at room temperature. Subsequently, the supernatant was removed, a mixed solution of diisopropyl ether (400 mL) and ethanol (100 mL) was added to the residue, and the mixture was stirred. A precipitate was collected by filtration, and thereby a product was obtained. The product thus obtained was dissolved in acetonitrile/water (50/50 (v/v), 160 mL), subsequently an ion exchange resin (Dowex 50) was added thereto, and the mixture was stirred for 1.0 hour at 0° C. The ion exchange resin was separated by filtration, and then acetonitrile was distilled off under reduced pressure. The residue was freeze-dried, and thereby a product was obtained (4,100 mg).

The product thus obtained and 7-ethyl-10-hydroxycamptothecin (EHC) (1,272 mg) were dissolved in DMF (18 mL), and then diisopropylcarbodiimide (DIPCI, 1,826 µL) was added thereto. The mixture was stirred for 21 hours at 25° C. Diisopropylcarbodiimide (DIPCI, 913 µL) was further added thereto, and the mixture was stirred for 6.5 hours. The reaction liquid was added dropwise for 1.0 hour into a mixed liquid of diisopropyl ether (1,600 mL) and ethyl acetate (400 mL), and the mixture was stirred overnight at room temperature. Subsequently, the supernatant was removed, a mixed solution of diisopropyl ether (800 mL) and ethyl acetate (200 mL) was added to the residue, and the mixture was stirred. A precipitate was collected by filtration, and thereby a product was obtained. The product thus obtained was dissolved in acetonitrile/water (75/25 (v/v), 120 mL), subsequently an ion exchange resin (Dowex 50) was added thereto, and the mixture was stirred for 2.0 hours at 0° C. The ion exchange resin was separated by filtration, and then acetonitrile was distilled off under reduced pressure. The residue was freeze-dried, and thereby the titled 7-ethyl-10- hydroxycamptothecin (EHC)-bonded block copolymer (Synthesis Example 5, 5,150 mg) was obtained.

The product of Synthesis Example 5 was subjected to a hydrolysis treatment using a 1 N aqueous solution of sodium hydroxide, and the amount of 7-ethyl-10-hydroxycamptothecin (EHC) thus released was quantitatively determined by high performance liquid chromatography (HPLC). Thus, the content of 7-ethyl-10-hydroxycamptothecin (EHC) was determined. As a result, the content of 7-ethyl-10-hydroxycamptothecin (EHC) in Synthesis Example 5 was 23.5% by mass.

The amount of bonding of 2-(2-aminoethoxy)-9-(diethylamino)-5H-benzo[a]phenoxazin-5-one in Synthesis Example 5 was 1 molecule, as determined from the consumption rate of 2-(2-aminoethoxy)-9-(diethylamino)-5H-benzo[a]phenoxazin-5-one in the reaction solution measured by high performance liquid chromatography (HPLC). Therefore, the total molecular weight of 2-(2-aminoethoxy)-9-(diethylamino)-5H-benzo[a]phenoxazin-5-one in Synthesis Example 5 was calculated to be 371≈0.4 kDa.

From these values, the total molecular weight of Synthesis Example 5 was calculated to be 20,826≈21 kDa.

The molecular weight of the main chain polymer combining the polyethylene glycol chain and the polyamino acid chain in Synthesis Example 5 was 14,882≈15 kDa from the sum of the molecular weight of the polyethylene glycol chain (12,000), the molecular weight of the glutamic acid 22.0 polymerizations (129.11×22.0=2,840), and the molecular weight of the acetyl group at the polyamino acid terminal (42).

Furthermore, the content of 2-(2-aminoethoxy)-9-(diethylamino)-5H-benzo[a]phenoxazin-5-one in Synthesis Example 5 was 1.8% by mass, the content of 7-ethyl-10-hydroxycamptothecin (EHC) was 23.5% by mass, and the content of the polyethylene glycol segment was 58% by mass.

[Synthesis Example 6] (Block Copolymer (C))

Synthesis of 7-ethyl-10-hydroxycamptothecin (EHC)-bonded and 2-(2-aminoethoxy)-9-(diethylamino)-5H-benzo[a]phenoxazin-5-one-bonded product of polyethylene glycol (2 kilodaltons)-polyglutamic acid (7.6 polymerizations) block copolymer A polyethylene glycol (2 kilodaltons)-polyglutamic acid (7.6 polymerizations) block copolymer (981 mg) synthesized by a method similar to the methods of Synthesis Example 1 and Synthesis Example 2, 2-(2-aminoethoxy)-9-(diethylamino)-5H-benzo[a]phenoxazin-5-one (manufactured by Tokyo Chemical Industry Co., Ltd., 42.2 mg), and 4-dimethylaminopyridine (DMAP, 45 mg) were dissolved in DMF (50 mL), and diisopropylcarbodiimide (DIPCI, 35 µL) was added thereto. The mixture was stirred for 4 hours at 25° C. Subsequently, 7-ethyl-10-hydroxycamptothecin (EHC) (532 mg), diisopropylcarbodiimide (DIPCI, 771 µL), and DMF (26 mL) were added thereto, and the mixture was further stirred for 20 hours. Subsequently, diisopropylcarbodiimide (DIPCI, 771 µL) was further added thereto, and the mixture was stirred for 4 hours. The reaction liquid was added dropwise for one hour into a mixed liquid of diisopropyl ether (675 mL) and ethyl acetate (75 mL). A precipitate thus obtained was collected by filtration and dried under reduced pressure. Thereby, a product was obtained. The product thus obtained was dissolved in acetonitrile/water (98/2 (v/v), 30 mL), subsequently an ion exchange resin (Dowex 50) was added thereto, and the mixture was stirred for 7 hours at 5° C. The ion exchange resin was separated by filtration, and then acetonitrile was distilled off under reduced pressure. The residue was freeze-dried, and thereby, the titled 7-ethyl-10-hydroxycamptothecin (EHC)-bonded block copolymer (Synthesis Example 6, 1,440 mg) was obtained.

The product of Synthesis Example 6 was subjected to a hydrolysis treatment using a 1 N aqueous solution of sodium hydroxide, and the amount of 7-ethyl-10-hydroxycamptothecin (EHC) thus released was quantitatively determined by high performance liquid chromatography (HPLC). Thus, the content of 7-ethyl-10-hydroxycamptothecin (EHC) was determined. As a result, the content of 7-ethyl-10-hydroxycamptothecin (EHC) in Synthesis Example 6 was 24.2% by mass.

The amount of bonding of 2-(2-aminoethoxy)-9-(diethylamino)-5H-benzo[a]phenoxazin-5-one in Synthesis Example 6 was 0.32 molecules, as determined from the consumption rate of 2-(2-aminoethoxy)-9-(diethylamino)-5H-benzo[a]phenoxazin-5-one in the reaction solution measured by high performance liquid chromatography (HPLC). Therefore, the total molecular weight of 2-(2-aminoethoxy)-9-(diethylamino)-5H-benzo[a]phenoxazin-5-one in Synthesis Example 6 was calculated to be 123≈0.1 kDa.

From these values, the total molecular weight of Synthesis Example 6 was calculated to be 4,779≈5 kDa.

The molecular weight of the main chain polymer combining a polyethylene glycol chain and a polyamino acid chain in Synthesis Example 6 was 3,023≈3 kDa, from the sum of the molecular weight of the polyethylene glycol chain (2,000), the molecular weight of the glutamic acid 7.6 polymerizations (129.11×7.6=981), and the molecular weight of the acetyl group at the polyamino acid terminal (42).

Furthermore, the content of 2-(2-aminoethoxy)-9-(diethylamino)-5H-benzo[a]phenoxazin-5-one in Synthesis Example 6 was 2.6% by mass, the content of 7-ethyl-10-hydroxycamptothecin (EHC) was 24.2% by mass, and the content of the polyethylene glycol segment was 42% by mass.

Synthesis Example 7

Synthesis of polyethylene glycol-polyglutamic acid block copolymer (polyethylene glycol molecular weight: 2 kilodaltons, number of polymerizations of polyglutamic acid: 7.8) having a tert-butoxycarbonyl group at one terminal A polyethylene glycol having one terminal tert-butoxycarbonyl group and another terminal 3-aminopropyl group (SUNBRIGHT BO-020EA, manufactured by NOF Corp., average molecular weight: 2 kilodaltons, 7.00 g) was dissolved in DMSO (140 mL), subsequently γ-benzyl L-glutamic acid-N-carboxyanhydride (8.4 g) was added thereto, and the mixture was stirred for 20.5 hours at 30° C. The reaction liquid was added dropwise for 0.5 hours into a mixed liquid of diisopropyl ether (2,520 mL), ethanol (280 mL), and ethyl acetate (30 mL), and the mixture was stirred for 7 hours at room temperature. Subsequently, the supernatant was removed, a mixed solution of diisopropyl ether (900 mL) and ethanol (100 mL) was added to the residue, and the mixture was stirred for 0.5 hours. Subsequently, a precipitate was collected by filtration and dried under reduced pressure, and thus a polymerization product (12.3 g) was obtained.

The polymerization product (12.0 g) thus obtained was dissolved in DMF (145 mL), and acetic anhydride (2.6 mL) was added thereto. The mixture was stirred for 2 hours at 20° C. The reaction liquid was added dropwise for 0.5 hours into a mixed liquid of diisopropyl ether (1,305 mL) and ethyl acetate (145 mL), and the mixture was stirred for 1.5 hours at room temperature. Subsequently, operations of removing the supernatant, adding a mixed solution of diisopropyl ether (900 mL) and ethanol (100 mL) to the residue, and stirring the mixture were carried out two times (stirring times were 0.5 hours and 1 hour, respectively), and then a precipitate was collected by filtration and dried under reduced pressure. Thereby, an acetylated polymer (12.1 g) was obtained.

The acetylated polymer (12.0) thus obtained was dissolved in DMF (260 mL), and 10% palladium-carbon (1.20 g) was added thereto. Subsequently, the reaction atmosphere was purged with hydrogen, and hydrogenolysis was performed for 22 hours at 30° C. and 1 atmosphere. The 10% palladium-carbon catalyst was separated by filtration (90 mL of ethyl acetate was used for washing down), subsequently the filtrate was added dropwise for 1 hour into a mixed liquid of heptanes (1,750 mL) and ethyl acetate (3,500 mL), and the mixture was stirred for 1.5 nights at room temperature. Subsequently, the supernatant was removed, a mixed liquid of heptanes (800 mL) and ethyl acetate (1,600 mL) was added to the residue, and the mixture was stirred for 0.5 hours. Subsequently, a precipitate was collected by filtration and dried under reduced pressure (7.85 g). This precipitate (7.6 g) was dissolved in 5% saline (760 mL), and the pH of the solution was adjusted to about 11 with a 2.2 N aqueous solution of sodium hydroxide. Subsequently, the solution was purified using partition/adsorption resin column chromatography (HP-20) and then using ion exchange resin column chromatography (Dowex 50). The solution thus eluted was concentrated under reduced pressure and then freeze-dried. Thereby, a polyethylene glycol-polyglutamic acid block copolymer having a tert-butoxycarbonyl group at one terminal (Synthesis Example 7: 5.5 g) was obtained.

The number of polymerizations of glutamic acid of Synthesis Example 7 was calculated to be 7.8 by a titration method using 0.1 N potassium hydroxide.

Synthesis Example 8

Synthesis of 4-phenyl-1-butanol-bonded product of polyethylene glycol (2 kilodaltons)-polyglutamic acid (7.8 polymerizations) block copolymer having 4-maleimidobutyric acid-N-hydroxysuccinimide ester at one terminal The product of Synthesis Example 7 (500 mg), 4-dimethylaminopyridine (DMAP, 156 mg), and 4-phenyl-1-butanol (132 µL) were dissolved in DMF (6.9 mL), and diisopropylcarbodiimide (DIPCI, 393 µL) was added thereto. The mixture was stirred for 22.5 hours at 25° C. Diisopropylcarbodiimide (DIPCI, 197 mL) was further added thereto, and the mixture was stirred for 1.5 hours. The reaction liquid was transferred into a dialysis membrane having a MWCO of 1.0 kDa, and dialysis was performed using acetonitrile/water (50/50 (v/v) as the external liquid. Dialysis was performed using water as the external liquid, and then acetonitrile was added to the internal liquid so that the internal liquid would become acetonitrile/water (50/50 (v/v)). An ion exchange resin (Dowex 50) was added to the internal liquid, and the mixture was stirred for one hour at room temperature. The ion exchange resin was separated by filtration, and then acetonitrile was distilled off under reduced pressure. The residue was freeze-dried, and thereby 4-phenyl-1-butanol-bonded product was obtained (550 mg).

TFA (10 mL) was added to the 4-phenyl-1-butanol-bonded product (530 mg), and the mixture was stirred for one hour at 0° C. Subsequently, TFA was distilled off, and then the residue was dissolved in DMF (10 mL). The solution was transferred into a dialysis membrane having a MWCO of 1.0 kDa. Dialysis was performed using water as the external liquid, and the internal liquid was freeze-dried. Thereby, a deprotected body was obtained (430 mg).

The deprotected body (410 mg) and 4-maleimidobutyric acid-N-hydroxysuccinimide (GMBS, 88.7 mg) were dissolved in DMF (15 mL), and DIPEA (144 µL) was added thereto. The mixture was stirred for one hour at 25° C. Subsequently, DIPEA (144 µL) was added thereto, and the mixture was further stirred for 4 hours. Subsequently, the reaction liquid was transferred into a dialysis membrane having a MWCO of 1.0 kDa, and dialysis was performed using acetonitrile as the external liquid. Dialysis was performed using water as the external liquid, and then the internal liquid was freeze-dried. Thereby, the titled 4-phenyl-1-butanol-bonded product of a polyethylene glycol (2 kilodaltons)-polyglutamic acid (7.8 polymerizations) block copolymer having 4-maleimidobutyric acid-N-hydroxysuccinimide ester at one terminal (Synthesis Example 8: 340 mg) was obtained.

The product of Synthesis Example 8 was subjected to a hydrolysis treatment using a 1 N aqueous solution of sodium hydroxide, and the amount of 4-phenyl-1-butanol thus released was quantitatively determined by high performance liquid chromatography (HPLC). Thus, the content of 4-phenyl-1-butanol was determined. As a result, the content of 4-phenyl-1-butanol in Synthesis Example 8 was 16.0% by mass.

From these values, the total molecular weight of Synthesis Example 8 was calculated to be 4,194≈4 kDa. Thereby, the content of the polyethylene glycol segment in Synthesis Example 8 was 48% by mass.

[Synthesis Example 9] (Comparative Example of Block Copolymer (B))

Synthesis of 4-phenyl-1-butanol-bonded and 2-(2-aminoethoxy)-9-(diethylamino)-5H-benzo[a]phenoxazin-5-one-bonded product of polyethylene glycol (12 kilodaltons)-polyglutamic acid (22.0 polymerizations) block copolymer A polyethylene glycol (12 kilodaltons)-polyglutamic acid (22.0 polymerizations) block copolymer (676 mg) synthesized by a method similar to the methods of Synthesis Example 1 and Synthesis Example 2, 2-(2-aminoethoxy)-9-(diethylamino)-5H-benzo[a]phenoxazin-5-one (manufactured by Tokyo Chemical Industry Co., Ltd., 17.0 mg), and 4-dimethylaminopyridine (DMAP, 122 mg) were dissolved in DMF (8.0 mL). Diisopropylcarbodiimide (DIPCI, 14 µL) was added thereto, and the mixture was stirred for 1.5 hours at 25° C. Subsequently, 4-phenyl-1-butanol (102 mg) and diisopropylcarbodiimide (DIPCI, 308 µL) were added thereto, and the mixture was stirred for 25 hours. Subsequently, the reaction liquid was added dropwise into a mixed liquid of diisopropyl ether (120 mL), ethanol (15 mL), and ethyl acetate (15 mL), and the mixture was stirred at room temperature. Subsequently, a precipitate was collected by filtration and dried under reduced pressure, and thereby, a product was obtained (770 mg). The product thus obtained was dissolved in acetonitrile/water (50/50 (v/v), 20 mL), subsequently an ion exchange resin (Dowex 50) was added thereto, and the mixture was stirred for 2.0 hours at 0° C. The ion exchange resin was separated by filtration, and then acetonitrile was distilled off under reduced pressure. The residue was freeze-dried, and thereby, the titled 4-phenyl-1-butanol-bonded and 2-(2-aminoethoxy)-9-(diethylamino)-5H-benzo[a]phenoxazin-5-one-bonded product of a polyethylene glycol (12 kilodaltons)-polyglutamic acid (22.0 polymerizations) block copolymer (Synthesis Example 9: 720 mg) was obtained.

The amount of bonding of 4-phenyl-1-butanol in Synthesis Example 9 was 15 molecules, as determined from the consumption rate of 4-phenyl-1-butanol in the reaction solution measured by high performance liquid chromatography (HPLC). Therefore, the total molecular weight of 4-phenyl-1-butanol in Synthesis Example 9 was calculated to be 2,224≈2 kDa.

Furthermore, the amount of bonding of 2-(2-aminoethoxy)-9-(diethylamino)-5H-benzo[a]phenoxazin-5-one in Synthesis Example 9 was one molecule, as determined from the consumption rate of 2-(2-aminoethoxy)-9-(diethylamino)-5H-benzo[a]phenoxazin-5-one in the reaction solution measured by high performance liquid chromatography (HPLC). Therefore, the total molecular weight of 2-(2-aminoethoxy)-9-(diethylamino)-5H-benzo[a]phenoxazin-5-one in Synthesis Example 9 was calculated to be 376≈0.4 kDa.

From these values, the total molecular weight of Synthesis Example 9 was calculated to be 18,091≈18 kDa.

The molecular weight of the main chain polymer combining a polyethylene glycol chain and a polyamino acid chain in Synthesis Example 9 was 14,882≈15 kDa, from the sum of the molecular weight of the polyethylene glycol chain (12,000), the molecular weight of the glutamic acid 7.6 polymerizations (129.11×22.0=2,840), and the molecular weight of the acetyl group at the polyamino acid terminal (42).

Furthermore, the content of 2-(2-aminoethoxy)-9-(diethylamino)-5H-benzo[a]phenoxazin-5-one in Synthesis Example 9 was 2.1% by mass, the content of 4-phenyl-1-butanol was 12% by mass, and the content of the polyethylene glycol segment was 66% by mass.

Synthesis Example 10

Synthesis of polyethylene glycol-polyglutamic acid block copolymer (polyethylene glycol molecular weight: 10 kilodaltons, number of polymerizations of polyglutamic acid: 22.3) having tert-butoxycarbonyl group at one terminal A polyethylene glycol having one terminal tert-butoxycarbonyl group and another terminal 3-aminopropyl group (Lot. 1214,587, Rapp Polymere GmbH, average molecular weight: 10 kilodaltons, 9.80 g) was dissolved in DMSO (196 mL), and then γ-benzyl L-glutamic acid-N-carboxyanhydride (6.2 g) was added thereto. The mixture was stirred for 24 hours at 30° C. The reaction liquid was added dropwise for one hour into a mixed liquid of diisopropyl ether (3,600 mL) and ethanol (400 mL), and the mixture was stirred for 2 hours at room temperature. Subsequently, the supernatant was removed, a mixed solution of diisopropyl ether (1,800 mL) and ethanol (200 mL) was added to the residue, and the mixture was stirred for one hour. Subsequently, a precipitate was collected by filtration and dried under reduced pressure, and a polymerization product (15.33 g) was obtained.

The polymerization product (15.0 g) thus obtained was dissolved in DMF (248 mL), and acetic anhydride (3.0 mL) was added thereto. The mixture was stirred for 18 hours at 20° C. The reaction liquid was added dropwise for 1.5 hours into a mixed liquid of diisopropyl ether (2,000 mL) and ethyl acetate (525 mL), and the mixture was stirred for 2 hours at room temperature. Subsequently, the supernatant was removed, a mixed solution of diisopropyl ether (800 mL) and ethanol (200 mL) was added to the residue, and the mixture was stirred for 5 hours. Subsequently, a precipitate was collected by filtration and dried under reduced pressure, and thereby an acetylated polymer (13.34 g) was obtained.

The acetylated polymer (13.0 g) thus obtained was dissolved in DMF (280 mL), and 10% palladium-carbon (1.32 g) was added. Subsequently, the reaction atmosphere was purged with hydrogen, and hydrogenolysis was performed for 70 hours at 30° C. and 1 atmosphere. The 10% palladium-carbon catalyst was separated by filtration, subsequently the filtrate was added dropwise for one hour into a mixed liquid of heptanes (3,700 mL) and ethyl acetate (1,850 mL), and the mixture was stirred for two nights at room temperature. Subsequently, the supernatant was removed, a mixed liquid of heptanes (1,200 mL) and ethyl acetate (600 mL) was added to the residue, and the mixture was stirred for 0.5 hours. Subsequently, a precipitate was collected by filtration and dried under reduced pressure. This precipitate (8.7 g) was dissolved in 5% saline (870 mL), and the pH of the solution was adjusted to about 11 with a 2.2 N aqueous solution of sodium hydroxide. Subsequently, the solution was purified using partition/adsorption resin column chromatography and then using ion exchange resin column chromatography. The solution thus eluted was concentrated under reduced pressure and then freeze-dried, and thereby a polyethylene glycol-polyglutamic acid block copolymer having a tert-butoxycarbonyl group at one terminal (Synthesis Example 10: 7.26 g) was obtained.

The number of polymerizations of glutamic acid in Synthesis Example 10 was calculated to be 22.3 by a titration method using 0.1 N potassium hydroxide.

Synthesis Example 11

Synthesis of 4-phenyl-1-butanol-bonded product of polyethylene glycol (10 kilodaltons)-polyglutamic acid (22.3 polymerizations) block copolymer having 4-maleimidobutyric acid-N-hydroxysuccinimide ester at one terminal The product of Synthesis Example 10 (500 mg), 4-dimethylaminopyridine (DMAP, 105 mg), and 4-phenyl-1-butanol (88.3 μL) were dissolved in DMF (6.9 mL), and diisopropylcarbodiimide (DIPCI, 264 μL) was added thereto. The mixture was stirred for 22 hours at 25° C. Subsequently, diisopropylcarbodiimide (DIPCI, 132 μL) was further added thereto, and the mixture was stirred for 1.5 hours. The reaction liquid was added dropwise for 15 minutes into a mixed liquid of diisopropyl ether (100 mL), ethanol (12.5 mL), and ethyl acetate (12.5 mL), and the mixture was stirred for 0.5 hours at room temperature. Subsequently, a precipitate was collected by filtration and dried under reduced pressure, and thereby a product was obtained. The product thus obtained was dissolved in acetonitrile/water (50/50 (v/v), 20 mL), subsequently an ion exchange resin was added thereto, and the mixture was stirred for 1.0 hour at room temperature. The ion exchange resin was separated by filtration, and then acetonitrile was distilled off under reduced pressure. The residue was freeze-dried, and thereby a product was obtained (550 mg).

Subsequently, TFA (6 mL) was added to the product (530 mg) thus obtained, and the mixture was stirred for 2 hours at 0° C. Subsequently, TFA was distilled off, and then the residue was dissolved in DMF (8 mL). The solution was added dropwise for 15 minutes into a mixed liquid of diisopropyl ether (104 mL) and ethyl acetate (52 mL), and the mixture was stirred for 0.5 hours at room temperature. Subsequently, a precipitate was collected by filtration and dried under reduced pressure, and thereby a product was obtained (597 mg).

Furthermore, the product thus obtained (516 mg) and 4-maleimidobutyric acid-N-hydroxysuccinimide (GMBS, 28.4 mg) were dissolved in DMF (15 mL), and DIPEA (92.2 μL) was added thereto. The mixture was stirred for 2 hours at 25° C. The reaction liquid was added dropwise over 0.5 hours into a mixed liquid of diisopropyl ether (216 mL) and ethyl acetate (54 mL), and the mixture was stirred for 0.5 hours at room temperature. Subsequently, the supernatant was removed, a mixed solution of diisopropyl ether (200 mL) and ethyl acetate (50 mL) was added to the residue, and the mixture was stirred for 0.5 hours. Subsequently, a precipitate was collected by filtration, and thereby the titled 4-phenyl-1-butanol-bonded product of a polyethylene glycol (10 kilodaltons)-polyglutamic acid (22.3 polymerizations) block copolymer having 4-maleimidobutyric acid-N-hydroxysuccinimide ester at one terminal (Synthesis Example 11: 475 mg) was obtained.

The product of Synthesis Example 11 was subjected to a hydrolysis treatment using a 1 N aqueous solution of sodium hydroxide, and the amount of 4-phenyl-1-butanol thus released was quantitatively determined by high performance liquid chromatography (HPLC). Thus, the content of 4-phenyl-1-butanol was determined. As a result, the content of 4-phenyl-1-butanol in Synthesis Example 11 was 10.3% by mass.

From these values, the total molecular weight of Synthesis Example 11 was calculated to be 15,933≈16 kDa. Thereby, the content of the polyethylene glycol segment in Synthesis example 8 was 62.8% by mass.

[Synthesis Example 12] (Comparative Example of Block Copolymer (A))

Synthesis of 4-phenyl-1-butanol-bonded product of polyethylene glycol (10 kilodaltons)-polyglutamic acid (22.3 polymerizations) block copolymer having cyclo[Arg-Gly-Asp-D-Phe-Cys] (cRGDfC) bonded thereto and having 4-maleimidobutyric acid-N-hydroxysuccinimide ester bonded to one terminal Acetonitrile/phosphate buffer (25/75 (v/v), 72 mL) was added to the product of Synthesis Example 11 (426 mg), and then cyclo[Arg-Gly-Asp-D-Phe-Cys] (manufactured by Peptide Institute, Inc., cRGDfC: 25.0 mg) that had been dissolved in advance in acetonitrile/phosphate buffer (25/75 (v/v), 9 mL) was added to the mixture. The resulting mixture was stirred for one hour at room temperature (phosphate buffer: potassium chloride 200 mg/L, potassium dihydrogen phosphate 200 mg/L, sodium chloride 8,000 mg/L, sodium hydrogen phosphate 1,150 mg/L, and disodium ethylenediaminetetraacetate dihydrate 7,420 mg/L). Subsequently, cysteine hydrochloride (49 mg) was added thereto, and the mixture was stirred for another one hour. Subsequently, the reaction solution was purified using Vivaspin (MWCO: 3 kDa) (Sartorius AG). Subsequently, the solution was transferred into a dialysis membrane having a MWCO of 6 to 8 kDa, and dialysis was performed using water as the external liquid. After completion of the dialysis, the internal liquid was freeze-dried, and thereby, the titled 4-phenyl-1-butanol-bonded product of a polyethylene glycol (10 kilodaltons)-polyglutamic acid (22.3 polymerizations) block copolymer having cyclo[Arg-Gly-Asp-D-Phe-Cys] (cRGDfC) as a target binding site bonded thereto and having 4-maleimidobutyric acid-N-hydroxysuccinimide ester at one terminal was obtained.

The reaction ratio of Synthesis Example 11 with respect to cRGDfC was 75.6%. From this value, it was calculated that the cRGDfC-bonded polymer having a molecular weight of 16,544≈17 kDa and the non-cRGDfC-bonded polymer having a molecular weight of 16,087≈16 kDa existed at a molar ratio of 75.6:24.4 and a weight ratio of 76.1:23.9.

The product of Synthesis Example 12 was subjected to a hydrolysis treatment using a 1 N aqueous solution of sodium hydroxide, and the amount of 4-phenyl-1-butanol thus released was quantitatively determined by high performance liquid chromatography (HPLC). Thus, the content of 4-phenyl-1-butanol was determined. As a result, the content of 4-phenyl-1-butanol in Synthesis Example 12 was 10.2% by mass.

The molecular weight of the main chain polymer combining a polyethylene glycol chain and a polyamino acid chain in Synthesis Example 12 was 14,921≈15 kDa from the sum of the molecular weight of the polyethylene glycol chain (10,000), the molecular weight of the glutamic acid 22.3 polymerizations (129.11×22.3=2,879), and the molecular weight of the acetyl group at the polyamino acid terminal (42).

Synthesis Example 13

Synthesis of L-valine benzyl ester-bonded product of polyethylene glycol (2 kilodaltons)-polyglutamic acid (7.8 polymerizations) block copolymer having 4-maleimidobutyric acid-N-hydroxysuccinimide ester at one terminal The product of Synthesis Example 7 (392 mg), 4-dimethylaminopyridine (DMAP, 123 mg), and L-valine benzyl ester hydrochloride (171 mg) were dissolved in DMF (10 mL), and diisopropylcarbodiimide (DIPCI, 308 μL) was added thereto. The mixture was stirred for 22.5 hours at 25° C. Furthermore, diisopropylcarbodiimide (DIPCI, 150 μL) was added thereto, and the mixture was stirred for 5 hours. The reaction liquid was transferred into a dialysis membrane having a MWCO of 1.0 kDa, and dialysis was performed using acetonitrile as the external liquid. Dialysis was performed using water as the external liquid, and then acetonitrile was added to the internal liquid so that the internal liquid would become acetonitrile/water (50/50 (v/v)). An ion exchange resin (Dowex 50) was added to the internal liquid, and the mixture was stirred for 30 minutes at room temperature. The ion exchange resin was separated by filtration, and then acetonitrile was distilled off under reduced pressure. The residue was freeze-dried, and thereby an L-valine benzyl ester-bonded product was obtained (444 mg).

TFA (2 mL) was added to the L-valine benzyl ester-bonded product (428 mg), and the mixture was stirred for 5 minutes at 0° C. and then was stirred for 7.5 hours at room temperature. Subsequently, TFA was distilled off, and then the residue was dissolved in $H_2O$ (7 mL). The solution was transferred into a dialysis membrane having a MWCO of 1.0 kDa. Dialysis was performed using water as the external liquid, and the internal liquid was freeze-dried. Thereby, a deprotected substance was obtained (387 mg).

The deprotected substance (190 mg) and 4-maleimidobutyric acid-N-hydroxysuccinimide (GMBS, 44.8 mg) were dissolved in DMF (7.5 mL), and DIPEA (68 μL) was added thereto. The mixture was stirred for one hour at 25° C. Subsequently, DIPEA (22 μL) was added thereto, and the mixture was further stirred for 20 minutes. Subsequently, the reaction liquid was transferred into a dialysis membrane having a MWCO of 1.0 kDa, and dialysis was performed using acetonitrile/water (50/50 (v/v)) as the external liquid. Dialysis was performed using water as the external liquid, and then the internal liquid was freeze-dried. Thereby, the titled L-valine benzyl ester-bonded product of a polyethylene glycol (2 kilodaltons)-polyglutamic acid (7.8 polymerizations) block copolymer having 4-maleimidobutyric acid-N-hydroxysuccinimide ester at one terminal (Synthesis Example 13: 153 mg) was obtained.

The reaction for introducing L-valine benzyl ester into Synthesis Example 13 was quantitatively determined by high performance liquid chromatography (HPLC), and it is found that the reaction proceeded 100%. From this, the content of L-valine benzyl ester in Synthesis Example 13 was calculated to be 28.3% by mass.

From these values, the total molecular weight of Synthesis Example 13 was calculated to be 4,569≈4.5 kDa. Thereby, the content of the polyethylene glycol segment in Synthesis Example 13 was 44% by mass.

[Synthesis Example 14] (Block Copolymer (C))

Synthesis of 7-ethyl-10-hydroxycamptothecin (EHC)-bonded and 2-(2-aminoethoxy)-9-(diethylamino)-5H-benzo[a]phenoxazin-5-one (Nile Red)-bonded product of polyethylene glycol (2 kilodaltons)-polyglutamic acid (9.1 polymerizations) block copolymer A polyethylene glycol (2 kilodaltons)-polyglutamic acid (9.1 polymerizations) block copolymer (1,000 mg) synthesized by a method similar to the methods of Synthesis Examples 1 and 2, 2-(2-aminoethoxy)-9-(diethylamino)-5H-benzo[a]phenoxazin-5-one (manufactured by Tokyo Chemical Industry Co., Ltd., 50.0 mg), 7-ethyl-10-hydroxycamptothecin (EHC) (500 mg), and 4-dimethylaminopyridine (DMAP, 51.3 mg) were dissolved in DMF (80 mL), and diisopropylcarbodiimide (DIPCI, 50 µL) was added thereto. The mixture was stirred for 21 hours at 25° C. The reaction liquid was added dropwise into a mixed liquid of diisopropyl ether (1,080 mL) and ethyl acetate (120 mL), and the supernatant was removed. Subsequently, a mixed liquid of diisopropyl ether (540 mL) and ethyl acetate (60 mL) was added to the residue. A precipitate thus obtained was collected by filtration and dried under reduced pressure, and thereby a product was obtained.

The product thus obtained was dissolved in acetonitrile/water (99/1 (v/v), 43 mL), and then an ion exchange resin (Dowex 50) was added to the solution. The mixture was stirred for 2 hours at 0° C. The ion exchange resin was separated by filtration, and then acetonitrile was distilled off under reduced pressure. The residue was freeze-dried, and thereby, the titled 7-ethyl-10-hydroxycamptothecin (EHC)-bonded and 2-(2-aminoethoxy)-9-(diethylamino)-5H-benzo[a]phenoxazin-5-one (Nile Red)-bonded block copolymer (Synthesis Example 14: 1,367 mg) was obtained.

The product of Synthesis Example 14 was subjected to a hydrolysis treatment using a 1 N aqueous solution of sodium hydroxide, and the amount of 7-ethyl-10-hydroxycamptothecin (EHC) thus released was quantitatively determined by high performance liquid chromatography (HPLC). Thus, the content of 7-ethyl-10-hydroxycamptothecin (EHC) was determined. As a result, the content of 7-ethyl-10-hydroxycamptothecin (EHC) in Synthesis Example 14 was 28.9% by mass.

The amount of bonding of 2-(2-aminoethoxy)-9-(diethylamino)-5H-benzo[a]phenoxazin-5-one in Synthesis Example 14 was 0.40 molecules, as determined from the consumption rate of 2-(2-aminoethoxy)-9-(diethylamino)-5H-benzo[a]phenoxazin-5-one in the reaction solution measured by high performance liquid chromatography (HPLC). Therefore, the total molecular weight of 2-(2-aminoethoxy)-9-(diethylamino)-5H-benzo[a]phenoxazin-5-one in Synthesis Example 14 was calculated to be 151≈0.15 kDa.

From these value, the total molecular weight of Synthesis Example 14 was calculated to be 4,625≈4.6 kDa.

The molecular weight of the main chain polymer combining a polyethylene glycol chain and a polyamino acid chain in Synthesis Example 14 was 3,217≈3.2 kDa from the sum of the molecular weight of the polyethylene glycol chain (2,000), the molecular weight of the glutamic acid 9.1 polymerizations (129.11×9.1=1,175), and the molecular weight of the acetyl group at one terminal of the polyamino acid (42).

Furthermore, the content of 2-(2-aminoethoxy)-9-(diethylamino)-5H-benzo[a]phenoxazin-5-one in Synthesis Example 14 was 3.3% by mass, the content of 7-ethyl-10-hydroxycamptothecin (EHC) was 28.9% by mass, and the content of polyethylene glycol segment was 43% by mass.

Synthesis Example 15

Synthesis of Cetuximab having sulfhydryl group Cetuximab (Bristol-Myers Squibb Co., 4 mg) was subjected to external liquid exchange with a HEPES buffer solution (pH 7.4) (6.37 mg/mL). A SAT(PEG) (N-succinimidyl-S-acetylthioacetylene glycol)/DMSO solution (12 mM, 17.5 µL) was added thereto, and the mixture was stirred for 30 minutes at room temperature. Unreacted low-molecular weight components were removed using a desalination column (PD-10), and then a hydroxylamine/5 mM-EDTA-containing HEPES buffer solution (pH 7.4, 0.5 M, 42 µL) was added thereto. The mixture was stirred for 50 minutes at room temperature. Again, low-molecular weight components were removed by PD-10, and thereby, Cetuximab having a sulfhydryl group (Synthesis Example 15, 2.2 mL) was obtained.

Synthesis Example 15 was 1.00 mg/mL based on Cetuximab according to a SEC analysis.

[Example 1-1] (Block Copolymer (A))

Synthesis of 4-phenyl-1-butanol-bonded product of polyethylene glycol (2 kilodaltons)-polyglutamic acid (7.8 polymerizations) block copolymer having cyclo[Arg-Gly-Asp-D-Phe-Cys] (cRGDfC) bonded thereto and having 4-maleimidobutyric acid-N-hydroxysuccinimide ester bonded to one terminal Phosphate buffer/acetonitrile (75/25 (v/v), 87 mL) was added to the product of Synthesis Example 8 (121 mg), and then cyclo[Arg-Gly-Asp-D-Phe-Cys] (manufactured by Peptide Institute, Inc., cRGDfC: 22.0 mg) that had been dissolved in advance in phosphate buffer/acetonitrile (75/25 (v/v), 12 mL) was added to the mixture. The mixture was stirred for one hour at room temperature (phosphate buffer: potassium chloride 200 mg/L, potassium dihydrogen phosphate 200 mg/L, sodium chloride 8,000 mg/L, sodium hydrogen phosphate 1,150 mg/L, and disodium ethylenediaminetetraacetate-dihydrate 7,420 mg/L). Subsequently, cysteine hydrochloride (56 mg) was added thereto, and the mixture was stirred for one hour.

Subsequently, the reaction solution was transferred into a dialysis membrane having a MWCO of 3.5 kDa, and dialysis was performed using water as the external liquid. After completion of the dialysis, the internal liquid was freeze-dried, and thereby the titled 4-phenyl-1-butanol-bonded product of a polyethylene glycol (2 kilodaltons)-polyglutamic acid (7.8 polymerizations) block copolymer having cyclo[Arg-Gly-Asp-D-Phe-Cys] (cRGDfC) bonded thereto and having 4-maleimidobutyric acid-N-hydroxysuccinimide ester bonded to one terminal was obtained.

The reaction ratio of Synthesis Example 8 with respect to cRGDfC was 77.2%. From this value, it was calculated that the cRGDfC-bonded polymer having a molecular weight of 4,790×5 kDa and the non-cRGDfC-bonded polymer having a molecular weight of 4,333≈4 kDa exist at a molar ratio of 77.2:22.8 and a weight ratio of 78.9:21.1. The present collected substance included 51.5% by mass of EDTA derived from the reaction solvent.

The content of 4-phenyl-1-butanol in Example 1-1 excluding the target binding site was 16.0% by mass from Synthesis Example 8.

The molecular weight of the main chain polymer combining a polyethylene glycol chain and a polyamino acid chain according to Example 1-1 was 3,049≈3 kDa from the sum of the molecular weight of the polyethylene glycol chain (2,000), the molecular weight of the glutamic acid 7.8 polymerizations (129.11×7.8=1,007), and the molecular weight of the acetyl group at the polyamino acid terminal (42).

The particle size of Example 1-1 was measured using a particle size-zeta potential analyzer, Zetasizer Nano ZS (manufactured by Malvern Panalytical, Ltd.), and the average particle size was 25 nm (1 mg/mL).

[Example 1-2A] (Block Copolymer (A))

Synthesis of 4-phenyl-1-butanol-bonded product of ester polyethylene glycol (2 kilodaltons)-polyglutamic acid (7.8 polymerizations) block copolymer having cyclo[Arg-Gly-Asp-D-Phe-Lys(Cys)] (cRGDfK(C)) bonded thereto and having 4-maleimidobutyric acid-N-hydroxysuccinimide at one terminal Phosphate buffer/acetonitrile (75/25 (v/v), 87 mL) was added to the product of Synthesis Example 8 (140 mg), and then cyclo[Arg-Gly-Asp-D-Phe-Lys(Cys)] (manufactured by Peptide Institute, Inc., cRGDfK(C): 33.1 mg) that had been dissolved in advance in phosphate buffer/acetonitrile (75/25 (v/v), 11 mL) was added to the mixture. The resulting mixture was stirred for 1.5 hours at room temperature (phosphate buffer:potassium chloride 200 mg/L, potassium dihydrogen phosphate 200 mg/L, sodium chloride 8,000 mg/L, sodium hydrogen phosphate 1,150 mg/L, and disodium ethylenediaminetetraacetate•dihydrate 7,420 mg/L). Subsequently, cysteine hydrochloride (59.7 mg) was added thereto, and the mixture was further stirred for 2 hours. Subsequently, the reaction solution was transferred into a dialysis membrane having a MWCO of 1.0 kDa. Dialysis was performed using water as the external liquid, and then the internal liquid was freeze-dried. Thereby, the titled 4-phenyl-1-butanol-bonded product of a polyethylene glycol (2 kilodaltons)-polyglutamic acid (7.8 polymerizations) block copolymer having cyclo[Arg-Gly-Asp-D-Phe-Lys(Cys)](cRGDfK(C)) bonded thereto and having 4-maleimidobutyric acid-N-hydroxysuccinimide ester at one terminal (Example 1-2A) was obtained.

The reaction ratio of Synthesis Example 8 with respect to cRGDfK(C) was 94.4%. From this value, it was calculated that the cRGDfK(C)-bonded polymer having a molecular weight of 4,918≈5 kDa and the non-cRGDfK(C)-bonded polymer having a molecular weight of 4,333≈4 kDa existed at a molar ratio of 94.4:5.6 and a weight ratio of 95.0:5.0. Meanwhile, the present collected substance included 48.2% by mass of EDTA derived from the reaction solvent.

The content of 4-phenyl-1-butanol in Example 1-2A excluding the target binding site was 16.0% by mass from Synthesis Example 8.

The molecular weight of the main chain polymer combining a polyethylene glycol chain and a polyamino acid chain according to Example 1-2A was 3,049≈3 kDa from the sum of the molecular weight of the polyethylene glycol chain (2,000), the molecular weight of the glutamic acid 7.8 polymerizations (129.11×7.8=1,007), and the molecular weight of the acetyl group at the polyamino acid terminal (42).

[Example 1-2B] (Block Copolymer (A))

Synthesis of 4-phenyl-1-butanol-bonded product of ester polyethylene glycol (2 kilodaltons)-polyglutamic acid (7.8 polymerizations) block copolymer having cyclo[Arg-Gly-Asp-D-Phe-Lys(Cys)] (cRGDfK(C)) bonded thereto and having 4-maleimidobutyric acid-N-hydroxysuccinimide at one terminal (desalination)

The product of Example 1-2A (115 mg) was dissolved in DMF/water (50/50 (v/v), 20 mL), and the solution was transferred into a dialysis membrane having a MWCO of 1.0 kDa. Dialysis was performed using water as the external liquid, and then the internal liquid was freeze-dried. Thereby, the titled 4-phenyl-1-butanol-bonded product of a polyethylene glycol (2 kilodaltons)-polyglutamic acid (7.8 polymerizations) block copolymer having cyclo[Arg-Gly-Asp-D-Phe-Lys(Cys)] (cRGDfK(C)) bonded thereto and 4-maleimidobutyric acid-N-hydroxysuccinimide ester at one terminal (Example 1-2B) was obtained. The content of EDTA derived from the reaction solvent was 5.0% by mass.

The particle size of Example 1-2B was measured using a particle size-zeta potential analyzer, Zetasizer Nano ZS (manufactured by Malvern Panalytical, Ltd.), and the average particle size was 22 nm (1 mg/mL).

[Example 1-3] (Block Copolymer (A))

Synthesis of 4-phenyl-1-butanol-bonded product of ester polyethylene glycol (2 kilodaltons)-polyglutamic acid (7.8 polymerizations) block copolymer having cyclo[Arg-Gly-Asp-D-Phe-Lys(Cys)] (cRGDfK(C)) bonded thereto and having 4-maleimidobutyric acid-N-hydroxysuccinimide at one terminal The product of Synthesis Example 8 (64 mg) was dissolved in phosphate buffer/acetonitrile (50/50 (v/v), 12 mL), and then cyclo[Arg-Gly-Asp-D-Phe-Lys(Cys)](manufactured by Peptide Institute, Inc., cRGDfK(C): 16.3 mg) that had been dissolved in advance in phosphate buffer/acetonitrile (50/50 (v/v), 4.3 mL) was added to the solution. The mixture was stirred for 3 hours at 25° C. room temperature (phosphate buffer:potassium chloride 200 mg/L, potassium dihydrogen phosphate 200 mg/L, sodium chloride 8,000 mg/mL, sodium hydrogen phosphate 1,150 mg/L, and disodium ethylenediaminetetraacetate•dihydrate 3,720 mg/L). Subsequently, cysteine hydrochloride (28 mg) was added thereto, and the mixture was further stirred for one hour. Subsequently, the reaction solution was transferred into a dialysis membrane having a MWCO of 3.5 kDa. Dialysis was performed using DMF/water (50/50 (v/v)) as the external liquid and then using water as the external liquid, and then the internal liquid was freeze-dried. Thereby, the titled 4-phenyl-1-butanol-bonded product of a polyethylene glycol (2 kilodaltons)-polyglutamic acid (7.8 polymerizations) block copolymer having cyclo[Arg-Gly-Asp-D-Phe-Lys(Cys)] (cRGDfK(C)) bonded thereto and having 4-maleimidobutyric acid-N-hydroxysuccinimide ester at one terminal (Example 1-3) was obtained.

The reaction ratio of Synthesis Example 8 with respect to cRGDfK(C) was 89.4%. From this value, it was calculated that the cRGDfK(C)-bonded polymer having a molecular weight of 4,917≈5 kDa and the non-cRGDfK(C)-bonded polymer having a molecular weight of 4,332×4 kDa existed at a molar ratio of 89.4:10.6 and a weight ratio of 90.5:9.5.

Meanwhile, the present collected substance included 4.5% by mass of EDTA derived from the reaction solvent.

The content of 4-phenyl-1-butanol in Example 1-3 excluding the target binding site was 16.0% by mass from Synthesis Example 8.

The molecular weight of the main chain polymer combining a polyethylene glycol chain and a polyamino acid chain in Example 1-3 was 3,049≈3 kDa from the sum of the molecular weight of the polyethylene glycol chain (2,000), the molecular weight of the glutamic acid 7.8 polymerizations (129.11×7.8=1,007), and the molecular weight of the acetyl group at the polyamino acid terminal (42).

[Example 2] (Block Copolymer (A))

Synthesis of 4-phenyl-1-butanol-bonded product of polyethylene glycol (2 kilodaltons)-polyglutamic acid (7.8 polymerizations) block copolymer having H[Cys-X-Tyr-His-Trp-Tyr-Gly-Tyr-Thr-Pro-Gln-Asn-Val-Ile]OH (X: 6-aminohexanoic acid (CX-GE11) bonded thereto and having 4-maleimidobutyric acid-N-hydroxysuccinimide ester at one terminal The product of Synthesis Example 8 (64 mg) was dissolved in phosphate buffer/acetonitrile (50/50 (v/v), 6.1 mL), and then cycloH[Cys-X-Tyr-His-Trp-Tyr-Gly-Tyr-Thr-Pro-Gln-Asn-Val-Ile]OH (X: 6-aminohexanoic acid) (manufactured by Sigma-Aldrich Corporation, CX-GE11: 13.6 mg) that had been dissolved in advance in phosphate buffer/acetonitrile (50/50 (v/v), 2.4 mL) was added to the solution. The mixture was stirred for 2.5 hours at 25° C. room temperature (phosphate buffer:potassium chloride 200 mg/L, potassium dihydrogen phosphate 200 mg/L, sodium chloride 8,000 mg/L, sodium hydrogen phosphate 1,150 mg/L, and disodium ethylenediaminetetraacetate•dihydrate 3,720 mg/L). Subsequently, cysteine hydrochloride (15 mg) was added thereto, and the mixture was further stirred for 2 hours. Subsequently, the reaction solution was transferred into a dialysis membrane having a MWCO of 3.5 kDa. Dialysis was performed using DMF/water (50/50 (v/v)) as the external liquid and then using water as the external liquid, and then the internal liquid was freeze-dried. Thereby, the titled 4-phenyl-1-butanol-bonded product of a polyethylene glycol (2 kilodaltons)-polyglutamic acid (7.8 polymerizations) block copolymer having H[Cys-X-Tyr-His-Trp-Tyr-Gly-Tyr-Thr-Pro-Gln-Asn-Val-Ile]OH (X: 6-aminohexanoic acid) (CX-GE11) bonded thereto and having 4-maleimidobutyric acid-N-hydroxysuccinimide ester at one terminal (Example 2) was obtained.

The reaction ratio of Synthesis Example 8 with respect to CX-GE11 was 72.2%. From this value, it was calculated that the CX-GE11-bonded polymer having a molecular weight of 5,967≈6 kDa and the non-CX-GR11-bonded polymer having a molecular weight of 4,333≈4 kDa existed at a molar ratio of 72.2:27.8 and a weight ratio of 78.2:21.8. Meanwhile, the present collected substance included 8.4% by mass of EDTA derived from the reaction solvent.

The content of 4-phenyl-1-butanol in Example 2 excluding the target binding site was 16.0% by mass from Synthesis Example 8.

The molecular weight of the main chain polymer combining a polyethylene glycol chain and a polyamino acid chain according to Example 2 was 3,049×3 kDa from the sum of the molecular weight of the polyethylene glycol chain (2,000), the molecular weight of the glutamic acid 7.8 polymerizations (129.11×7.8=1,007), and the molecular weight of the acetyl group at the polyamino acid terminal (42).

[Example 3] (Composition Including Block Copolymer (A) and Block Copolymer (B))

Composition including 4-phenyl-1-butanol-bonded product of polyethylene glycol (2 kilodaltons)-polyglutamic acid (7.8 polymerizations) block copolymer having cyclo[Arg-Gly-Asp-D-Phe-Lys(Cys)] (cRGDfK(C)) bonded thereto and having 4-maleimidobutyric acid-N-hydroxysuccinimide ester at one terminal, 4-phenyl-1-butanol-bonded product of polyethylene glycol (2 kilodaltons)-polyglutamic acid (7.8 polymerizations) block copolymer having cysteine bonded thereto and having 4-maleimidobutyric acid-N-hydroxysuccinimide ester at one terminal, and 4-phenyl-1-butanol-bonded and 2-(2-aminoethoxy)-9-(diethylamino)-5H-benzo[a]phenoxazin-5-one-bonded product of polyethylene glycol (2 kilodaltons)-polyglutamic acid (7.9 polymerizations) block copolymer (weight ratio 34:2:80) (molar ratio 29:2:80)

The products of Example 1-2A (34.8 mg, containing EDTA: 48.2% by mass) and Synthesis Example 4 (40.1 mg) were dissolved in DMF/water (50/14 (v/v)) so as to obtain a 2-(2-aminoethoxy)-9-(diethylamino)-5H-benzo[a]phenoxazin-5-one concentration of 0.33 mg/mL. Subsequently, the solution was transferred into a dialysis membrane having a MWCO of 1,000, and dialysis was performed using water as the external liquid. Finally, water was added so as to obtain a 2-(2-aminoethoxy)-9-(diethylamino)-5H-benzo[a]phenoxazin-5-one concentration of 0.11 mg/mL, and the mixture was filtered through a 0.45-μm filter. Thus, the titled Example 3 was produced.

The particle size of Example 3 was measured using a single nanoparticle size analyzer, IG-1000 (manufactured by Shimadzu Corp.), and the average particle size was 30 nm (2 mg/mL).

[Example 4] (Composition Including Block Copolymer (A) and Block Copolymer (B))

Composition including 4-phenyl-1-butanol-bonded product of polyethylene glycol (2 kilodaltons)-polyglutamic acid (7.8 polymerizations) block copolymer having cyclo[Arg-Gly-Asp-D-Phe-Lys(Cys)] (cRGDfK(C)) bonded thereto and having 4-maleimidobutyric acid-N-hydroxysuccinimide ester at one terminal, 4-phenyl-1-butanol-bonded product of polyethylene glycol (2 kilodaltons)-polyglutamic acid (7.8 polymerizations) block copolymer having cysteine bonded thereto and having 4-maleimidobutyric acid-N-hydroxysuccinimide ester at one terminal, and 4-phenyl-1-butanol-bonded and 2-(2-aminoethoxy)-9-(diethylamino)-5H-benzo[a]phenoxazin-5-one-bonded product of polyethylene glycol (2 kilodaltons)-polyglutamic acid (7.9 polymerizations) block copolymer (weight ratio 34:2:80) (molar ratio 29:2:80)

The titled Example 4 was produced by adding water to the products of Example 1-2B (3.9 mg, containing EDTA: 4.5% by mass) and Synthesis Example 4 (8.2 mg) so as to obtain a 2-(2-aminoethoxy)-9-(diethylamino)-5H-benzo[a]phenoxazin-5-one concentration of 0.068 mg/mL, dissolving the compounds by sonication under ice cooling, and filtering the solution through a 0.45-μm filter.

The particle size of Example 4 was measured using a single nanoparticle size analyzer, IG-1000 (manufactured by Shimadzu Corp.), and the average particle size was 15 nm (2 mg/mL).

[Example 5] (Composition Including Block Copolymer (A) and Block Copolymer (B))

Composition including 4-phenyl-1-butanol-bonded product of polyethylene glycol (2 kilodaltons)-polyglutamic acid (7.8 polymerizations) block copolymer having H[Cys-X-Tyr-His-Trp-Tyr-Gly-Tyr-Thr-Pro-Gln-Asn-Val-Ile]OH (X: 6-aminohexanoic acid) (CX-GE11) bonded thereto and having 4-maleimidobutyric acid-N-hydroxysuccinimide ester at one terminal, 4-phenyl-1-butanol-bonded product having polyethylene glycol (2 kilodaltons)-polyglutamic acid (7.8 polymerizations) block copolymer having cysteine bonded thereto and having 4-maleimidobutyric acid-N-hydroxysuccinimide ester at one terminal, and 4-phenyl-1-butanol-bonded and 2-(2-aminoethoxy)-9-(diethylamino)-5H-benzo[a]phenoxazin-5-one-bonded product of polyethylene glycol (2 kilodaltons)-polyglutamic acid (7.9 polymerizations) block copolymer (weight ratio 17:5:80) (molar ratio 12:5:80)

The titled Example 5 was produced by adding water to the products of Example 2 (3.6 mg, containing EDTA: 8.4% by mass) and Synthesis Example 4 (12.2 mg) so as to obtain a 2-(2-aminoethoxy)-9-(diethylamino)-5H-benzo[a]phenoxazin-5-one concentration of 0.15 mg/mL, dissolving the compounds by sonication under ice cooling, and filtering the solution through a 0.45-μm filter.

The particle size of Example 5 was measured using a single nanoparticle size analyzer, IG-1000 (manufactured by Shimadzu Corp.), and the average particle size was 11 nm (2 mg/mL).

[Example 6] (Composition Including Block Copolymer (A) and Block Copolymer (C))

Composition including 4-phenyl-1-butanol-bonded product of polyethylene glycol (2 kilodaltons)-polyglutamic acid (7.8 polymerizations) block copolymer having H[Cys-X-Tyr-His-Trp-Tyr-Gly-Tyr-Thr-Pro-Gln-Asn-Val-Ile]OH (X: 6-aminohexanoic acid) (CX-GE11) bonded thereto and having 4-maleimidobutyric acid-N-hydroxysuccinimide ester at one terminal, 4-phenyl-1-butanol-bonded product of polyethylene glycol (2 kilodaltons)-polyglutamic acid (7.8 polymerizations) block copolymer having cysteine bonded thereto and having 4-maleimidobutyric acid-N-hydroxysuccinimide ester at one terminal, and 7-ethyl-10-hydroxycamptothecin (EHC)-bonded and 2-(2-aminoethoxy)-9-(diethylamino)-5H-benzo[a]phenoxazin-5-one-bonded product of polyethylene glycol (2 kilodaltons)-polyglutamic acid (7.59 polymerizations) block copolymer (weight ratio 17:5:80) (molar ratio 14:5:80)

The titled Example 6 was produced by adding water to the products of Example 2 (3.7 mg, containing EDTA: 8.4% by mass) and Synthesis Example 6 (12.3 mg) so as to obtain a 2-(2-aminoethoxy)-9-(diethylamino)-5H-benzo[a]phenoxazin-5-one concentration of 0.15 mg/mL, dissolving the compounds by sonication under ice cooling, and filtering the solution through a 0.45-μm filter.

The particle size of Example 6 was measured using a single nanoparticle size analyzer, IG-1000 (manufactured by Shimadzu Corp.), and the average particle size was 17 nm (2 mg/mL).

[Example 7] (Composition Including Block Copolymer (A) and Block Copolymer (C))

Composition including 4-phenyl-1-butanol-bonded product of polyethylene glycol (2 kilodaltons)-polyglutamic acid (7.8 polymerizations) block copolymer having cyclo[Arg-Gly-Asp-D-Phe-Lys (Cys)] (cRGDfK(C)) bonded thereto and having 4-maleimidobutyric acid-N-hydroxysuccinimide ester at one terminal, 4-phenyl-1-butanol-bonded product of polyethylene glycol (2 kilodaltons)-polyglutamic acid (7.8 polymerizations) block copolymer having cysteine bonded thereto and having 4-maleimidobutyric acid-N-hydroxysuccinimide ester at one terminal, and 7-ethyl-10-hydroxycamptothecin (EHC)-bonded and 2-(2-aminoethoxy)-9-(diethylamino)-5H-benzo[a]phenoxazin-5-one-bonded product of polyethylene glycol (2 kilodaltons)-polyglutamic acid (7.59 polymerizations) block copolymer (weight ratio 36:4:60) (molar ratio 35:4:60)

The titled Example 7 was produced by adding water to the products of Example 1-3 (37.6 mg, containing EDTA: 4.5% by mass) and Synthesis Example 6 (54.2 mg) so as to obtain a 2-(2-aminoethoxy)-9-(diethylamino)-5H-benzo[a]phenoxazin-5-one concentration of 0.25 mg/mL, dissolving the compounds by sonication under ice cooling, and filtering the solution through a 0.45-μm filter.

The particle size of Example 7 was measured using a single nanoparticle size analyzer, IG-1000 (manufactured by Shimadzu Corp.), and the average particle size was 26 nm (2 mg/mL).

[Example 8] (Composition Including Block Copolymer (A) and Block Copolymer (C))

Composition including 4-phenyl-1-butanol-bonded product of polyethylene glycol (2 kilodaltons)-polyglutamic acid (7.8 polymerizations) block copolymer having cyclo[Arg-Gly-Asp-D-Phe-Lys(Cys)] (cRGDfK(C)) bonded thereto and having 4-maleimidobutyric acid-N-hydroxysuccinimide ester at one terminal, 4-phenyl-1-butanol-bonded product of polyethylene glycol (2 kilodaltons)-polyglutamic acid (7.8 polymerizations) block copolymer having cysteine bonded thereto and having 4-maleimidobutyric acid-N-hydroxysuccinimide ester at one terminal, and 7-ethyl-10-hydroxycamptothecin (EHC)-bonded and 2-(2-aminoethoxy)-9-(diethylamino)-5H-benzo[a]phenoxazin-5-one-bonded product of polyethylene glycol (2 kilodaltons)-polyglutamic acid (7.59 polymerizations) block copolymer (weight ratio 17:2:80) (molar ratio 17:2:80)

The titled Example 8 was produced by adding water to the products of Example 1-3 (37.6 mg, containing EDTA: 4.5% by mass) and Synthesis Example 6 (31.1 mg) so as to obtain a 2-(2-aminoethoxy)-9-(diethylamino)-5H-benzo[a]phenoxazin-5-one concentration of 0.25 mg/mL, dissolving the compounds by sonication under ice cooling, and filtering the solution through a 0.45-μm filter.

The particle size of Example 8 was measured using a single nanoparticle size analyzer, IG-1000 (manufactured by Shimadzu Corp.), and the average particle size was 8 nm (2 mg/mL).

[Example 9] (Composition Including Block Copolymer (A) and Block Copolymer (C))

Composition including 4-phenyl-1-butanol-bonded product of polyethylene glycol (2 kilodaltons)-polyglutamic acid (7.8 polymerizations) block copolymer having H[Cys-X-Tyr-His-Trp-Tyr-Gly-Tyr-Thr-Pro-Gln-Asn-Val-Ile]OH (X: 6-aminohexanoic acid)(CX-GE11) bonded thereto and having 4-maleimidobutyric acid-N-hydroxysuccinimide ester at one terminal, 4-phenyl-1-butanol-bonded product of polyethylene glycol (2 kilodaltons)-polyglutamic acid (7.8 polymerizations) block copolymer having cysteine bonded thereto and having 4-maleimidobutyric acid-N-hydroxysuccinimide ester at one terminal, and 7-ethyl-10-hydroxycamptothecin (EHC)-bonded and 2-(2-aminoethoxy)-9-(diethylamino)-5H-benzo[a]phenoxazin-5-one-bonded product of polyethylene glycol (2 kilodaltons)-polyglutamic acid (7.59 polymerizations) block copolymer (weight ratio 30:8:60) (molar ratio 24:9:60)

The titled Example 9 was produced by adding water to the products of Example 2 (17.1 mg, containing EDTA: 8.4% by mass) and Synthesis Example 6 (25.1 mg) so as to obtain a 2-(2-aminoethoxy)-9-(diethylamino)-5H-benzo[a]phenoxazin-5-one concentration of 0.28 mg/mL, dissolving the compounds by sonication under ice cooling, and filtering the solution through a 0.45-µm filter.

The particle size of Example 9 was measured using a single nanoparticle size analyzer, IG-1000 (manufactured by Shimadzu Corp.), and the average particle size was 16 nm (2 mg/mL).

[Example 10] (Composition Including Block Copolymer (A) and Block Copolymer (C))

Composition including 4-phenyl-1-butanol-bonded product of polyethylene glycol (2 kilodaltons)-polyglutamic acid (7.8 polymerizations) block copolymer having H[Cys-X-Tyr-His-Trp-Tyr-Gly-Tyr-Thr-Pro-Gln-Asn-Val-Ile]OH (X: 6-aminohexanoic acid) (CX-GE11) bonded thereto and having 4-maleimidobutyric acid-N-hydroxysuccinimide ester at one terminal, 4-phenyl-1-butanol-bonded product of polyethylene glycol (2 kilodaltons)-polyglutamic acid (7.8 polymerizations) block copolymer having cysteine bonded thereto and having 4-maleimidobutyric acid-N-hydroxysuccinimide ester at one terminal, and 7-ethyl-10-hydroxycamptothecin (EHC)-bonded and 2-(2-aminoethoxy)-9-(diethylamino)-5H-benzo[a]phenoxazin-5-one-bonded product of polyethylene glycol (2 kilodaltons)-polyglutamic acid (7.59 polymerizations) block copolymer (weight ratio 15:4:80) (molar ratio 12:5:80)

The titled Example 10 was produced by adding water to the products of Example 2 (6.7 mg, containing EDTA: 8.4% by mass) and Synthesis Example 6 (25.5 mg) so as to obtain a 2-(2-aminoethoxy)-9-(diethylamino)-5H-benzo[a]phenoxazin-5-one concentration of 0.28 mg/mL, dissolving the compounds by sonication under ice cooling, and filtering the solution through a 0.45-µm filter.

The particle size of Example 10 was measured using a single nanoparticle size analyzer, IG-1000 (manufactured by Shimadzu Corp.), and the average particle size was 15 nm (2 mg/mL).

[Example 11] (Composition Including Block Copolymer (A) and Block Copolymer (C))

Composition including L-valine benzyl ester-bonded product of polyethylene glycol (2 kilodaltons)-polyglutamic acid (7.8 polymerizations) block copolymer having 4-maleimidobutyric acid-N-hydroxysuccinimide ester at one terminal and Cetuximab-bonded product having sulfhydryl group, and 7-ethyl-10-hydroxycamptothecin (EHC) and 2-(2-aminoethoxy)-9-(diethylamino)-5H-benzo[a]phenoxazin-5-one (Nile Red) of polyethylene glycol (2 kilodaltons)-polyglutamic acid (9.1 polymerizations) block copolymer (molar ratio 1:1.81, weight ratio 1:60.8) The products of Synthesis Example 13 (1.50 mg) and Synthesis Example 14 (8.64 mg) were dissolved in a HEPES buffer solution (pH 7.0, 50 mL). The solution was irradiated with ultrasonic waves for 8 minutes and then was purified using a gel filtration column (Hiprep™ 16/60, Sephacryl™ S-300 HR). Thereby, precursor nanoparticles of the titled Example 11 were produced (3.19 mg/mL).

Subsequently, the product of Synthesis Example 15 (0.80 mL, 0.80 mg) was added to the precursor nanoparticles (0.5 mL, 1.60 mg) described above, and the mixture was stirred by shaking for 6 hours at 30° C. An N-ethylmaleimide/HEPES buffer solution (pH 7.0, 0.5 mM, 0.05 mL) was added thereto, and the mixture was stirred by shaking for 30 minutes. Subsequently, an L-cysteine/5 mM-EDTA-containing HEPES buffer solution (pH 7.5, 5 mM, 0.1 mL) was added thereto, and thereby, unreacted sulfhydryl groups and maleimide groups were inactivated. Unreacted low-molecular weight components were removed using an ultrafiltration filter (Vivaspin, MWCO 3,000), and then a HEPES buffer solution (pH 7.5) was added to the residue to make up 1.5 mL. The mixture was filtered through a 0.45-µm filter, and thereby, the title composition of Example 11 was produced (1.60 mg/mL).

The block copolymer (A) having Cetuximab as a target binding site in the composition of Example 11 is such that since the mixing ratio of Synthesis Example 13 and Synthesis Example 15 is (from the molecular weight of Synthesis Example 13, 4,569≈4.5 kDa and the molecular weight of Synthesis Example 15, 151,000×151 kDa) molar ratio 1:0.23, the block copolymer (A) having Cetuximab as a target binding site corresponds to 23% of Synthesis Example 13. That is, the weight ratio of the block copolymer (A) having Cetuximab as a target binding site and the block copolymer (C) having drug SN-38 was A:C=1:1.81 (molar ratio A:C=1/155,569 (molecular weight of A):1.81/4626 (molecular weight of C)=1:60.8).

The composition of Example 11 was purged with ultrapure water by ultrafiltration, and the particle size was measured using IG-1000. The average particle size was 18 nm.

[Comparative Example 1] (Comparative Example of Block Copolymer (B))

Preparation including only 4-phenyl-1-butanol-bonded and 2-(2-aminoethoxy)-9-(diethylamino)-5H-benzo[a]phenoxazin-5-one-bonded product of polyethylene glycol (10 kilodaltons)-polyglutamic acid (21.0 polymerizations) block copolymer (Synthesis Example 3)

The product of Synthesis Example 3 was dissolved in DMF/water (50/10 (v/v)) so as to obtain a 2-(2-aminoethoxy)-9-(diethylamino)-5H-benzo[a]phenoxazin-5-one (Nile Red) concentration of 0.60 mg/mL. Subsequently, the solution was transferred into a dialysis membrane having a MWCO of 1.0 kDa, and dialysis was performed using water as the external liquid. Finally, water was added so as to obtain a 2-(2-aminoethoxy)-9-(diethylamino)-5H-benzo[a]phenoxazin-5-one concentration of 0.15 mg/mL, and the mixture was filtered through a 0.45-µm filter. Thus, the titled Comparative Example 1 was produced.

The particle size of Comparative Example 1 was measured using a single nanoparticle size analyzer, IG-1000 (manufactured by Shimadzu Corp.), and the average particle size was 18 nm (2 mg/mL).

[Comparative Example 2] (Comparative Example of Block Copolymer (C))

Preparation including only 7-ethyl-10-hydroxycamptothecin (EHC)-bonded and 2-(2-aminoethoxy)-9-(diethylamino)-5H-benzo[a]phenoxazin-5-one-bonded product of polyethylene glycol (12 kilodaltons)-polyglutamic acid (22.0 polymerizations) block copolymer (Synthesis Example 5) The particle size of Comparative Example 2 was measured using a single nanoparticle size analyzer, IG-1000 (manufactured by Shimadzu Corp.), and the average particle size was 23 nm (5 mg/mL).

[Comparative Example 3] (Block Copolymer (C))

Preparation including only 7-ethyl-10-hydroxycamptothecin (EHC)-bonded and 2-(2-aminoethoxy)-9-(diethylamino)-5H-benzo[a]phenoxazin-5-one-bonded product of polyethylene glycol (2 kilodaltons)-polyglutamic acid (7.59 polymerizations) block copolymer (Synthesis Example 6)

The particle size of Comparative Example 3 was measured using a single nanoparticle size analyzer, IG-1000 (manufactured by Shimadzu Corp.), and the average particle size was 13 nm (2 mg/mL).

[Comparative Example 4] (Block Copolymer (B))

Preparation of 4-phenyl-1-butanol-bonded and 2-(2-aminoethoxy)-9-(diethylamino)-5H-benzo[a]phenoxazin-5-one-bonded product of polyethylene glycol (12 kilodaltons)-polyglutamic acid (22.0 polymerizations) block copolymer Synthesis Example 11

The particle size of Comparative Example 4 was measured using a single nanoparticle size analyzer, IG-1000 (manufactured by Shimadzu Corp.), and the average particle size was 36 nm (2 mg/mL).

[Comparative Example 5] (Block Copolymer (B))

Preparation of 4-phenyl-1-butanol-bonded and 2-(2-aminoethoxy)-9-(diethylamino)-5H-benzo[a]phenoxazin-5-one-bonded product of polyethylene glycol (2 kilodaltons)-polyglutamic acid (7.9 polymerizations) block copolymer Synthesis Example 4

The particle size of Comparative Example 5 was measured using a single nanoparticle size analyzer, IG-1000 (manufactured by Shimadzu Corp.), and the average particle size was 13 nm (2 mg/mL).

[Comparative Example 6] (Composition Including Comparative Example of Block Copolymer (A) and Comparative Example of Block Copolymer (B))

Composition including 4-phenyl-1-butanol-bonded product of polyethylene glycol (10 kilodaltons)-polyglutamic acid (22.3 polymerizations) block copolymer having cyclo[Arg-Gly-Asp-D-Phe-Cys] (cRGDfC) bonded thereto and 4-maleimidobutyric acid-N-hydroxysuccinimide ester at one terminal, 4-phenyl-1-butanol-bonded product of polyethylene glycol (10 kilodaltons)-polyglutamic acid (22.3 polymerizations) block copolymer having cysteine bonded thereto and having 4-maleimidobutyric acid-N-hydroxysuccinimide ester at one terminal, and 4-phenyl-1-butanol-bonded and 2-(2-aminoethoxy)-9-(diethylamino)-5H-benzo[a]phenoxazin-5-one-bonded product of polyethylene glycol (10 kilodaltons)-polyglutamic acid (21.0 polymerizations) block copolymer (weight ratio 15:5:80) (molar ratio 14:5:80) The product of Synthesis Example 3 (83.1 mg) and Synthesis Example 12 (20.8 mg) were dissolved in DMF/water (50/10 (v/v)) so as to obtain a 2-(2-aminoethoxy)-9-(diethylamino)-5H-benzo[a]phenoxazin-5-one concentration of 0.55 mg/mL. Subsequently, the solution was transferred into a dialysis membrane having a MWCO of 1.0 kDa, and dialysis was performed using water as the external liquid. Finally, water was added so as to obtain a 2-(2-aminoethoxy)-9-(diethylamino)-5H-benzo[a]phenoxazin-5-one concentration of 0.18 mg/mL, and the mixture was lastly filtered through a 0.45-μm filter. Thereby, the product was obtained.

The particle size of Comparative Example 6 was measured using a single nanoparticle size analyzer, IG-1000 (manufactured by Shimadzu Corp.), and the average particle size was 28 nm (2 mg/mL).

[Comparative Example 7] (Composition Including Comparative Example of Block Copolymer (A) and Block Copolymer (C))

Composition including L-cysteine-bonded product and L-valine benzyl ester-bonded product of polyethylene glycol (2 kilodaltons)-polyglutamic acid (7.8 polymerizations) block copolymer having 4-maleimidobutyric acid-N-hydroxysuccinimide ester at one terminal, and 7-ethyl-10-hydroxycamptothecin (EHC) of polyethylene glycol (2 kilodaltons)-polyglutamic acid (9.1 polymerizations) block copolymer and 2-(2-aminoethoxy)-9-(diethylamino)-5H-benzo[a]phenoxazin-5-one (Nile Red) (molar ratio 1:5.69, weight ratio 1.54:8.64)

The products of Synthesis Example 13 (1.50 mg) and Synthesis Example 14 (8.64 mg) were dissolved in a HEPES buffer solution (pH 7.0, 50 mL). The solution was irradiated with ultrasonic waves for 8 minutes and then was purified using a gel filtration column (Hiprep™ 16/60, Sephacryl™ S-300 HR). Thereby, precursor nanoparticles of Example 11 described above were produced (3.19 mg/mL).

Subsequently, an L-cysteine/5 mM-EDTA-containing HEPES buffer solution (pH 7.5, 5 mM, 0.05 mL) (L-cysteine 30.3 mg) was added to the above-mentioned precursor nanoparticles (0.5 mL, 1.60 mg), and thereby maleimide groups were inactivated. Unreacted low-molecular weight components were removed using an ultrafiltration filter (Vivaspin, MWCO 3,000), and then a HEPES buffer solution (pH 7.5) was added to make up 1.5 mL. The mixture was filtered through a 0.45-μm filter, and thereby a composition of the titled Comparative Example 7 was produced (1.07 mg/mL).

In the composition of Comparative Example 7, the block copolymer having L-cysteine that does not exhibit a target binding ability (Comparative Example of block copolymer (A)) has, under the assumption that L-cysteine (molecular weight 121) has reacted 100% with Synthesis Example 13 (molecular weight 4,569), the molecular weight of 4,690. That is, the weight ratio of the block copolymer having L-cysteine (Comparative A) and the block copolymer (C) having drug SN-38 was Comparative A:C=1.5×4,690/4,569: 8.64=1.54:8.64 (molar ratio was Comparative A:C=1.54/4,690 (molecular weight of Comparative A):8.64/4,626 (molecular weight of C)=1:5.69).

The composition of Comparative Example 7 was purged with ultrapure water by ultrafiltration, and the particle size was measured using IG-1000. The average particle size was 19 nm.

[Test Example 1] Test for Drug Releasability into Phosphate Buffer Solution

Example 7, Example 8, and Comparative Example 3 were respectively dissolved in a phosphate buffer solution (pH 7.4) at a concentration of 1.0 mg/mL in terms of the composition weight, and the solutions were left to stand at a constant temperature of 37° C. The amount of 7-ethyl-10-hydroxycamptothecin (EHC) released was measured over time by HPLC, and the proportion of the amount of EHC released with respect to the total amount of EHC in the compound used was determined.

The results are shown in FIG. 1.

As a result, in Comparative Example 3, Example 7, and Example 8, EHC releases of 61%, 42%, and 46%, respectively, for 6 hours were recognized in the phosphate buffer solution in the absence of enzyme.

[Test Example 2] Test for Measuring Binding Force of Target Binding Site (cRGD)-Containing Composition by Integrin Binding Assay A test for measuring the binding force of Example 3, Example 4, and Comparative Example 6, all having cRGD as a target binding site, and Comparative Example 1 that did not have a target binding site (cRGD), for integrin αVβ3 was carried out by the following procedure.

100 μL each of 1 μg/mL Recombinant Mouse Integrin alpha V beta 3 Protein (R&D Systems, Inc.) produced with PBS(-) was added to a 96-well Costar high capacity binding plate, and the plate was left to stand overnight at 4° C. to thereby bind integrin αVβ3 to the bottom face of the wells. Subsequently, integrin αVβ3 in the wells was removed by suctioning, and 200 μL of a Blocking/Binding buffer (50 mM Tris HCl at pH 7.4, 100 mM NaCl, 2 mM $CaCl_2$, 1 mM $MgCl_2$, 1 mM $MnCl_2$, 1% BSA) was added to each well. Blocking was performed at an interval of one hour at room temperature. Furthermore, the Blocking/Binding buffer was removed by suctioning, and 100 μL each of test solutions of dilution series of Example 3 and Example 4, and Comparative Example 1 and Comparative Example 6 was added to each well, and the test solutions were left to stand for 2 hours at room temperature.

100 μL of biotinylated vitronectin (1 μg/mL) obtained by biotinylated human recombinant vitronectin (Wako Pure Chemical Industries, Ltd.) was added in advance into each well using Biotin Labeling Kit-$NH_2$ (Dojindo Molecular Technologies, Inc.), and the plate was left to stand at room temperature for 3 hours. Subsequently, the wells were washed three times using 200 μL of Blocking/Binding buffer, and 100 μL of streptavidin-HRP (GE Healthcare) diluted 10,000 times with the Blocking/Binding buffer was added to each well. The mixture was left to stand for one hour at room temperature. The wells were washed two times using 200 μL of the Blocking/Binding buffer. 100 μL of TMB One Component Substrate (Bethyl Laboratories, Inc.) was added to the wells, and the wells were left to stand for 30 minutes at room temperature to develop color. Subsequently, 1 Normal HCl was added to the wells, and the reaction was stopped.

Figure 2:
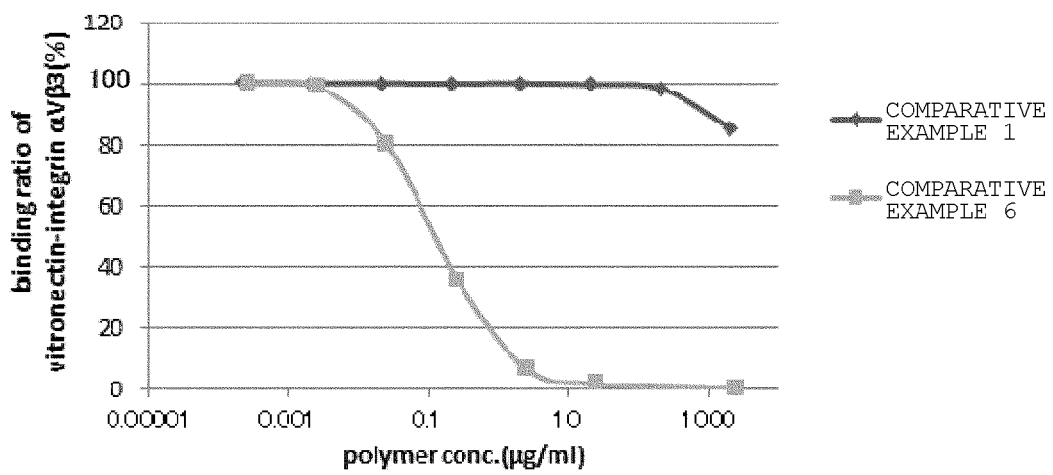
FIG. 2 shows results of a test for bindability to integrin αVβ3 of Comparative Examples 1 and 6.
Figure 3:
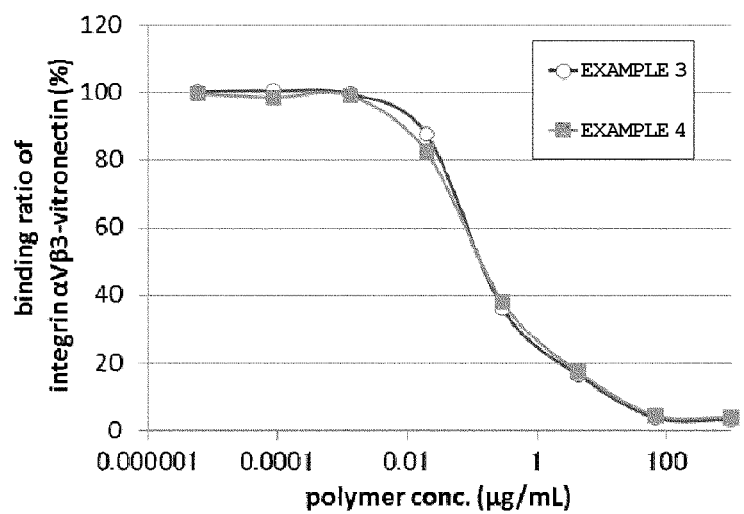
FIG. 3 shows results of a test for bindability to integrin αVβ3 of Examples 3 and 4.

Within 30 minutes after the addition, the absorbance at 450 nm was measured, and the binding ratio of biotinylated vitronectin to integrin αVβ3 was calculated. The results are shown in FIG. 2 and FIG. 3.

For a micelle-forming composition formed from a mixture of a block copolymer (A) having a cRGD ligand bonded thereto as a target binding site and a block copolymer (B) having a fluorescent substance added thereto, inhibition of binding to vitronectin and integrin αVβ3 was measured. The results for Comparative Example 1 and Comparative Example 6 are shown in FIG. 2, and the results of Example 3 and Example 4 are shown in FIG. 3. Inhibition of binding to Example 3, Example 4, and Comparative Example 6, which are micelle-forming compositions having a cRGD ligand added thereto as a target binding site, was recognized. In contrast, inhibition of binding of the micelle-forming composition of Comparative Example 1 that does not have a target binding site (cRGD) was not recognized. From the above, it was obvious that a composition having a cRGD ligand as a target binding site forms micelle-like associates having bindability to integrin αVβ3 as the cRGD ligand is exposed at the outer shell portion, and that the target binding site (cRGD) applied to the block copolymer (A) has a recognition function for the target site and also has a function of binding to the composition.

[Test Example 3] Test for Evaluating Intratumor and Intrarenal Tissue Distribution A suspension of cultured cancer cell human glioma U87MG was subcutaneously transplanted on the dorsal sides of nude mice using an injection needle-attached syringe. Example 3, Comparative Example 4, and Comparative Example 5 were dissolved in a 5% glucose injectable solution, and each of the solutions was intravenously administered a single time in an amount of 5 mg/kg in terms of 2-(2-aminoethoxy)-9-(diethylamino)-5H-benzo[a]phenoxazin-5-one.

After one hour and after 24 hours from the administration, the mice were exsanguinated under isoflurane anesthesia, and frozen embedded sections of extracted tumor and kidney were produced. Fluorescence derived from 2-(2-aminoethoxy)-9-(diethylamino)-5H-benzo[a]phenoxazin-5-one in the administered composition was observed.

Figure 4:
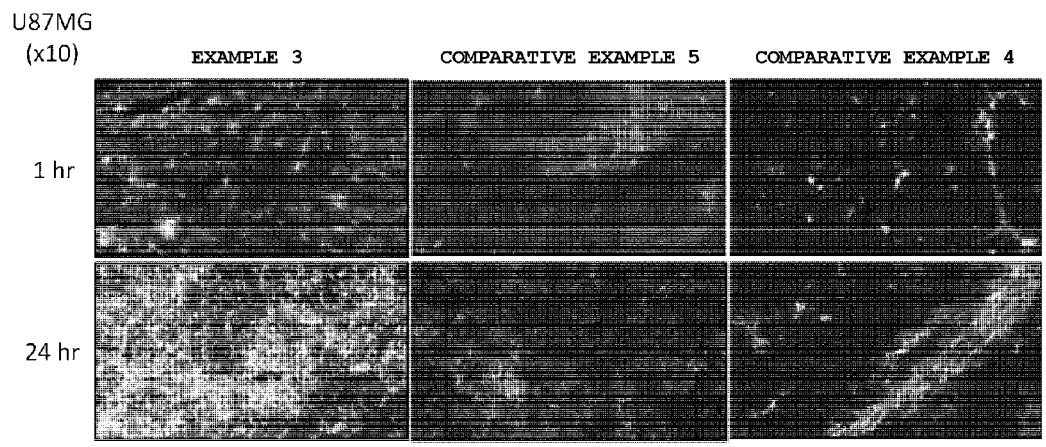
FIG. 4 shows a set of images showing distributions in a tumor tissue in Example 3 and Comparative Examples 4 and 5.
Figure 6:
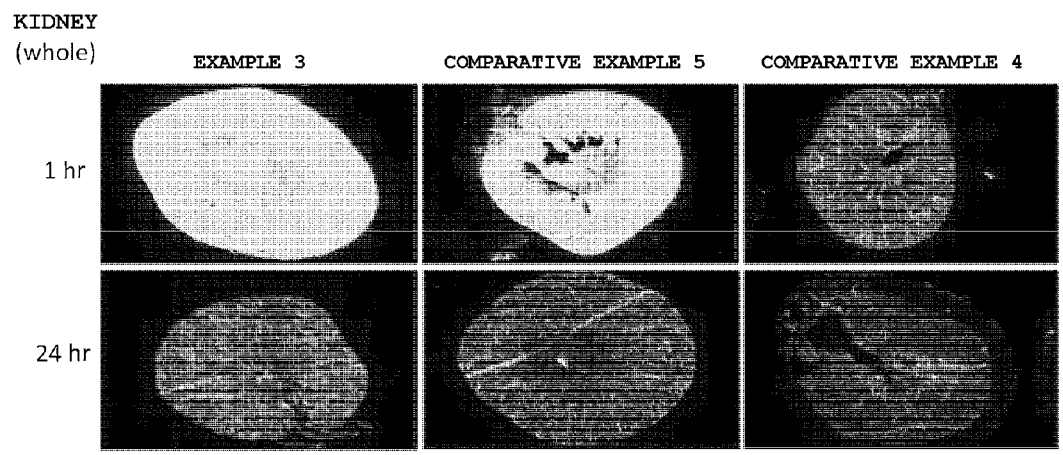
FIG. 6 shows a set of images showing the distributions in a kidney tissue of Example 3 and Comparative Example 4 and 5.

The results of the intratumor tissue distribution of each composition are shown in FIG. 4, and the results of intrarenal tissue distribution are shown in FIG. 6.

Figure 5:
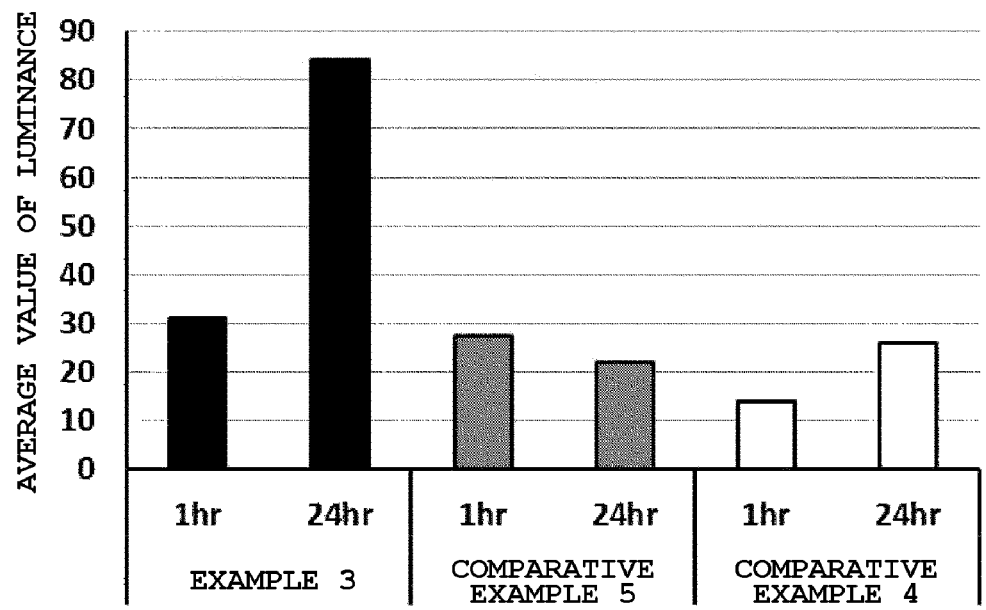
FIG. 5 is a graph for calculating luminances of images showing the distributions in a tumor tissue of FIG. 4.
Figure 7:
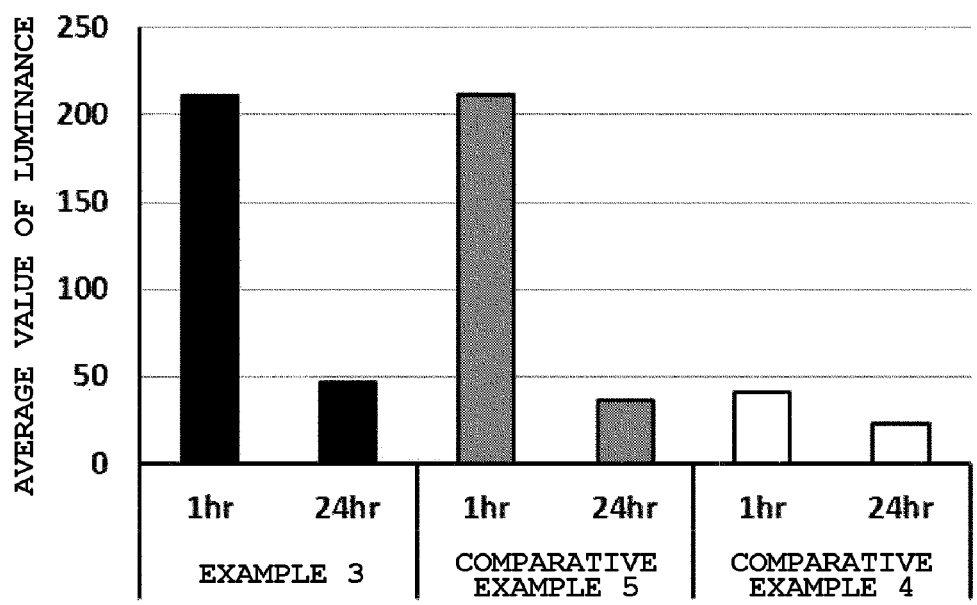
FIG. 7 is a graph for calculating the luminances of the images showing the distributions in the kidney tissue of FIG. 6.

Furthermore, luminance was calculated based on those images using an Image-Pro Premier (Media Cybernetics, Inc.). The values of luminance of tumor tissue sections are shown in FIG. 5, and the values of luminance of kidney tissue sections are shown in FIG. 7.

As a result of Test Example 3, in Example 3 and Comparative Example 5, one hour after the administration, penetration into the entire tumor and fluorescent signals were observed in a wider region. In comparison with these, in Comparative Example 4, it was found that penetration into the tumor was poor. Moreover, in observation of a distribution of fluorescent 24 hours after administration, in Example 3, the fluorescent signals were observed over a wide area inside the tumor, and excellent penetrability into the interior of a tumor tissue was obtained in comparison with Comparative Examples 4 and 5.

In the kidney, fluorescence was observed in the blood vessels and in the renal tubules with Example 3 and Comparative Example 5. Meanwhile, regarding Comparative Example 4, fluorescence was not recognized in areas other than the blood vessels in the kidney.

From the above-described results, it was found that Example 3 rapidly penetrates into the deeper part of a tumor compared to Comparative Example 4, and retains in the tumor for a long time period compared to Comparative Example 4 and Comparative Example 5. From these in-tumor distribution characteristics, it was found that Example 3 is useful as a DDS carrier capable of delivering a drug over a wide range of area inside a tumor tissue. Furthermore, in the kidney, it was found that Example 3 is rapidly subjected to renal excretion compared to Comparative Example 4. In this regard, it is considered that Example 3 has a feature of excretability out of the body while being a polymeric DDS carrier, and therefore, Example 3 is a carrier having a performance by which disorders in normal tissues, such as blood toxicity, may be reduced by avoiding excessive retention in vivo of a drug.

[Test Example 4] Test for Evaluating Tissue Distribution in Tumor and in Kidney

A suspension of cultured cancer cell human glioma U87MG was subcutaneously transplanted on the dorsal sides of nude mice using an injection needle-attached syringe. Example 7, Comparative Example 2, and Comparative Example 3 were dissolved in a 5% glucose injectable solution, and each of the solutions was intravenously administered a single time in an amount of 5 mg/kg in terms of 2-(2-aminoethoxy)-9-(diethylamino)-5H-benzo[a]phenoxazin-5-one.

After one hour and after 24 hours from the administration, the mice were exsanguinated under isoflurane anesthesia, and frozen embedded sections of extracted tumor and kidney were produced. Fluorescence derived from 2-(2-aminoethoxy)-9-(diethylamino)-5H-benzo[a]phenoxazin-5-one in the administered composition was observed.

Figure 8:
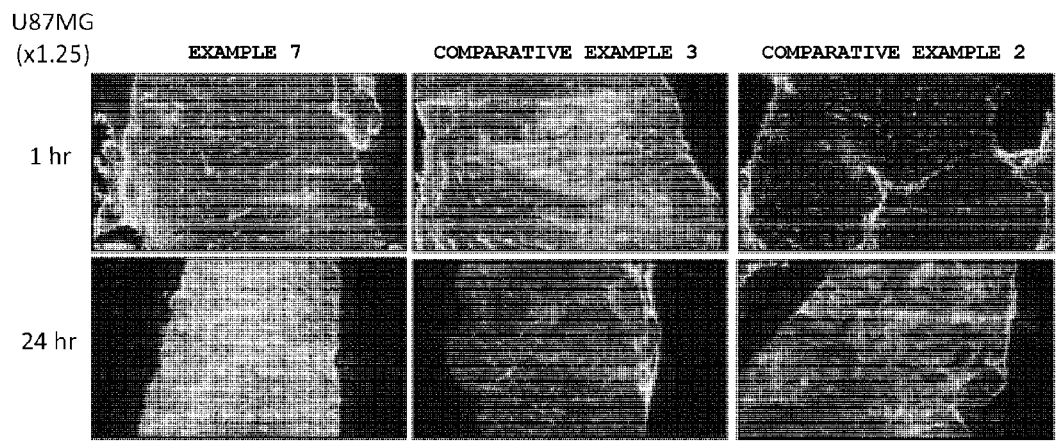
FIG. 8 shows a set of images showing the distributions in a tumor tissue of Example 7 and Comparative Examples 2 and 3.
Figure 10:
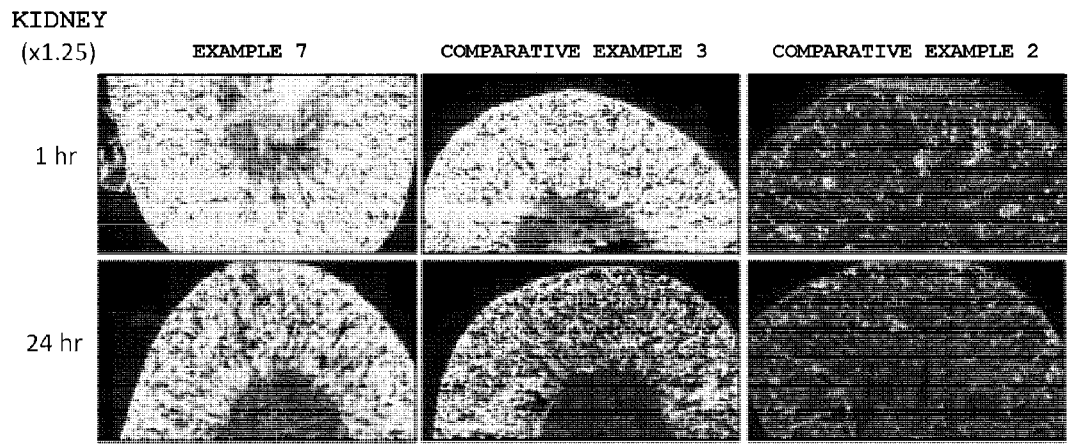
FIG. 10 shows a set of images showing the distributions in the kidney tissue of Example 7 and Comparative Examples 2 and 3.

The results of the tissue distribution in the tumor of the respective compositions are shown in FIG. 8, and the results of the tissue distributions in the kidney of the respective compositions are shown in FIG. 10.

Figure 9:
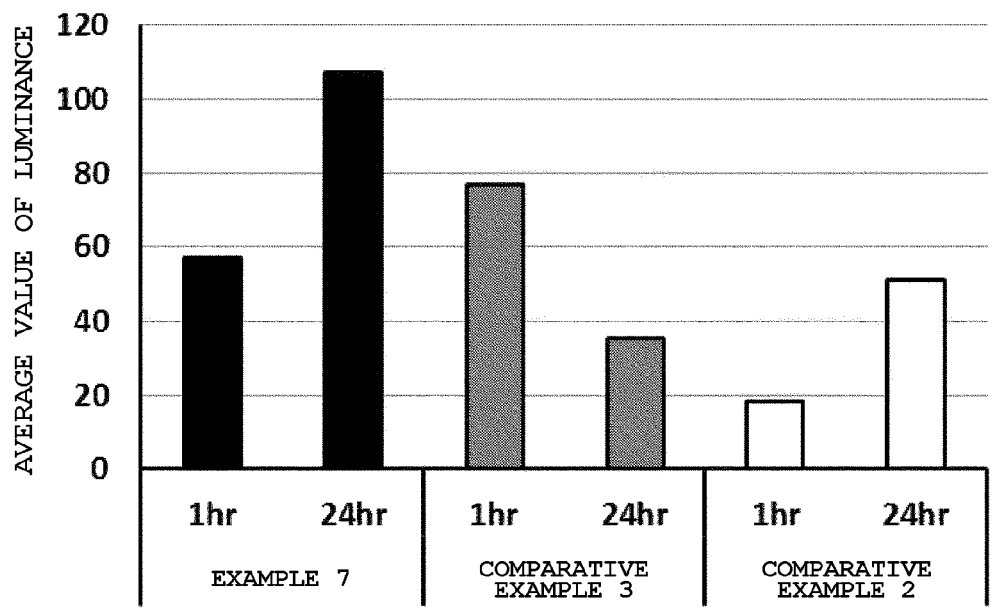
FIG. 9 is a graph for calculating the luminances of the images showing the distributions in the tumor tissue of FIG. 8.
Figure 11:
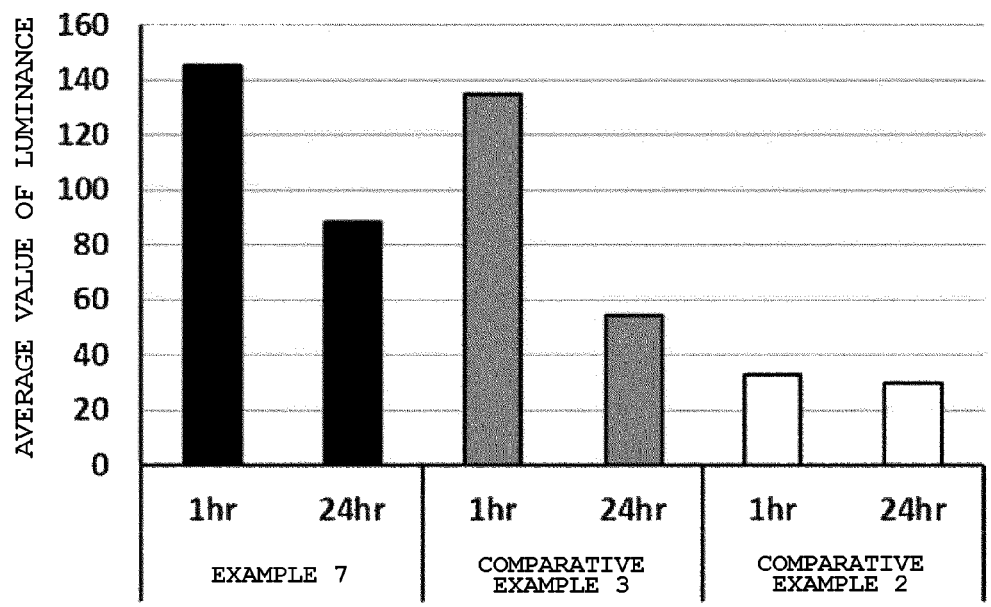
FIG. 11 is a graph for calculating the luminances of the images showing the distributions in the kidney tissue of FIG. 10.

Furthermore, based on those images, the luminance was calculated using Image-Pro Premier (Media Cybernetics, Inc.), and the values of luminance of tumor tissue sections are shown in FIG. 9, while the values of luminance of kidney tissue sections are shown in FIG. 11.

From the results of Test Example 4, Example 7 and Comparative Example 3 penetrated into the entire tumor compared to Comparative Example 2 after one hour from the administration, and fluorescent signals were observed in a wider area. Furthermore, after 24 hours from the administration, fluorescent signals were observed in a wider area than in the tumor for Example 7, compared to Comparative Example 2 and Comparative Example 3.

In the kidney, fluorescence was observed in the blood vessels and the renal tubules, regarding Example 7 and Comparative Example 3. Meanwhile, fluorescence was not recognized in areas other than in the blood vessels, regarding Comparative Example 2

From the above-described results, it was suggested that Example 7 penetrates rapidly into the deeper part of a tumor compared to Comparative Example 2, and Example 7 may increase the antitumor effects by retaining in the tumor for a long time period compared to Comparative Example 2 and Comparative Example 3. Furthermore, in the kidney, it was found that Example 7 was rapidly subjected to kidney excretion compared to Comparative Example 2, and Example 7 has excretability out of the body. Therefore, it is considered that Example 7 is a carrier having a performance by which disorders in normal tissue, such as blood toxicity, may be reduced by avoiding excessive retention in vivo of a drug.

[Test Example 5] Test for Evaluating Retention Characteristics in Tissue Based on AUC Ratio of Blood Plasma and Tumor A suspension of cultured cancer cell human glioma U87MG was subcutaneously transplanted on the dorsal sides of nude mice using an injection needle-attached syringe. Example 7, Comparative Example 2, and Comparative Example 3 were dissolved in a 5% glucose injectable solution, and Comparative Example 2 was intravenously administered a single time in an amount of 52 mg/kg in terms of 7-ethyl-10-hydroxycamptothecin, while Comparative Example 3 and Example 7 were respectively intravenously administered a single time in an amount of 46.8 mg/kg in terms of 7-ethyl-10-hydroxycamptothecin.

Figure 12:
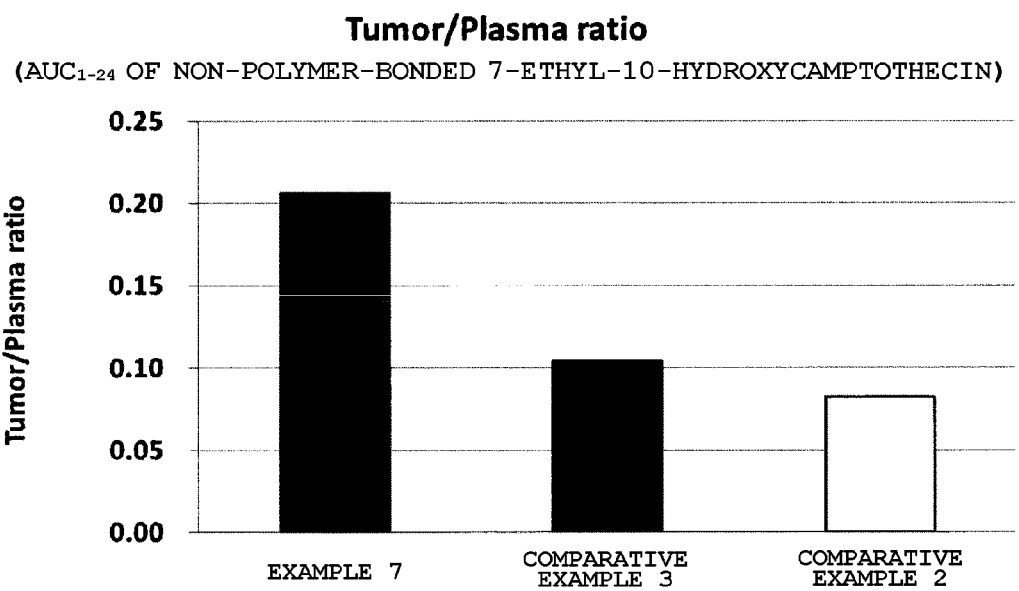
FIG. 12 shows an AUC in a tumor/AUC in blood plasma of Example 7 and Comparative Examples 2 and 3.

After one hour, 6 hours, and 24 hours from the administration, blood was collected from the mice under isoflurane anesthesia, the blood was centrifuged, and then the blood plasma was collected. The mice were euthanized after blood collection, and tumors were extracted and crushed. The amounts of non-polymer-bonded 7-ethyl-10-hydroxycamptothecin in the blood plasma and tumors were measured by HPLC, and the AUC values from 1 to 24 hours were calculated by a trapezoidal approximation method. Using these values, the ratio of $AUC_{1-24}$ (µg·hr/g) in tumor and $AUC_{1-24}$ (µg·hr/mL) in blood plasma was calculated. The results are shown in FIG. 12.

From the results of Test Example 5, Example 7 exhibited an AUC in tumor/AUC in blood plasma value that was about twice the values of Comparative Example 2 and Comparative Example 3. From this, it was considered that Example 7 is capable of delivering the included compound, 7-ethyl-10-hydroxycamptothecin, more selectively to tumors compared to Comparative Example 2 and Comparative Example 3, and efficacy enhancement and toxicity reduction may be expected.

[Test Example 6] Test for Measuring Target Binding Ability of Target Binding Site (Cetuximab)-Containing Composition by Flow Cytometry A test of measuring the target binding ability was carried out by the following procedure, for Example 11 containing a block copolymer (A) having Cetuximab as a target binding site, and for Comparative Example 7 containing a block copolymer that did not have a target binding site.

BxPC-3 cells were inoculated into a Coster 24-well plate (Corning, Inc.) at a rate of 1×10 cells per well, and the cells were cultured overnight using a 10% FBS-containing RPMI1640 (GIBCO) medium. On the next day, FITC-labeled Cetuximab (4.4 molecules of FITC bonded to one molecule of Cetuximab), Example 11, and Comparative Example 7 were respectively added to the medium to a final concentration of 10 µg/mL in terms of Cetuximab, and the cells were cultured for one hour. Meanwhile, Comparative Example 7 that did not have Cetuximab was added in an equimolar amount to Example 11 in terms of the block copolymer (C).

Figure 13:
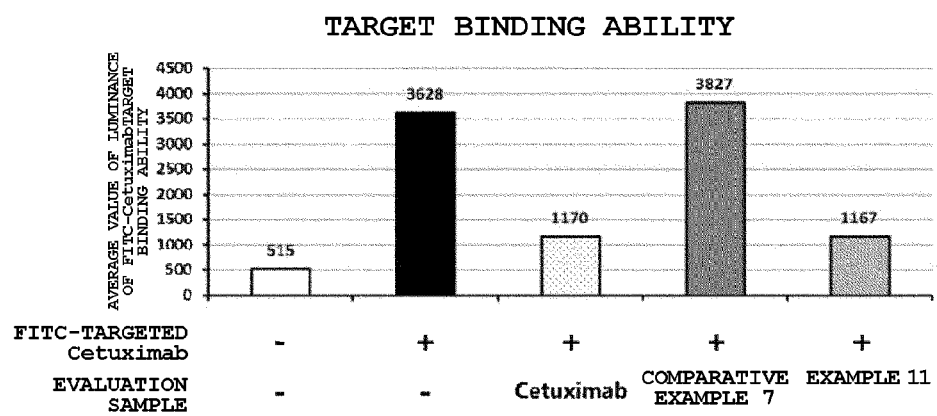
FIG. 13 shows results of a test for target binding ability of Example 11 and Comparative Example 7.

After the cells were cultured, the cells were collected from the plate and washed once with 1% FBS-containing PBS at 4° C. Subsequently, the cells were suspended in 1% FBS-containing PBS at 4° C., and the luminance of FITC was measured with a flow cytometer, SH800 (Sony Corporation). The results are shown in FIG. 13.

As a result of Test Example 6, Comparative Example 7 exhibited a luminance to the same extent as the cells that did not have Cetuximab added thereto, and target binding inhibition of FITC-labeled Cetuximab was not recognized. On the other hand, Example 11 exhibited a luminance to the same extent as the cells having Cetuximab added thereto, and target binding inhibition of FITC-labeled Cetuximab was recognized to the same extent as Cetuximab. From the above results, it was found that a composition having Cetuximab as a target binding site had Cetuximab exposed at the outer shell portion and thus formed micelle-like associates having a binding ability to a target.

The invention claimed is:

1. A composition comprising a block copolymer (A) and a block copolymer (C),
wherein the block copolymer (A) comprising a hydrophilic polymer segment linked to a hydrophobic polymer segment, the hydrophilic polymer segment containing a polyethylene glycol chain, and the hydrophobic polymer segment containing a polyamino acid chain having a hydrophobic substituent in a side chain;
wherein the block copolymer (A) is represented by General Formula (1):

[Chemical Formula 1]

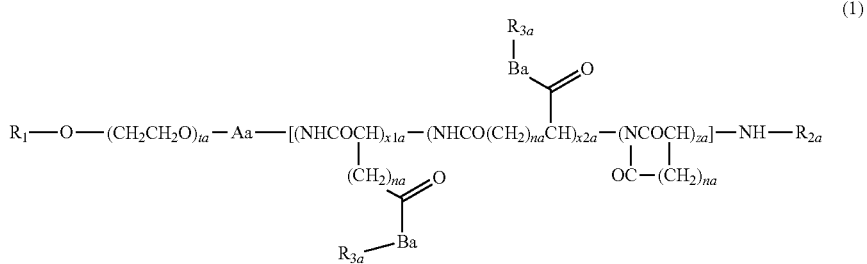

(1)

wherein
- $R_1$ represents a bonding residue of a target binding site;
- ta represents an integer from 20 to 140;
- Aa represents a substituted (C1-C6) alkylene group which may have a substituent;
- $R_{2a}$ represents a substituent selected from the group consisting of a hydrogen atom, a (C1-C6) acyl group, and a (C1-C6) alkoxycarbonyl group;
- $R_{3a}$ includes one or more bonding residues of one or more hydrophobic substituents selected from the group consisting of a linear, branched or cyclic (C1-C30) alkoxy group which may have a substituent, a linear, branched or cyclic (C1-C30) alkylamino group which may have a substituent, a linear, branched or cyclic (C1-C30) dialkylamino group which may have a substituent, a (C1-C8) alkylaminocarbonyl-(C1-C8) alkylamino group which may have a substituent, a bonding residue of a physiologically active substance having a hydroxy group and/or an amino group, and a bonding residue of a fluorescent substance having a hydroxy group and/or an amino group, while the remaining part is a hydroxy group;
- Ba represents a single bond or a divalent bonding group;
- na represents 1 or 2;
- x1a, x2a, and za each independently represent an integer from 0 to 20;
- x1a+x2a represents an integer from 1 to 20;
- (x1a+x2a+za) represents an integer from 3 to 20; and respective constituent units having Ria bonded thereto, and a constituent unit formed by intramolecular cyclization of a side-chain carbonyl group constitute a structure with those constituent units being each independently randomly arranged;

wherein the hydrophilic polymer segment has a target binding site bonded thereto, and the main chain polymer combining the polyethylene glycol chain and the polyamino acid chain has a molecular weight of not less than 2 kilodaltons and not more than 7 kilodaltons; and wherein the block copolymer (C) being a block copolymer having a hydrophilic polymer segment containing a polyethylene glycol chain linked to a hydrophobic polymer segment containing a polyamino acid chain having a physiologically active substance with a hydroxy group and/or an amino group bonded to a side-chain carboxy group;

wherein the block copolymer (C) is represented by General Formula (3):

[Chemical Formula 3]

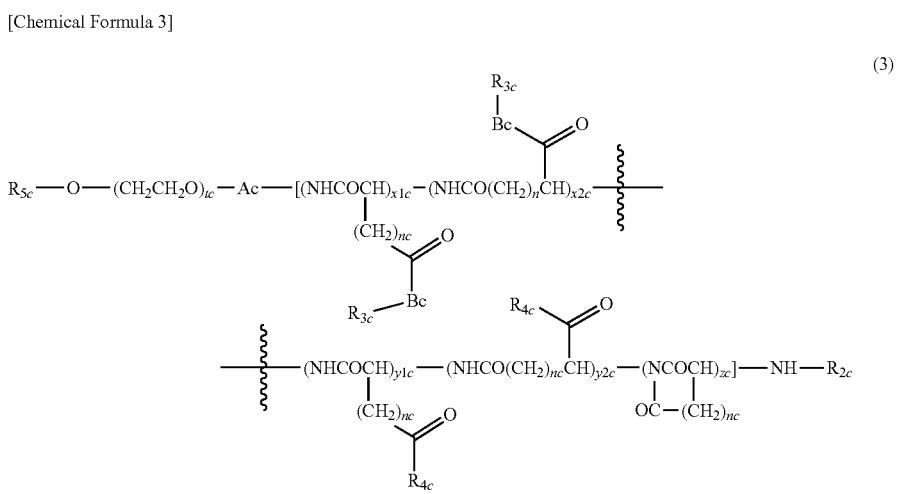

(3)

wherein
- $R_{5c}$ represents a hydrogen or a (C1-C6) alkyl group which may have a substituent;
- tc represents an integer from 20 to 140;
- Ac represents a (C1-C6) alkylene group which may have a substituent;
- $R_{2c}$ represents a substituent selected from the group consisting of a hydrogen atom, a (C1-C6) acyl group, and a (C1-C6) alkoxycarbonyl group;
- $R_{3c}$ represents a bonding residue of a physiologically active substance having a hydroxy group and/or an amino group;
- $R_{4c}$ is a bonding residue of a hydrophobic substituent and represents one or more substituents selected from the group consisting of a linear, branched or cyclic (C1-C30) alkoxy group which may have a substituent, a linear, branched or cyclic (C1-C30) alkylamino group which may have a substituent, a linear, branched or cyclic (C1-C30) dialkylamino group which may have a substituent, a (C1-C8) alkylaminocarbonyl-(C1-C8) alkylamino group which may have a substituent, a bonding residue of a fluorescent substance having a hydroxy group and/or an amino group, and a hydroxy group;
- Bc represents a single bond or a divalent bonding group;
- nc represents 1 or 2;
- x1c, x2c, y1c, y2c, and zc each independently represent an integer from 0 to 20;
- (x1c+x2c) is an essential configuration and represents an integer from 1 to 20;
- (x1c+x2c+y1c+y2c+zc) represents an integer from 3 to 20; and
- the respective constituent units having $R_{3c}$ and $R_{4c}$ bonded thereto, and a constituent unit formed by intramolecular cyclization of a side-chain carbonyl group constitute a structure with those constituent units being each independently randomly arranged; and wherein the main chain polymer of the block copolymer (C) combining the polyethylene glycol chain and the polyamino acid chain has a molecular weight of not less than 2 kilodaltons and not more than 7 kilodaltons, and a mass content percentage of the physiologically active substance with a hydroxy group and/or an amino group in the block copolymer (C) is not less than 5% by mass and not more than 60% by mass.

2. The composition according to claim 1, wherein the composition comprising the block copolymer (A) and the block copolymer (C) forms nanoparticles in an aqueous solution, and the nanoparticles have an average particle size of 30 nanometers or less.

3. A medicine comprising the composition according to claim 1.

* * * * *

UNITED STATES PATENT AND TRADEMARK OFFICE
CERTIFICATE OF CORRECTION

PATENT NO. : 10,973,762 B2
APPLICATION NO. : 16/320143
DATED : April 13, 2021
INVENTOR(S) : Dai Kurihara et al.

Page 1 of 1

It is certified that error appears in the above-identified patent and that said Letters Patent is hereby corrected as shown below:

In the Claims

Column 82, Line 22:
"Ria" should read --$R_{3a}$--

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*